US012605190B2

(12) United States Patent
Leff et al.

(10) Patent No.: US 12,605,190 B2
(45) Date of Patent: Apr. 21, 2026

(54) PEDICLE SCREW STABILIZATION SYSTEMS AND INSTRUMENTS

(71) Applicant: GLOBUS MEDICAL, INC., Audubon, PA (US)

(72) Inventors: David Leff, Philadelphia, PA (US); Caelan Allen, Ambler, PA (US); Matthew Bechtel, Philadelphia, PA (US); George Yacoub, Lansdale, PA (US)

(73) Assignee: Globus Medical, Inc., Audubon, PA (US)

( * ) Notice: Subject to any disclaimer, the term of this patent is extended or adjusted under 35 U.S.C. 154(b) by 57 days.

(21) Appl. No.: 18/406,445

(22) Filed: Jan. 8, 2024

(65) Prior Publication Data

US 2025/0221743 A1 Jul. 10, 2025

(51) Int. Cl.
*A61B 17/70* (2006.01)
*A61B 17/86* (2006.01)
(52) U.S. Cl.
CPC ...... *A61B 17/7082* (2013.01); *A61B 17/7008* (2013.01); *A61B 17/8665* (2013.01); *A61B 2017/867* (2013.01)
(58) Field of Classification Search
CPC ............ A61B 17/7032; A61B 17/7034; A61B 17/7035; A61B 17/7037
See application file for complete search history.

(56) References Cited

U.S. PATENT DOCUMENTS

| | | | |
|---|---|---|---|
| 8,535,318 B2 | 9/2013 | Peterson et al. | |
| 10,258,385 B1 * | 4/2019 | Doubler | A61B 17/7037 |
| 10,695,102 B2 * | 6/2020 | May | A61B 17/7032 |
| 10,932,826 B2 | 3/2021 | Hutton et al. | |
| 11,020,150 B1 | 6/2021 | Doubler et al. | |
| 11,857,222 B1 * | 1/2024 | Leff | A61B 17/8695 |
| 12,076,054 B2 * | 9/2024 | Leff | A61B 17/7032 |
| 12,144,524 B2 | 11/2024 | Allen et al. | |
| 2013/0110177 A1 | 5/2013 | Doubler et al. | |
| 2019/0247094 A1 * | 8/2019 | Yacoub | A61B 17/7035 |
| 2020/0323563 A1 | 10/2020 | Rezach et al. | |
| 2021/0282820 A1 | 9/2021 | Morris | |
| 2022/0125484 A1 | 4/2022 | Jackson | |
| 2022/0249134 A1 | 8/2022 | May et al. | |
| 2022/0257289 A1 | 8/2022 | Leff et al. | |
| 2023/0404638 A1 * | 12/2023 | Leff | A61B 17/8695 |
| 2024/0325055 A1 | 10/2024 | LaRosa et al. | |

FOREIGN PATENT DOCUMENTS

JP 2023-143859 A 10/2023

* cited by examiner

*Primary Examiner* — Ellen C Hammond

(57) ABSTRACT

Orthopedic fixation devices, assemblies, instruments, and methods relating to the same. The orthopedic fixation device may include a tulip head with one or more internal components configured to secure a bone fastener, such as a saddle, retaining clip, and friction ring. A spinal rod may be secured in the tulip head, for example, with a locking cap, thereby securing the bone fastener. One or more instruments, such as screwdrivers and correction instruments may be used for reduction, derotation, compression and/or distraction.

8 Claims, 54 Drawing Sheets

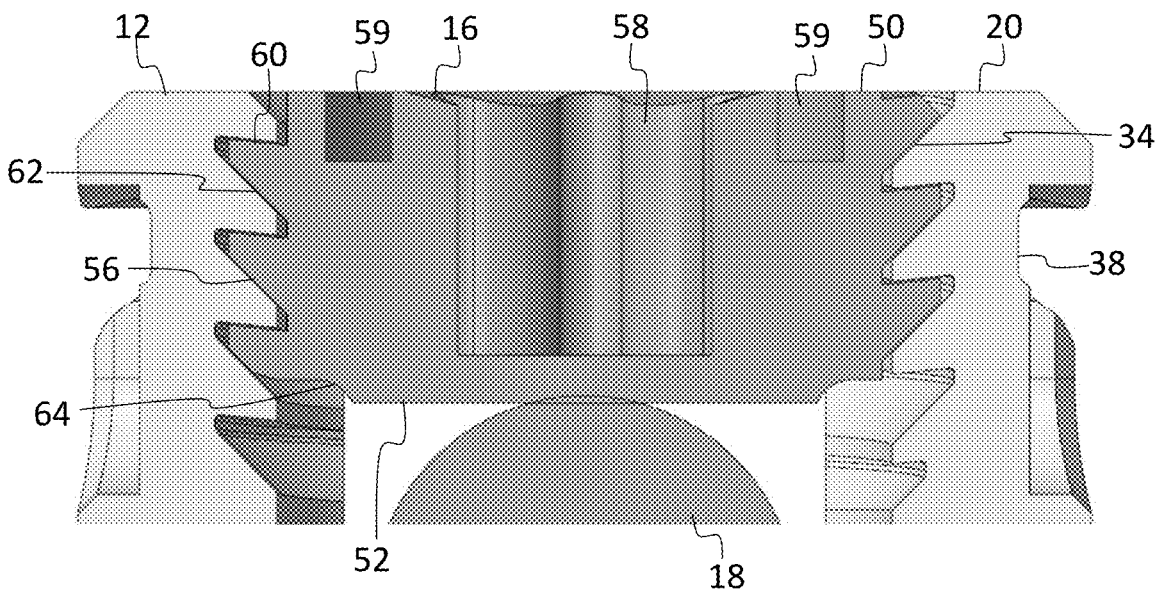
FIG. 3A
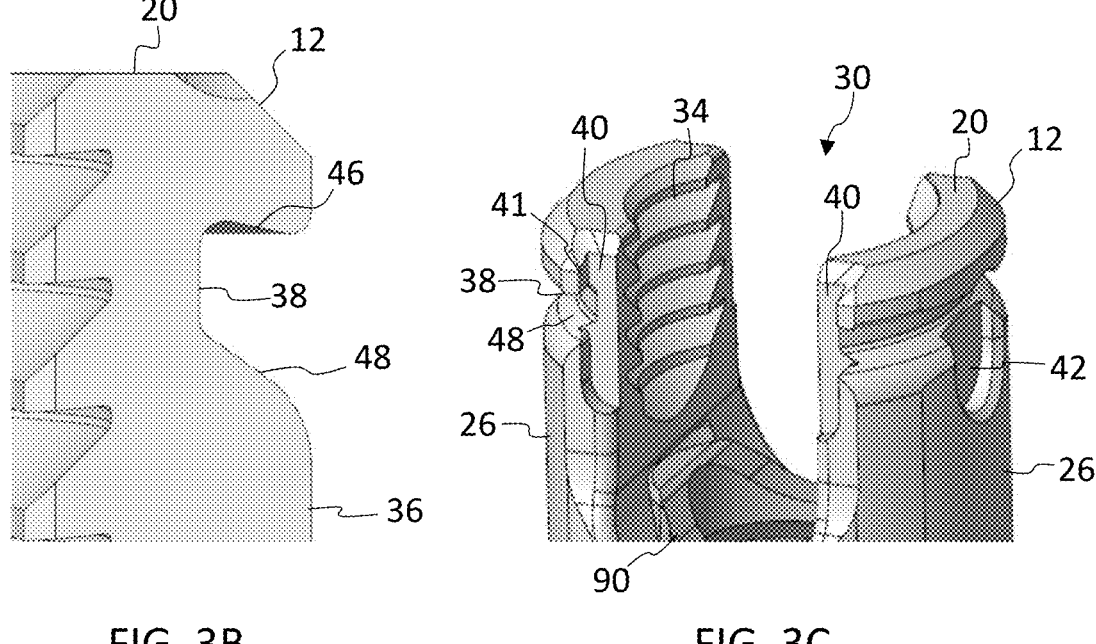
FIG. 3B                    FIG. 3C

14
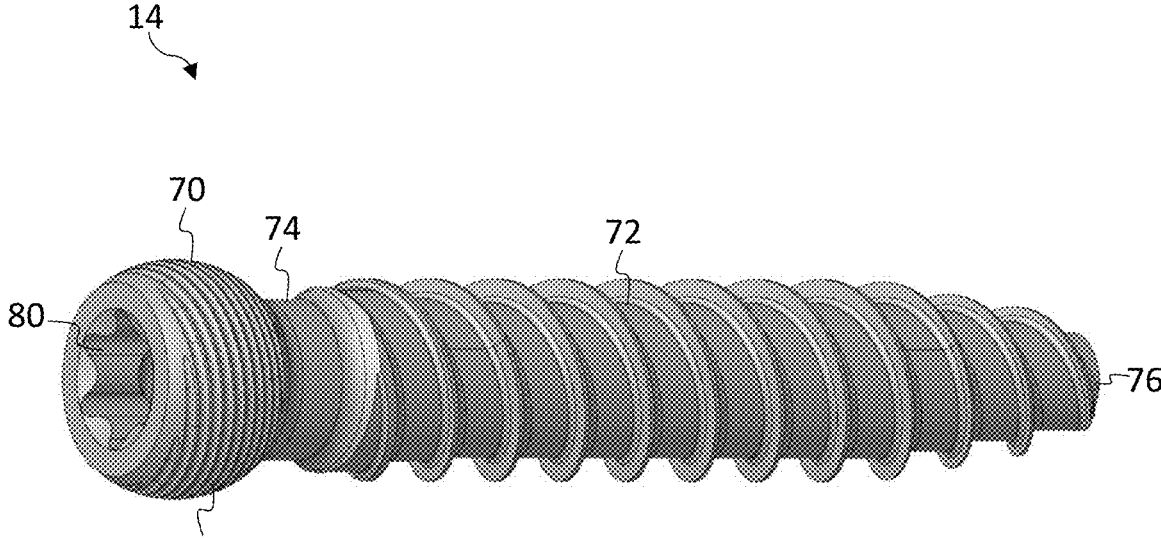
FIG. 4A
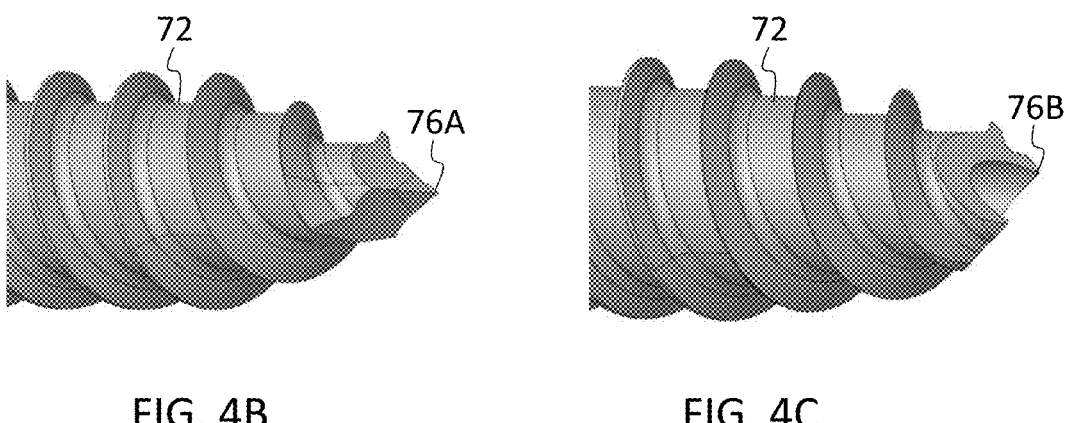
FIG. 4B                              FIG. 4C

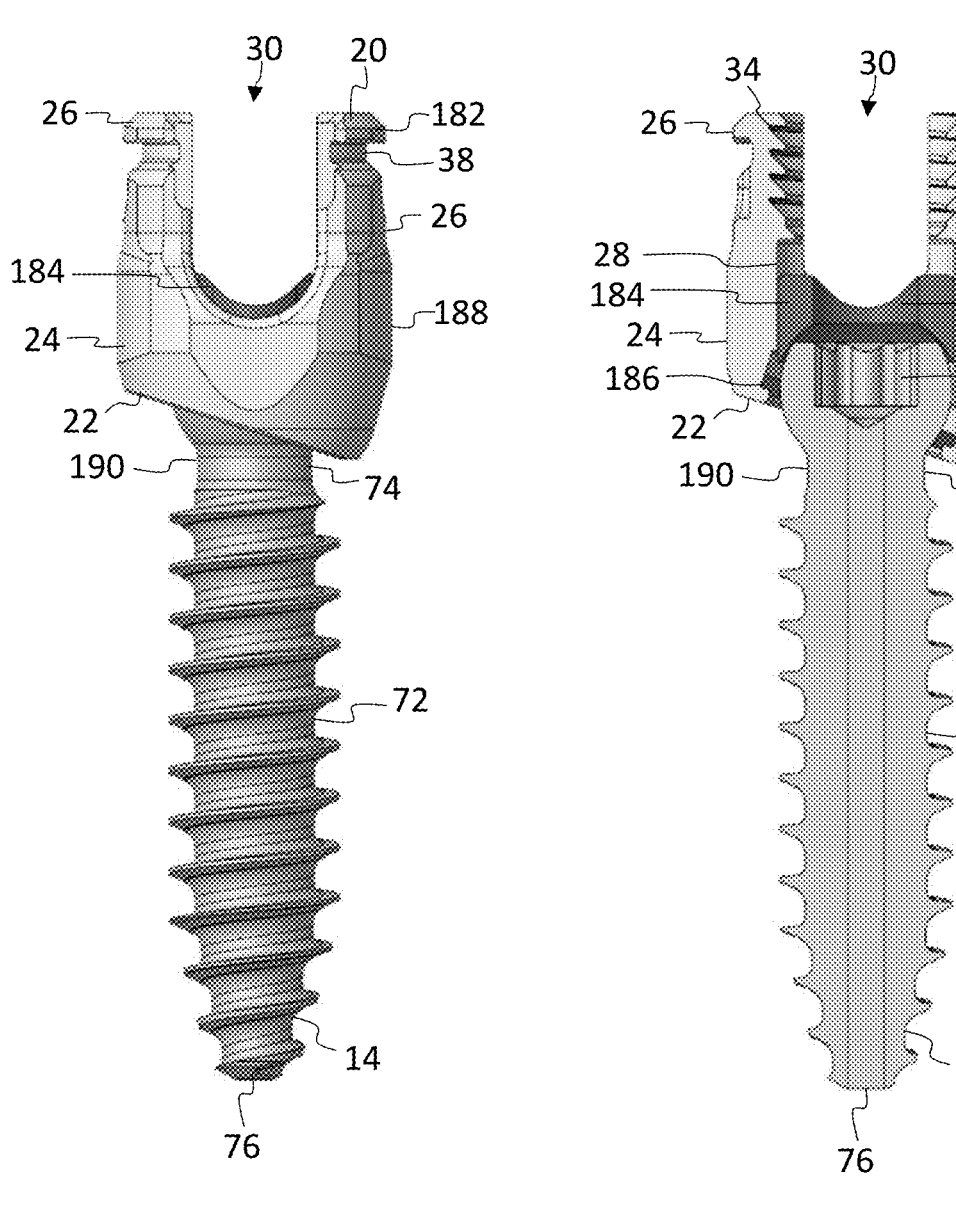
FIG. 9A                    FIG. 9B

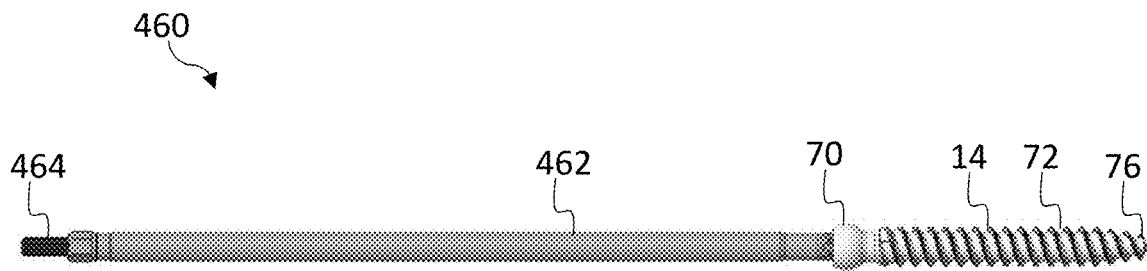
FIG. 28A
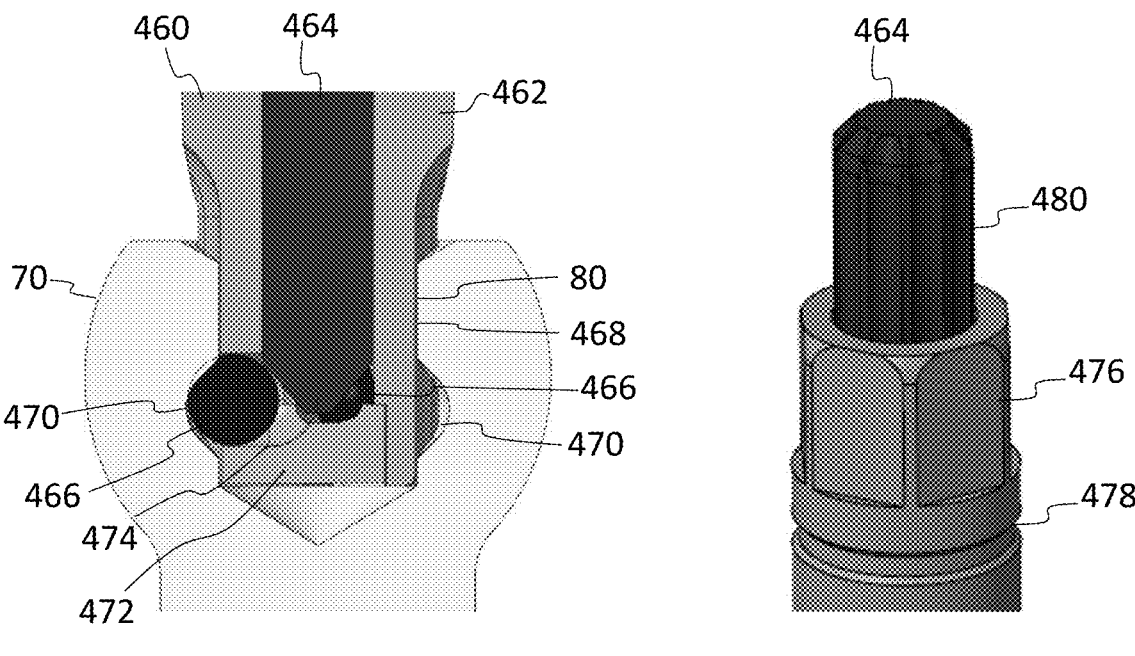
FIG. 28B                    FIG. 28C

540

546          542          544  548          550

556                         562

540

546  554          542          564  544  548  562
                                                 558
                                          552

550

568  560
556          554          542

546

570
568  566

600

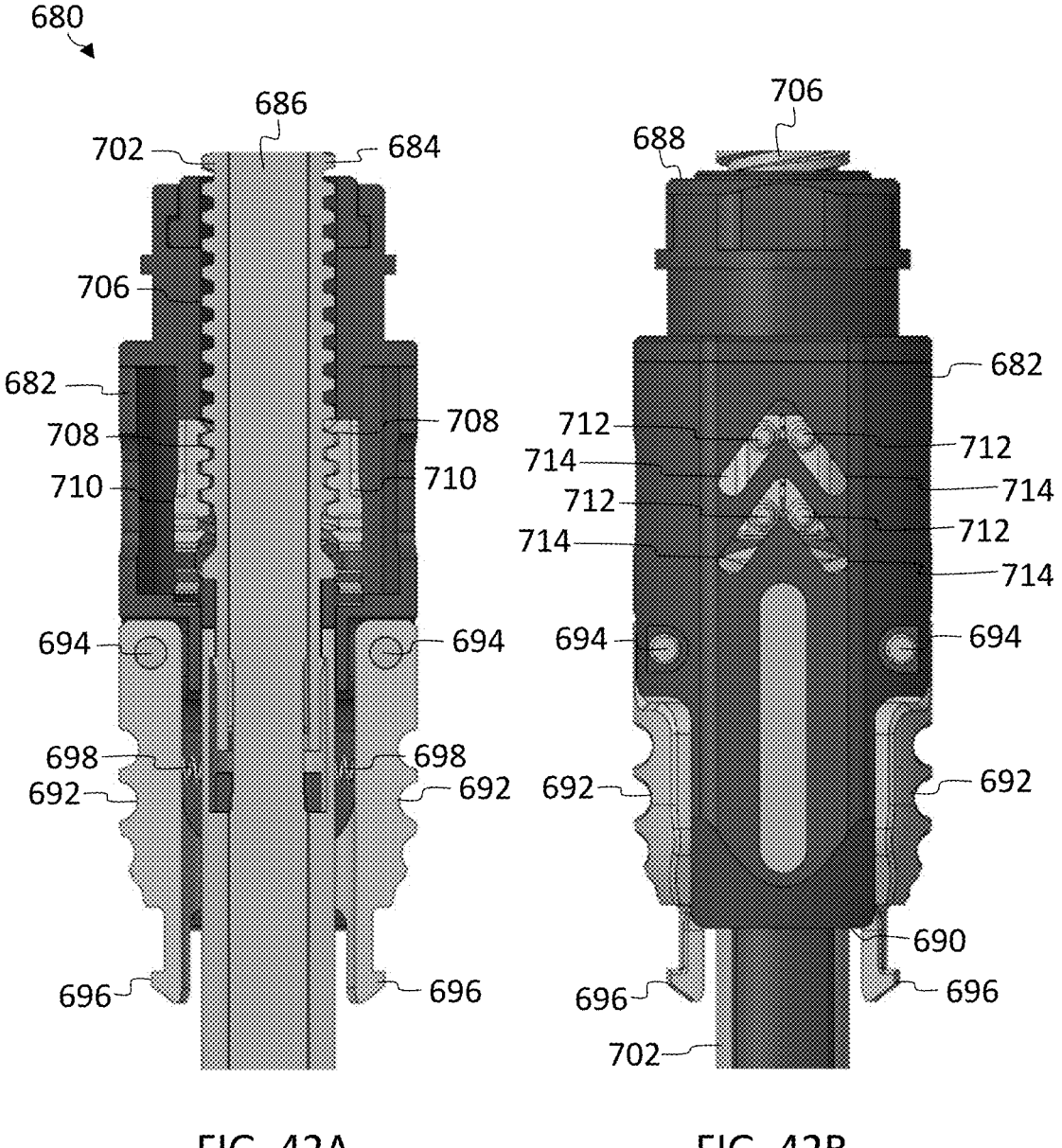
FIG. 42A                    FIG. 42B

PEDICLE SCREW STABILIZATION SYSTEMS AND INSTRUMENTS

FIELD OF THE INVENTION

The present application relates generally to orthopedic fixation devices and instruments, and more particularly, bone fastener assemblies, for example, for spine surgery and instruments for installing the same.

BACKGROUND OF THE INVENTION

Many types of spinal irregularities cause pain, limit range of motion, or injure the nervous system within the spinal column. These irregularities may result from, without limitation, trauma, tumor, disc degeneration, and disease. Often, these irregularities are treated by immobilizing a portion of the spine. This treatment typically involves affixing a bone fastener to one or more vertebrae and connecting the bone fastener(s) to an elongate spinal rod that stabilizes members of the spine.

The bone fixation device may include a tulip head for coupling the bone fastener to the elongate spinal rod. A locking cap may be used to secure the elongate spinal rod in the tulip head. One or more instruments may also be used to correct deformities and spinal irregularities. There exists a need for improved pedicle screw systems with a variety of implant options to suit pathologies having increased strength, decreased splay, and improved instrument connections.

SUMMARY OF THE INVENTION

To meet this and other needs, bone fastener devices, assemblies, systems, instruments, and methods of treating spinal irregularities are provided. The bone fastener may include a tulip head with a locking cap for securing the spinal rod therein. The bone fastener may be configured for use with a variety of screws, such as polyaxial, uniplanar, monoaxial, reduction, modular, etc. The bone fastener may be implanted, for example, in open, semi-open, or percutaneous approaches to the posterior spine.

According to one embodiment, an orthopedic fixation assembly includes a tulip assembly including a tulip head, a saddle, a retaining clip, and a friction ring. The tulip head has two arms defining a rod slot therebetween and a bore extending therethrough. The saddle is receivable in the bore of the tulip head. The saddle has an upper surface defining a rod seat aligned with the rod slot. The retaining clip is positioned at the bottom of the tulip head, and the friction ring is positioned between the saddle and the retaining clip. The bone fastener includes a screw head receivable in the tulip head and a shaft configured for engaging bone.

The orthopedic fixation assembly may include one or more of the following features. The retaining clip may include a split ring configured to rest in a corresponding groove in the tulip head. The retaining clip may include an upper radial neck configured to rest on a shelf in the groove in the tulip head. The friction ring may include a split ring configured to rest in a corresponding groove in the tulip head. The friction ring may have a smooth circular profile and the groove may have a semi-circular cross section to accommodate the friction ring. The screw head may include helical grooves, and the friction ring may be located around the screw head and in engagement with the helical grooves to help the tulip head retain its angular position relative to the bone fastener when positioned by a user. The orthopedic fixation assembly may include a locking cap having an outer body defining a thread. The locking cap may be threadable between the two arms of the tulip head to secure a rod therein. The locking cap may include a circular groove in a top face surrounding a drive recess. The circular groove may be configured to receive one or more prongs from a driver to retain the locking cap. When the locking cap is threaded downwardly onto the rod, the rod pushes against the rod seat of the saddle, and the saddle secures the bone fastener in a locked position.

According to one embodiment, an orthopedic fixation system includes an implant with a tulip head and a bone fastener, a tower body, and a tower removal tool. The tulip head has two arms defining a rod slot therebetween. The arms define a circumferential groove. The bone fastener includes a screw head receivable in the tulip head and a threaded shaft for engaging bone. The tower body includes a proximal base and two distal arms with rod slot defined therebetween. The distal arms include retaining tabs having inner hooks configured to grip the circumferential groove of the tulip head. When connected thereto, the rod slot of the tower body is configured to align with the rod slot of the tulip head. An underside of each retaining tab has a projection passing through a slot in the distal arms. The tower removal tool is configured to be inserted through the tower body. The tower removal tool includes an outer sleeve with elongated openings and spreaders sized and dimensioned to fit through the elongated openings and engage the projections on the underside of the each retaining tab to release the retaining tabs from the tulip head.

The orthopedic fixation system may include one or more of the following features. The elongated openings and spreaders may have an obround shape. The spreaders may define angled slots, which ride along pins connected to the outer sleeve of the tower removal tool. The angled slots may include a pair of parallel slots on each spreader. A first spreader may have a first pair of angled slots with a lower distal portion slanted to a higher proximal portion, and a second spreader may have a second pair of angled slots with a higher distal portion slanted to a lower proximal portion. The tower removal tool may include an inner shaft, which when translated distally, causes the spreaders to extend outwardly to engage the retaining tabs. A proximal end of the outer sleeve may include guides in the form of axial tabs on opposite sides of the outer sleeve, which are configured to fit within corresponding slots in the tower.

According to one embodiment, a method of installing an orthopedic fixation device may include one or more of the following steps in any suitable order: (1) providing an implant including a tulip head having two arms defining a rod slot therebetween with a saddle, a retaining clip, and a friction ring housed in the tulip head, and a bone fastener including a screw head having helical grooves and a threaded shaft, wherein the screw head is receivable in the tulip head such that the friction ring is located around the screw head and in engagement with the helical grooves to help the tulip head retain its angular position relative to the bone fastener when positioned by a user; (2) inserting the shaft of the bone fastener into bone; (3) positioning a spinal rod between the two arms and into the rod slot of the tulip head; (4) threading a locking cap downwardly between the two arms of the tulip head, wherein the rod presses against a rod seat of the saddle, and the saddle presses against the screw head of the bone fastener, thereby locking the spinal rod and bone fastener; (5) attaching a tower with tulip retaining tabs to the tulip head to provide a guide and working channel in percutaneous approaches; (6) removing the tower with a tower removal tool having spreaders, which when actuated, interface with an underside of each retaining tab to splay the retaining tabs open and release the tulip head from the tower; (7) attaching a reducer assembly to a proximal end of the tower to push the spinal rod into the tulip head; and (8) attaching a compression and/or distraction instrument to the tower, wherein the tower attached to the tulip head compresses or distracts the attached bone.

According to one embodiment, a reducer instrument includes a tower body and a reducer assembly. The tower body includes a proximal base and two distal arms with a rod slot defined therebetween for releasably securing pedicle connectors configured to attach to respective vertebrae. The reducer assembly has an outer housing, an inner pusher, and a locking cap driver aligned along a central tool axis. The outer housing attaches to cutouts on a proximal end of the tower body via releasable spring clips. The inner pusher has a tubular body with an outer threaded portion, which is sized and dimensioned to receive the locking cap driver. A pair of half nuts are secured in the outer housing on pins, which ride along ramped slots in the outer housing. The half nuts are externally threaded to interface with the outer threaded portion of the inner pusher. When axial force is applied to the inner pusher in a distal direction, the half nuts are forced into an open state by translating in the ramped slots, allowing the inner pusher to bypass the external threads of the half nuts. When axial force is applied to the inner pusher in a proximal direction, the half nuts are forced into a locked state by translating in the ramped slots, allowing the half nuts to engage with the inner pusher.

The reducer instrument may include one or more of the following features. When in the open state, the pins may translate in the ramped slots away from the central tool axis, and when in the locked state, the pins may translate in the ramped slots toward the central tool axis. The ramped slots may include two pairs of angled slots angled toward the central tool axis at a proximal end and away from the central tool axis at a distal end of the slots. The spring clips may be pivotably coupled to the outer housing via pivot pins. The distal ends of the spring clips may include outward-facing keying prongs, which interface with corresponding slots on the tower body to prevent rotation during usage. The spring clips may be spring loaded via inner springs to bias the prongs outward, thereby securing the reducer assembly to the tower body. The half nuts may be spring-loaded to ensure engagement with the inner pusher.

According to one embodiment, a reducer system includes a tulip assembly, a tower body, and a reducer assembly. The tulip assembly includes a tulip head having a rod slot for receiving a spinal rod and a bone screw attached to the tulip head with a threaded shaft, which is attachable to a vertebra. The tower body includes a proximal base and two distal arms with a rod slot defined therebetween. When connected thereto, the rod slot of the tower body is configured to align with the rod slot of the tulip head. The reducer assembly has an outer housing and an inner pusher. The outer housing attaches to the proximal base of the tower body. The inner pusher has a tubular body with an outer threaded portion. A pair of half nuts are secured in the outer housing on pins, which ride along ramped slots in the outer housing. The half nuts are externally threaded to interface with the outer threaded portion of the inner pusher. The inner pusher is configured to push the spinal rod along the rod slot of the tower body and into the rod slot in the tulip head, thereby allowing for precise positioning and alignment of the spinal rod in the tulip head. When the spinal rod applies a reduction load onto the inner pusher, the half nuts may translate in the ramped slots toward a centerline of the reducer assembly, allowing the half nuts to engage with the inner pusher. When an axial force is applied onto the inner pusher in a distal direction, the half nuts may translate in the ramped slots outward and away from the centerline of the reducer assembly, allowing the half nuts to disengage from the inner pusher.

According to one embodiment, a spinal manipulation instrument includes first and second arms configured for releasably securing pedicle connectors configured to attach to respective vertebrae, a driving rod with a threaded portion defining a rod axis therethrough, wherein the first and second arms threadedly interface with the driving rod such that one of the arms translates along the driving rod in response to rotation of the driving rod about the rod axis, and a separate detachable fulcrum instrument is positionable through the first and second arms in two different orientations to provide for lordotic or parallel movement of the first and second arms.

The spinal manipulation instrument may include one or more of the following features. The first arm may be a moveable arm and the second arm may be a fixed arm. The first and second arms may have a nesting configuration where proximal ends of the arms fit together. One arm may have a pronounced rounded male interface at the proximal end, which nests within a corresponding rounded female interface on the other arm to provide for pivotal movement between the first and second arms in the lordotic orientation. The first and second arms may define a first set of bores along a first axis, which is parallel to the rod axis. The first and second arms may define a second set of bores along a second axis, which is perpendicular to the rod axis. When the detachable fulcrum is inserted through the first set of bores, the fulcrum may act as a guide rail for the first and second arms to translate across for parallel movement, and when the detachable fulcrum is inserted through the second set of bores, the fulcrum may act as a pivot point for the first and second arms for lordotic movement. A modular connector tip for securing a tower may be coupled to each arm. A distal end of each arm may include a connector post that extends from an attachment end to a free end for receiving the modular connector tip. The connector post may define a circumferential groove configured to interface with a button on the modular connector tip with a protrusion that automatically engages with the groove.

Also provided are kits including implants of varying types and sizes, rods, bone anchors, fasteners, various instruments, guides, and tools, guide wires, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 3A-3C show a close-up section view of the tulip head and locking cap, a close-up section view of a circumferential groove in the tulip head, and a close-up perspective view of the tulip head reduction features according to one embodiment;

FIGS. 4A-4C show a perspective view showing one example of a bone fastener and close-up views of a three-sided trocar tip and a cannulated screw with cutting edges, respectively;

FIGS. 9A-9B show a perspective view and cross-sectional view of a second sacral-alar-iliac (S2AI) screw assembly according to one embodiment;

FIGS. 28A-28D show a side view of a screw extender, a cross section of the screw extender engaged with the screw, a top perspective view of the screw extender, and a cross-section of the screw extender driver according to one embodiment;

FIGS. 42A-42B show cross-sectional and side views, respectively, of the reducer assembly according to one embodiment;

DETAILED DESCRIPTION OF THE INVENTION

Embodiments of the disclosure are generally directed to bone fastener devices, assemblies, systems, instruments, and methods for securing a bone fastener and/or spinal rod. Specifically, embodiments are directed to tulip assemblies and systems configured to secure the spinal rod to the bone fastener. In some embodiments, the systems include pedicle screw systems with varying types of heads, such as polyaxial, modular, reduction, uniplanar, monoaxial, sacral-alar-iliac (S2AI), closed head, and varying types of screws, such as solid, cannulated, fenestrated, single step, cortical, dual outer diameter, corticocancellous, and hydroxyapatite (HA) coated. A locking cap mates with the heads of the screws and locks a spinal rod to the screw head, forming a rigid construct for stabilization of the spine. Additional implants may include hooks and other connectors.

The systems may be used for both open and percutaneous approaches including minimally invasive surgical (MIS) procedures for a variety of conditions including degenerative conditions, deformities, tumors, traumas, and infections. Mating instruments interface with connecting features on the screw head and screws for insertion, manipulation, correction, and locking of implants. A MIS tower may be attached to the screw head to provide a guide and working channel for percutaneous approaches.

Screwdrivers or other instruments may be used for placement of screws into vertebrae under fluoroscopic, image guided, and robotic guided approaches. Screw extenders may be used for registration and tracking of bony anatomy, for example using a robotic navigation system. Examples of surgical robotic and/or navigation systems can be found, for example, in U.S. Pat. Nos. 10,675,094 and 9,782,229, which are incorporated by reference herein in their entireties for all purposes. Correction instruments may be used for reduction, segmental derotation, en-bloc derotation, global derotation, compression, and distraction. Although generally described with reference to the spine, it will be appreciated that the devices and systems described herein may be applied to other orthopedic locations and applications, such as trauma applications.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

Figure 1:
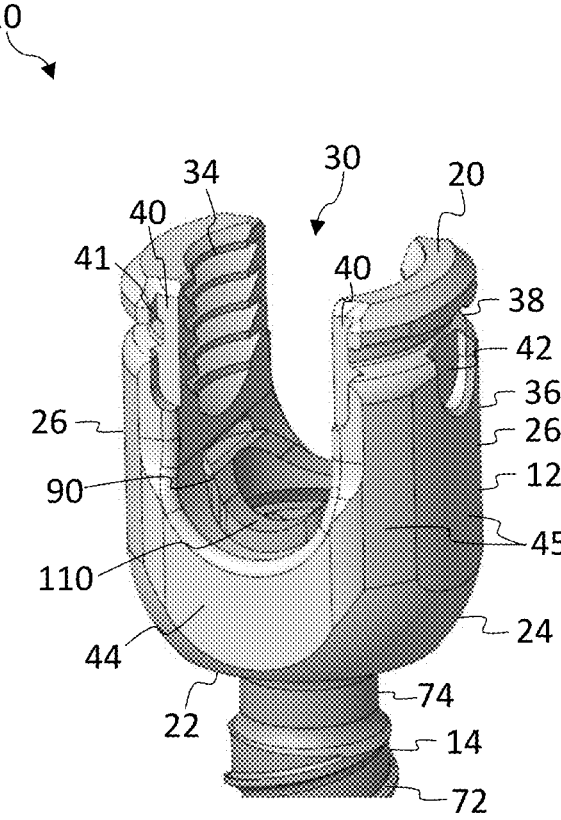
FIG. 1 is a partial perspective view of an orthopedic fixation assembly including a tulip head configured to receive a spinal rod and bone screw according to one embodiment.
Figure 2:
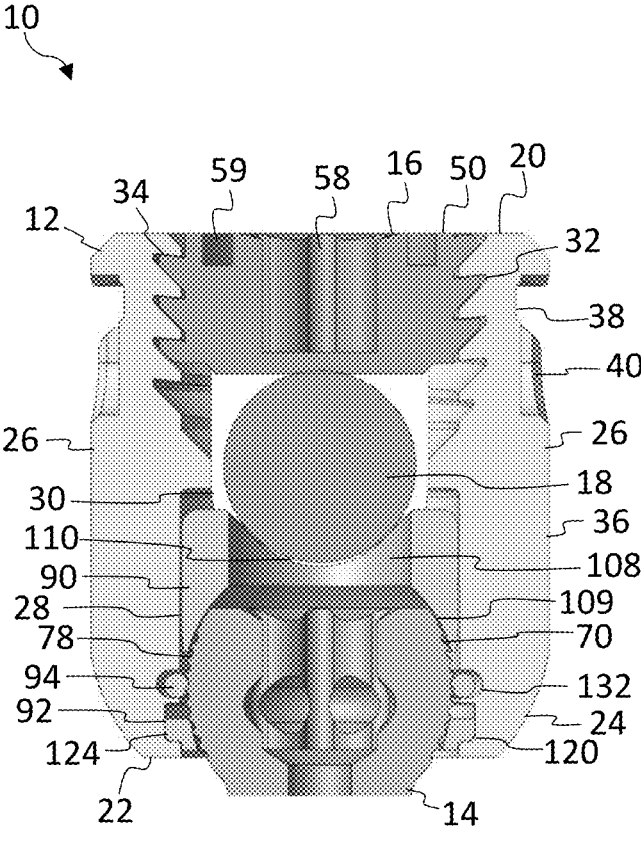
FIG. 2 shows a cross-sectional view of the orthopedic fixation assembly including the tulip head, spinal rod, and locking fastener according to one embodiment.

Turning now to the drawing, where like reference numerals refer to like elements, FIGS. 1-5 show an orthopedic fixation device, implant, or bone fastener assembly 10 according to one embodiment. The implant or bone fastener assembly 10 may include a screw head or tulip head 12 attachable to a bone fastener 14. The assembly 10 may have varying mechanisms that achieve different amounts of angulation. As best seen in FIG. 2, the screw head or tulip head 12 is configured to receive a locking cap 16 to secure a spinal rod 18 therein. For a polyaxial bone fastener 14, tightening the locking cap 16 compresses the rod 18 into the tulip head 12, thereby restricting motion of the bone fastener 14 and forming a rigid construct.

The tulip head 12 extends from an upper surface or top 20 to a lower surface or bottom 22 along a central longitudinal axis. The tulip head 12 may include a base or body 24 and arms 26 that extend upwardly from the body 24. The arms 26 may be aligned generally in parallel with one another. A central bore 28 may extend through the body 24 of the tulip head 12. The opposed arms 26 may define a U-shaped channel or rounded rod slot 30, transverse to the bore 28. The rod slot 30 is sized and configured to accept the rod 18 perpendicular to the threads of the locking cap 16. The rod slot 30 may be sized to accept rods of varying diameters and curvatures. Each of the arms 26 has an interior surface 32 having a threaded portion 34 for engaging the locking cap 16. These threads 34 intersect the rod slot 30 to accept the locking cap 16 to lock the rod 18 to the tulip head 12 and restrict the motion of the head's angulation mechanism.

As best seen in FIG. 3A, the rod 18 may be secured in the tulip head 12 with the locking cap 16. The locking cap 16 may include a body with an upper surface 50, a lower surface 52, and an outer body defining a threaded portion 56. The locking cap 16 may be in the form of a set screw with a drive feature or recess 58 defined in the upper surface 50 configured to be engaged by a driving instrument, which is able to insert and tighten the locking cap 16 in the tulip head 12. The recess 58 may be a hexalobe, slot, cross, or other suitable shape that may engage with a tool or device having a corresponding tip. The recess 58 may extend partially into the body of the locking cap 16 or entirely through the locking cap 16. A circular groove 59 may be provided in the top surface 50 of the locking cap 16 to interface with an instrument (as shown in more detail in FIGS. 13A-13B). The bottom 52 of the locking cap 16 may be flat or otherwise configured to ensure desired contact with the rod 18.

The external threaded portion 56 of the locking cap 16 may have a thread geometry configured to secure the locking cap 16 to the tulip head 12. The external threaded portion 56 of the locking cap 16 may extend between the upper and lower surfaces 50, 52. The internal threads 34 within the tulip head 12 mate with external threads 56 of the locking cap 16. Tightening the locking cap 16 compresses the rod 18 into the head 12 and internal components, thereby restricting motion of the screw 14 and forming a rigid construct.

In one embodiment shown in FIG. 3A, the threads 34, 56 of the locking cap 16 and tulip head 12 may be configured to intermesh to prevent or reduce splaying of the arms 26 of the tulip 12. In one embodiment, locking cap threads 56 are a reverse buttress design, with an inward-facing top surface 60 and outward-facing flank 62. The inward-facing top surface 60 resists outward splaying forces, and the outward-facing flank surface 62 provides structural strength across the root of the threads 56. It will be appreciated that other suitable threaded or non-threaded connections may also be used.

As best seen in FIGS. 3B-3C, each of the arms 26 may include an outer surface 36 with one or more features for engagement with mating instruments. One or more instrument interfaces may be used for engagement with one or more instruments, such as insertion, positioning, reduction, derotation, compression, distraction and/or other holding instruments. The instrument interfaces allow one or more instruments to fully or partially constrain or attach to the implant, provide increased holding strength, decrease splaying forces which may cause disengagement of the instrument, reduce and lever the rod into position, and/or simplify manufacturing. In some embodiments, the instrument engagement features 38, 40, 42 attach to mating instruments to resist tension and rotational loads.

With emphasis on FIG. 3B, each of the arms 26 may include a tool engagement groove 38, which may be used for holding the tulip head 12 with a suitable tool. In one embodiment, the tool engagement groove 38 is an annular or cylindrical groove defined into the outer surface 36 of the tulip head 12, which provides for engagement of insertion, reduction, derotation, or other holding instrument. The groove 38 may include a circumferential groove cut into the tulip head 12 with an inward-facing top surface 46 and on outward-facing lower surface 48. The inward-facing top surface 46 may have an inclined face that slopes such that it is lower toward the outer surface 36 and higher as the sloped surface 46 extends inward. The outward-facing lower surface 48 points toward the inward-facing top surface 46. The outward-facing lower surface 48 may also be slanted or sloped. For example, the outward-facing lower surface 48 may have the same or similar slope to the inward-facing top surface 46. The annular groove 38 may form an upper dovetail configured for engaging with the instrument. The inward-facing top surface 46 of the circumferential groove 38 prevents a mating instrument from disengaging when under tension.

As best seen in FIG. 3C, each of the arms 26 may include a tower pocket 40 configured to engage with mating instruments to constrain rotation of the instrument to the tulip head 12. The tower pockets 40 may include slots along the run-on-rod adjacent to the rod slot 30. For example, a vertical slot may be provided along an upper portion of each side of the arms 26. An inward-facing surface 41 of the slot 40 prevents the mating instrument from splaying and disengaging from the circumferential groove 38. The outward surfaces of the pockets 40 are configured to contact corresponding surfaces on the instrument, thereby preventing splay and disengagement of the instrument from the tulip head 12. In this manner, the inward-facing top surface 46 of groove 38 and inward-facing surfaces 41 of the slots 40 prevent the disengagement of mating instruments under tension and splaying loads. The circumferential groove 38 and tower pockets 40 may be combined to fully constrain the instrument to the tulip head 12.

The outer surface 36 of each arm 26 may also define a ball hole or rocker hole 42. The rocker holes 42 may interrupt the engagement groove 38, for example, at a central position on each arm 26. The rocker holes 42 may be cylindrical or obround pockets which allow engagement of a rocker-style instrument with pin features, allowing rotation of the instrument within the holes 42. Rotation about the rocker holes 42 allows the user to lever and reduce the rod 18 into the head 12.

Front and back exterior surfaces 44 of the tulip base 24 may be flat or planar and one or more rounded diameters 45 may be provided along the exterior of the tulip head 12. The flats 44 may be positioned on opposite sides of the tulip base 24, for example, below the rod slot 30. The flats 44 may act as an additional counter-rotation feature when engaged with an instrument. The rounded diameters 45 may be provided along the exterior arms 26 of the tulip head 12. The rounded exterior diameters 45 may have varying diameters, which mate with corresponding instruments.

In one embodiment, the reduction features are combined to include circumferential groove 38 with inward-facing top surface 46 and outward facing lower surface 48, slots 40 along the run-on-rod, and obround pockets 42. Instrument engagement features, such as circumferential groove 38, vertical slots 40, and obround pockets 42, attach to mating instruments to resist tension and rotational loads. Exterior flat surfaces 44 and diameters 45 may also mate with the instruments to provide a secure instrument connection.

The bone fastener 14 may be included in an assembly with tulip heads 12 of varying styles, or as a modular component where a modular head assembly is attached intraoperatively. The bone fastener 14 may include a bone screw, anchor, clamp, or the like configured to engage bone. In one embodiment, shown in FIG. 4A, the bone fastener 14 is a bone screw, such as a pedicle screw, having a screw head 70 connected to a threaded shaft 72 by a neck 74. The threaded shaft 72 includes one or more bone threads configured to engage bone. Varying bone thread forms may be used, such as corticocancellous, dual outer diameter (DOD), or cortical (MCS). Cannulations and fenestrations may also be employed for placement over a guide wire or k-wire and delivery of bone cement. The threaded shaft 72 may have a number of different features, such as thread pitch, shaft diameter to thread diameter, overall shaft shape, and the like, depending, for example, on the particular application. The threaded shaft 72 terminates at the distal end as distal tip 76. As shown in FIG. 4A, the tip 76 may be generally blunt to prevent damage to soft tissue. Alternatively, as shown in FIG. 4B, the tip 76A may be pointed, for example, with a three-sided trocar tip, or as shown in FIG. 4C, the tip 76B may include cutting edges around a cannulation to aid in starting the screw. It will be appreciated that varying tip geometries may be tailored for specific applications.

While the screw head 70 may have any general shape, in the case of a polyaxial fastener 14, at least a portion of the screw head 70 may have a curved surface in order to allow for rotational movement and/or angular adjustment of the bone fastener 14 with respect to the tulip head 12. For example, at least a portion of the screw head 70 may be shaped to form a portion of a ball or at least a portion of a sphere. The screw head 70 may be smooth, threaded, provided with a roughened or textured surface, or may be otherwise configured to interface with the tulip head assembly. In one embodiment, the bone fastener 14 has a spherical head 70 with grooves 78, such as helical grooves, configured to increase grip within the mating head assembly.

The screw head 70 may have a tool engagement surface or drive recess 80 that can be engaged, for example, by a screw-driving instrument or other device. The drive recess 80 is housed in the top of the head 70. In one embodiment, the drive recess 80 has a hexalobe shape for driving the screw 14 into bone. It will be appreciated that any suitably shaped tool engagement surface may be provided. Examples of bone fasteners, other implants, and rod constructs are described in more detail, for example, in U.S. Pat. No. 10,368,917, which is incorporated by reference herein in its entirety for all purposes.

Figure 5:
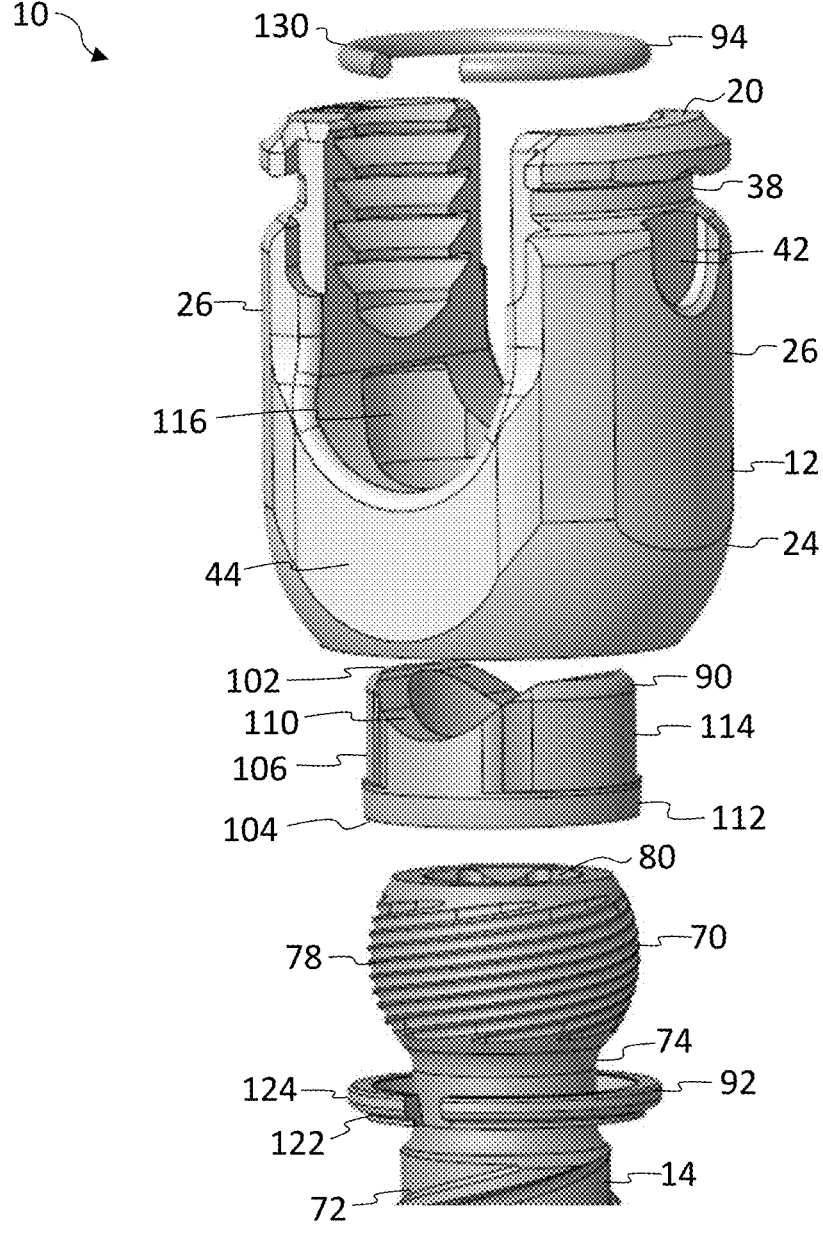
FIG. 5 shows an exploded view of a polyaxial screw assembly according to one embodiment.

With further emphasis on FIG. 5, an exploded view of tulip assembly 10 is shown according to one embodiment. The assembly 10 includes tulip head 12, bone fastener 14, a saddle 90, a clip 92, and a ring 94. The tulip head 12 houses all of the components 90, 92, 94. The polyaxial screw 14 permits angulation of the tulip head 12 about the bone screw 14 in each of the three rotations before rigidly locking its angulation when tightened by locking cap 16. The spinal rod 18 may also be secured into the tulip head 12 with the locking cap 16.

The saddle 90 applies compressive force to the bone screw 14 and restricts its angulation when the rod 18 is tightened to the implant 10 with the locking cap 16. The saddle 90 may have an upper surface 102, a lower surface 104, an outer surface 106, which may be curved or rounded, and a bore 108 defined through the saddle 90. As best seen in FIG. 2, a lower portion of the bore 108 may be rounded, for example, as a spherical pocket 109 sized and dimensioned to receive an upper portion of the spherical screw head 70. A rod slot or seat 110 may be defined in the upper surface 102 of the saddle 90. The rod seat 110 may be configured to receive a bottom portion of the rod 18 therein. The rod seat 110 may be generally aligned with the rod slot 30 through the tulip head 12. The saddle 90 may include a bottom rim 112 and two opposed elliptical profiles 114. The elliptical profiles 114 are configured to fit in corresponding elliptical bores 116 defined in the tulip 12. The elliptical bores 116 and corresponding profiles 114 are respectively sized so that the saddle 90 can be assembled to the tulip head 12 and not rotate out of alignment. When fully seated, the saddle 90 provides a collar about an upper portion of the screw head 80. The polyaxial motion of the screw 14 is locked when the locking cap 16 is threaded downwardly, compressing the rod 18 onto the saddle 90, which thereby compresses against the spherical head 80 of the bone screw 14.

The clip 92 retains the head 70 of bone screw 14 and is seated in the bottom of the tulip 12. The retaining clip 92 may be housed in an internal groove 120 in the tulip 12. The clip 92 may include a loop, ring, split-ring, snap ring, or other suitable retaining ring. In one embodiment, the retaining clip 92 may include a split ring 122 with a central through opening having a gap in fluid communication with the central through opening. The screw head 70 is positionable through the split ring 122 and may surround and apply compression to a bottom of portion of the screw head 70. An inner surface of the split ring 122 may engage the grooves 78 along the head 70 of the screw 14, providing increased friction and enhance the grip of the split ring 122 and the screw head 70. The retaining clip 92 may include an upper radial neck 124 protruding outward from the split ring 116. As best seen in FIG. 2, the radial neck 124 may form a shelf or ledge that rests in the corresponding groove 120 in the tulip 12, thereby holding the bone screw 14 in the tulip 12 and preventing disassembly.

The ring 94 may be a friction ring to further secure the bone fastener 14 in the tulip head 12. The friction ring 94 may be positionable in an internal groove 132 at the bottom of the tulip head 12 and located around the head 70 of the fastener 14. The friction ring 94 may be located beneath the saddle 90 and above the retaining clip 92. The friction ring 94 may include a split ring 130 with a central through opening and gap in fluid communication with the central through opening. The split ring 130 may have a smooth circular profile, such that when viewed across its diameter, the ring 130 has a circular cross section. The circular cross-section ensures uniform strength and flexibility around the ring's circumference. The groove 132 may also have a semi-circular or rounded cross section to accommodate the ring 94. The friction ring 94 may be sized with a slight interference fit with the tulip head 12 such that the head assembly can retain its angle against gravity when positioned by the user.

The components of pre-assembled implant 10 may be assembled together in the following manner. First, the saddle 90 may be inserted into the bottom of the tulip head 12. The saddle 90 may be seated in bore 28 such that the elliptical interface 114, 116 is aligned, thereby preventing saddle 90 from rotating out of alignment with the tulip 12. Next, the friction ring 94 may be inserted and seated into groove 132. The bone screw 14 is placed into the bottom of the tulip head 12, and the clip 92 is snapped into the groove 120 of the head component to retain the bone screw 14. The friction ring 94 may help the tulip head 12 to retain its angular position relative to the bone fastener 14 when positioned by the user. Once installed into the patient, the spinal rod 18 is positioned into the rod slot 30 of tulip 12 and into the rod seat 110 in the top of the saddle 90. The locking cap 16 is threaded 34, 56 into the top of the tulip 12. Tightening of the locking cap 16 compresses the spinal rod 18 into the rod seat 110 of the saddle 90, preventing rotation and translation about the rod 18. Force is transmitted through the saddle 90, compressing spherical head 70 of the bone screw 14 between the spherical pocket 109 of the saddle 90 and the clip 92. This locks the polyaxial motion of the tulip head 12 relative to the bone fastener 14.

Turning now to FIGS. 6A-7D, a modular tulip or head assembly 140 is shown according to one embodiment. The modular tulip assembly 140 functions similar to the pre-assembled polyaxial assembly 10 but permits intra-operative assembly of the tulip head 142 to the bone screw 14. The clip 92 of the pre-assembled polyaxial screw assembly 10 is replaced with a modular assembly, which allows for the tulip head 142 to be top loaded onto the bone screw 14 intraoperatively. The friction ring 94 is also omitted such that the head 142 does not have memory relative to the screw 14.

Figures 6A, 6B:
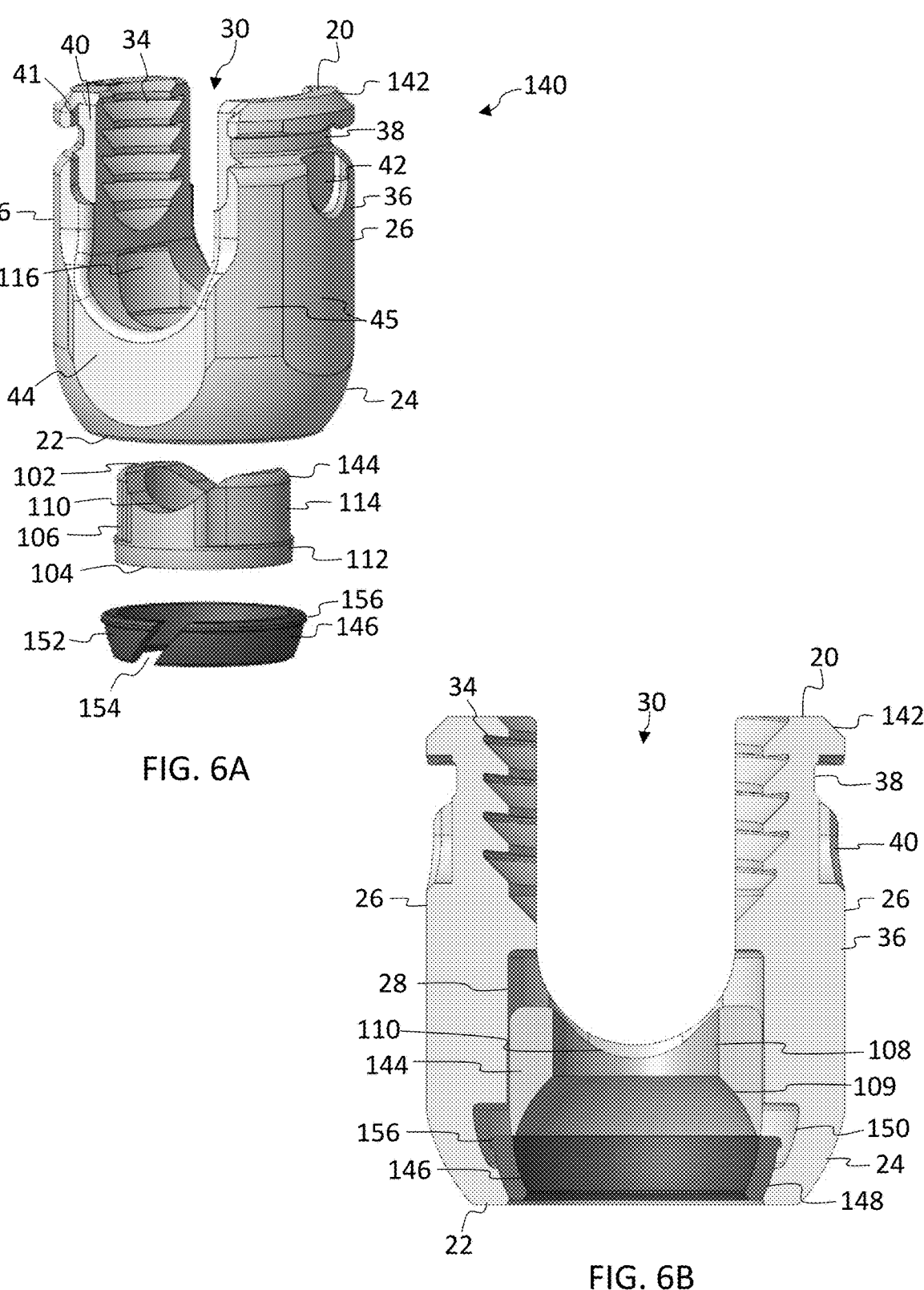
FIGS. 6A-6B show an exploded view and cross-sectional view, respectively of a modular polyaxial tulip assembly according to one embodiment.
Figures 7A, 7B, 7C, 7D:
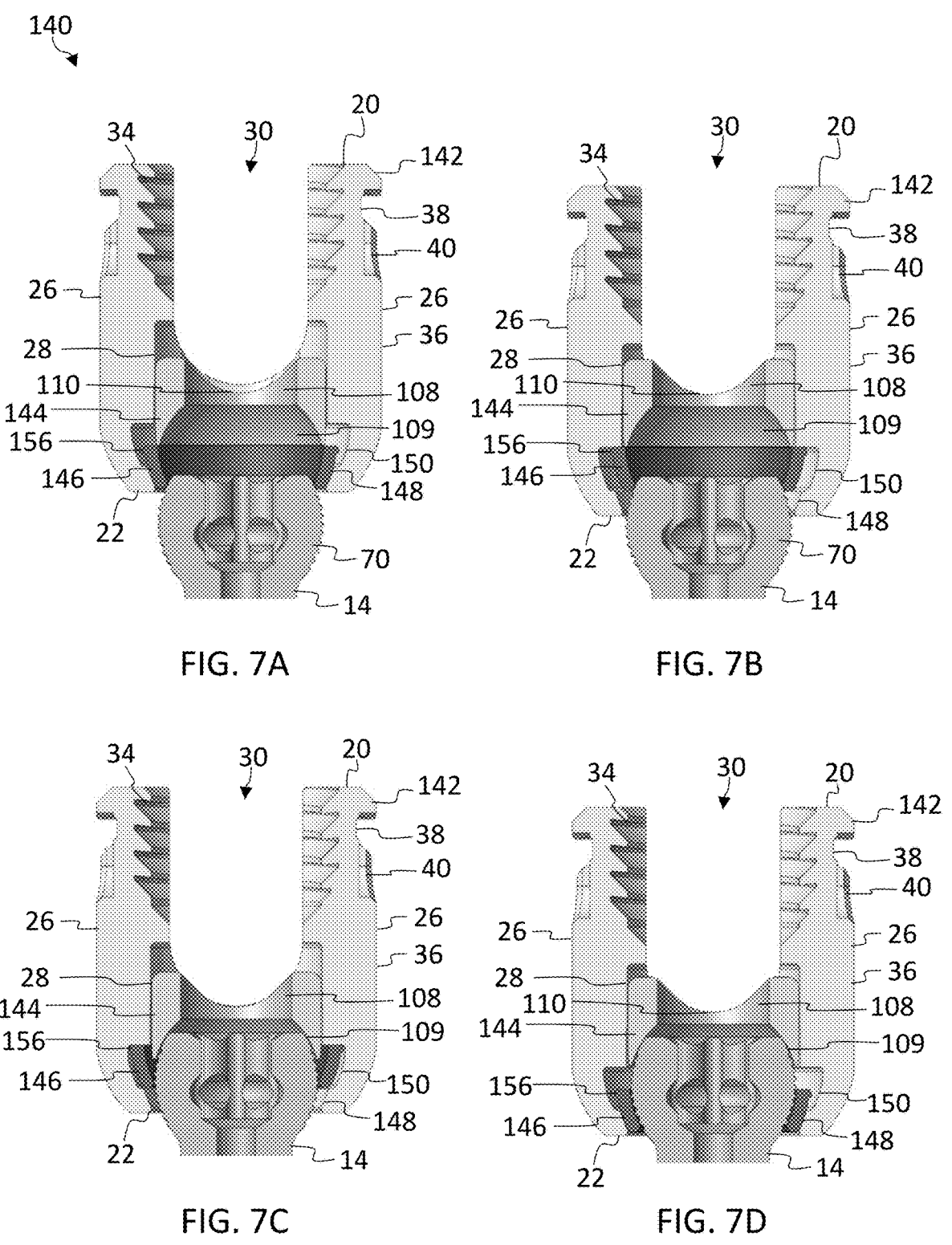
FIGS. 7A-7D show four stages of assembling the modular polyaxial tulip assembly to the bone fastener intraoperatively.

As best seen in FIGS. 6A-6B, the modular screw head assembly 140 includes tulip head 142, saddle 144, and modular clip 146. The tulip head 142 includes the same features as tulip head 12 except the inner bore 28 is modified to accommodate saddle 144 and modular clip 146. The saddle 144 may be the same or similar to saddle 90. The tulip head 142 and saddle 144 have elliptical bores 116 and profiles 114 respectively sized so that the saddle 144 can be assembled to the tulip head 142 and not rotate out of alignment. Grooves 148, 150 in the tulip head 142 are sized to accept the modular clip 146. The grooves 148, 150 may have a tapered or partially spherical profile to accommodate the outer profile of the modular clip 146. The modular clip 146 may include a smooth split ring 152 with a gap or cut 154 allowing the clip 146 to be expanded and slipped over the head 70 of the bone fastener 14. The cut 154 may be slanted or angled, forming an angled cut that is not perpendicular to the clip 146. The angled cut 154 permits the clip 146 to expand, and to facilitate assembly. The clip 146 is receivable in lower groove 148, which may be a spherical recess to allow the clip 146 to angle. The larger upper groove 150 is larger in diameter than the lower groove 148 and is sized to allow for the clip 146 to expand into when inserted over the bone screw 14. The clip 146 may include an upper ridge 156 or raised lip about the upper edge of the clip 146. The upper ridge 156 on the modular clip 146 limits the angulation of the clip 146 in the tulip head 12. Assembly of the modular head 140 may be performed by first inserting the saddle 144 into the tulip head 142, followed by the modular clip 146. The modular clip 146 helps to retain the saddle 144 within the tulip head 142.

As best seen in FIGS. 7A-7D, assembly of the modular head assembly 140 to a bone screw 14 may be completed by positioning the modular head assembly 140 over the bone screw 14 and applying downward force onto the bone screw 14. In a first stage shown in FIG. 7A, the modular clip 146 is located in the lower groove 148 and the saddle 144 is seated low in bore 28. The modular head 140 is positioned over the bone screw 14. In a second stage shown in FIG. 7B, a downward force is applied to the modular head 140 and onto the head 70 of the bone fastener 14, thereby pushing the clip 146 and saddle 144 upward. The clip 146 is aligned with the upper groove 150 and the saddle 144 is seated higher in bore 28. In a third stage shown in FIG. 7C, with continued downward force onto bone fastener 14, the modular clip 146 expands into groove 150 allowing the head 70 of the bone screw 14 past the modular clip 146. In a fourth stage shown in FIG. 7D, the modular clip 146 snaps around the head 70 of the bone screw 14 and falls back into the lower groove 148, retaining the bone screw 14 within the modular head 140.

Once installed into the patient, the spinal rod 18 is positioned into the rod slot 30 of tulip 142 and into the rod seat 110 in the top of the saddle 144. The locking cap 16 is threaded 34, 56 into the top of the tulip 142. Tightening of the locking cap 16 compresses the spinal rod 18 into the rod seat 110 of the saddle 144 preventing rotation and translation about the rod 18. Force is transmitted through the saddle 144, compressing spherical head 70 of the bone screw 14 into the spherical pocket 109 of the saddle 144. This locks the polyaxial motion of the tulip head 142 relative to the bone fastener 14.

Figures 8A, 8B:
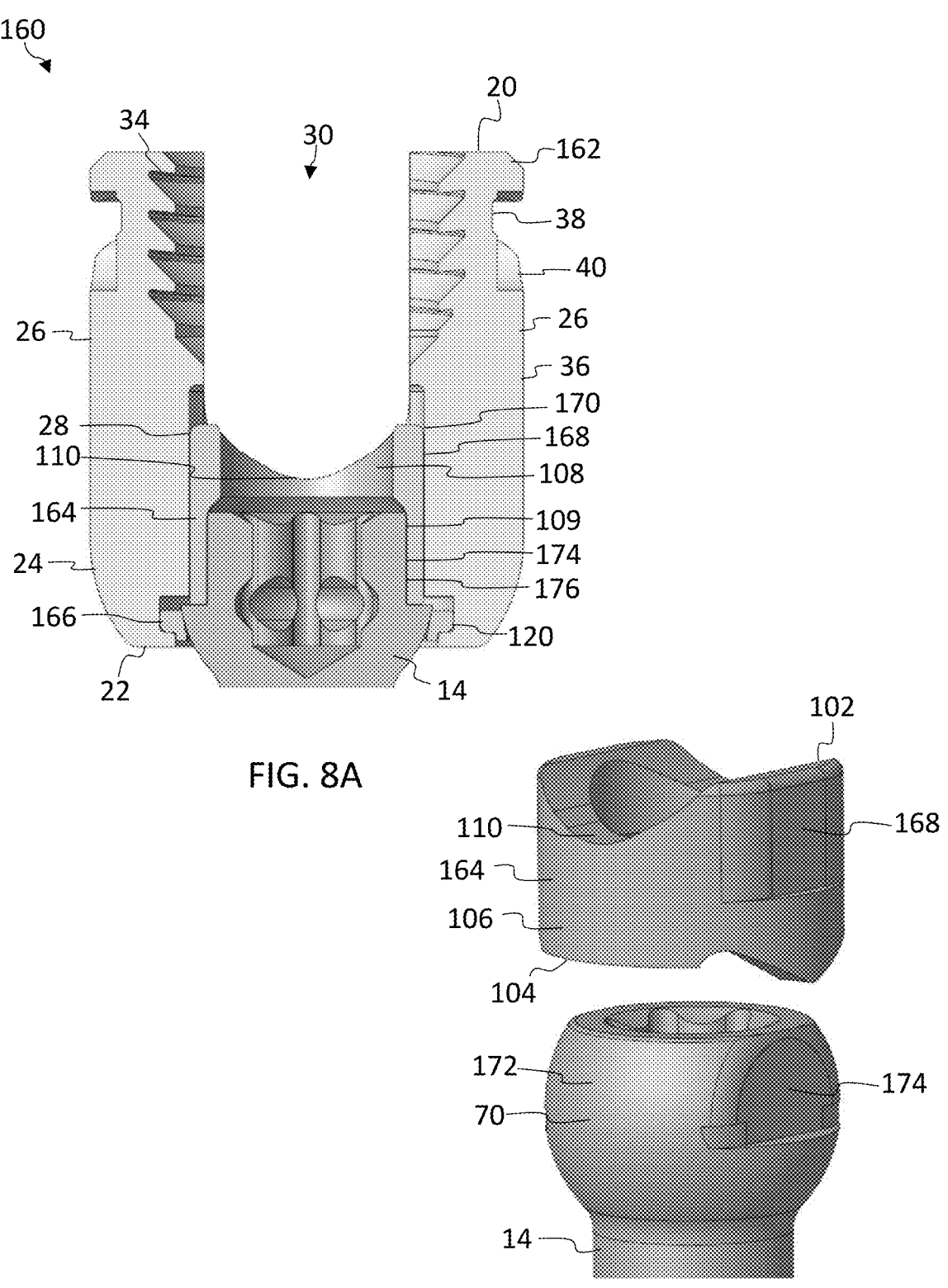
FIGS. 8A-8B show a cross-sectional view of a uniplanar screw assembly and an exploded view of a uniplanar saddle and screw head according to one embodiment.

Turning now to FIGS. 8A-8B, a uniplanar screw head assembly 160 is shown according to one embodiment. The uniplanar tulip assembly 160 functions similar to the polyaxial assembly 10 but restrict the sideways angulation of the tulip head 162 and rotation about the axis of the bone screw 14. In this embodiment, the uniplanar pedicle screw assembly 160 allows for angulation in one direction but not the other directions. The uniplanar movement allows the application of forces through the screw rigidly for correction of spinal deformities. Similar to the polyaxial screw assembly 10, the uniplanar tulip assembly 160 includes tulip head 162, saddle 164, and clip 166, but the friction ring 94 is omitted. The uniplanar tulip assembly 160 permits the user to manipulate the tulip head 162 and apply corrective forces to the bone screw 14.

Tulip head 162 has many of the same features as tulips 12, 142 including opposed arms 26 defining U-shaped rod slot 30 configured to accept the rod 18, interior threaded portions 34 for engaging the locking cap 16, and one or more outer engagement features 38, 40, 42, 44 for interaction with mating instruments. The tulip head 162 provides for benefits similar to the polyaxial screw assemblies 10, 140, which enables re-use of existing tooling and fewer complicated manufacturing steps. The uniplanar tulip assembly 160 allows for movement or adjustment of the bone fastener 14 relative to the tulip head 162 along a single plane. The bone fastener 14 may be oriented along one plane of motion for precise alignment of the uniplanar tulip assembly 160.

The head component 142 houses the saddle 164 and clip 166. The saddle 164 includes upper seat 110 for receiving the rod 18 and a bottom surface for receiving the top of the screw head 70. Opposite sides of the saddle 164 have flat surfaces 168 configured to mate with corresponding flat surfaces 170 inside the tulip head 162. The flats 170 in the tulip head 162 may be positioned inside each arm 26 below the threaded portion 34. Outer flats 168 on the saddle 164 engage internal flat surfaces 170 in the tulip head 162 to prevent rotation. The mating flat surfaces 168, 170 on the outside of the saddle 164 and inside head 162 restrict the saddle 164 from rotating and angling within the tulip 162.

In this embodiment, the screw head 70 includes spherical surfaces 172 in the direction of motion (e.g., aligned with the rod 18), and flat opposing surfaces 174 parallel to the direction of angulation, which restrict angulation in the perpendicular direction. The flat surfaces 174 of the head 70 align with corresponding flat surfaces 176 inside the saddle 164. Flats 174 on the spherical head 70 of the bone screw 14 engage internal flat surfaces 176 in the saddle 164 to prevent rotation between these components. These flat surfaces 174, 176 restrict rotation of the bone screw 14 about the central axis of the tulip 162. In particular, the flats 174, 176 may restrict medial-lateral angulation for uniplanar functionality.

The clip 166 may be the same or similar to clip 92. Clip 166 may include a loop, ring, split-ring, snap ring, or other suitable retaining ring. In an exemplary embodiment, the clip 166 is a split retaining clip. The clip 166 rests in groove 120 in the base of the tulip 162 and is configured to fit around the bottom of the screw head 70. The clip component

166 retains the bone screw 14 within the assembly 160 and resists compressive force exerted down on the bone screw 14.

The tulip head 162 pivots on the screw head 70 in one direction (e.g., medial-lateral angulation). It will be appreciated that the tulip head 162 is permitted to pivot either along the rod slot 30 or perpendicular to the rod slot 30 depending on the configuration of the components. The orientation of the flat surfaces 174, 176 parallel to the rod slot 30 results in a uniplanar screw able to control coronal and axial corrections. The orientation of these surfaces 174, 176 perpendicular to the rod slot 30 results in a uniplanar fracture screw able to control sagittal corrections commonly used in correcting traumatic fractures.

When the saddle 164 is in an upward position, the saddle 164 is able to accept the screw head 70. As shown in FIG. 8A, when the saddle 164 is then translated downward within the tulip head 162, the screw head 70 cannot be released. The saddle 164 compresses against the head 70 of the screw 14 when threaded locking cap 16 is threaded downwardly onto the spinal rod 18, thereby pushing against the saddle 164. The saddle 164 applies compressive force to the bone screw 14 and restricts its angulation when the rod 18 is tightened to the implant 160 with the locking cap 16. In this locked position, the uniplanar screw assembly 160 is locked in place, thereby restricting motion and locking the uniplanar motion of the tulip head 162 relative to the bone fastener 14.

Turning now to FIGS. 9A-9B, a sacral-alar-iliac (S2AI) screw head assembly 180 is shown according to one embodiment. Similar to the polyaxial screw assembly 10, the S2AI assembly 180 includes tulip head 182, saddle 184, and clip 186, but the friction ring 94 is omitted. The S2AI assembly 180 is configured to enter at the second sacral bone (S2), pass through the alar region of the sacrum, and extend into the ilium (part of the hip bone) to provide pelvic fixation. The S2AI tulip assembly 180 functions similar to the polyaxial screw assembly 10 but is configured such that the angulation is preferred in one direction. To accomplish this, the bottom surface 22 of the tulip 182 and clip 186 may be provided at an angle in the medial/lateral direction with respect to the central axis of the tulip 182. The purpose of the preferred angle is to accommodate the S2AI trajectory in the pelvis, which commonly is at a more extreme and predictable angle when compared to standard pedicle screw trajectories. As this screw assembly 180 may be used in the pelvis which naturally comes with higher intraoperative and postoperative forces, the tulip outer diameter 188 may be enlarged in the middle portion to reduce splay. The screw shank 72 may also be outfitted with a larger diameter 190 for neck 74 and bigger drive recess 80 to bolster strength.

Tulip head 182 has many of the same features as tulip 12 including opposed arms 26 defining U-shaped rod slot 30 configured to accept the spinal rod 18, interior threaded portions 34 for engaging the locking cap 16, and one or more outer engagement features 38, 40, 42, 44 for interaction with mating instruments. In this embodiment, the base 24 of the tulip head 182 is offset or angled relative to the arms 26. The bottom surface 22 of the tulip head 182, where it contacts with bone, may be sloped or angled to align with the patient's natural anatomy. Due to the extreme angulation of the S2AI trajectory, the sloped bottom surface 22 may provide for a flush fit against the bone surface, minimizing any potential for soft tissue irritation. The internal groove 120 is also defined at an angle or slope, which mirrors the bottom surface 22. The internal groove 120 is configured to house clip 186 at the same angle or slope around the head 70 of the bone fastener 14. The clip 186 and saddle 184 may be the same or similar to those found in the polyaxial assembly 10.

When the saddle 184 is in an upward position, the saddle 184 is able to accept the screw head 70 and the screw 14 is permitted to rotate or angulate, for example, in the medial/lateral direction. When threaded locking cap 16 is threaded downwardly onto the spinal rod 18, the saddle 184 is pushed downward compressing against the head 70 of the screw 14. The screw head 70 is then retained and locked in position in the tulip assembly 180. In this locked position, the S2AI assembly 180 is fixed in position, thereby rigidly securing the construct.

Figure 10:
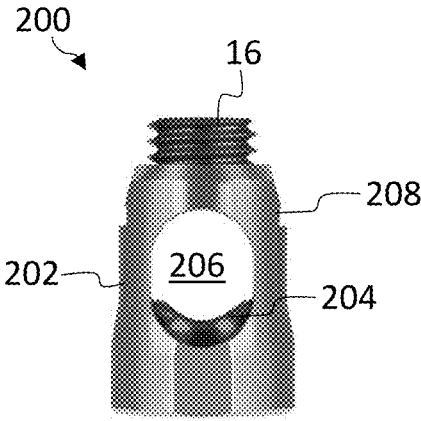
FIG. 10 shows a closed head connector according to one embodiment.

Turning now to FIG. 10, a closed head connector 200 is shown according to one embodiment. In some cases, it may be desirable to replace one of the tulip heads 12, 142, 162, 182 with the closed head connector 200. The closed head connector 200 includes closed head 202, saddle 204, optional retaining clip, such as clip 92, and optional friction ring, such as ring 94. The closed head connector 200 may be suitable for S2AI screws or other applications where an enclosed rod slot 206 is desired instead of an open rod slot 30. The enclosed rod slot 206 prevents outward splaying of the screw head for additional stability and strength. The instrument engagement features 38, 40, 42 from the tulip head 12 may be omitted, but notches 208 may be provided on opposite sides of the head 202 for connection to an instrument. Otherwise, this embodiment may be equivalent to S2AI assembly 180, for example.

The closed head connector 200 may include closed head body 202 for receiving the spinal rod 18 with threaded locking cap 16 and saddle 204 mounted therein. The closed head body 202 may have a generally cylindrical or conical body that flares or tapers outward toward its base. The body 202 of the closed head connector 200 may define through passage or rod slot 206 therethrough, which is sized and shaped to receive spinal rod 18. The enclosed rod slot 206 may be elongated vertically to have a length greater than its width to allow for some translation of the rod 18 in the passage 206 before the locking cap 16 is tightened. In the same manner as S2AI assembly 180, the bone fastener 14 may be inserted into the bottom of the connector body 202 and may angulate relative to the closed head 200. When the threaded locking cap 16 is tightened, the cap 16 presses down onto the spinal rod 18 securing it within the closed head connector 200, which presses onto saddle 204, thereby rigidly locking the position of the bone fastener 14 relative to the closed head connector 200.

Figure 11:
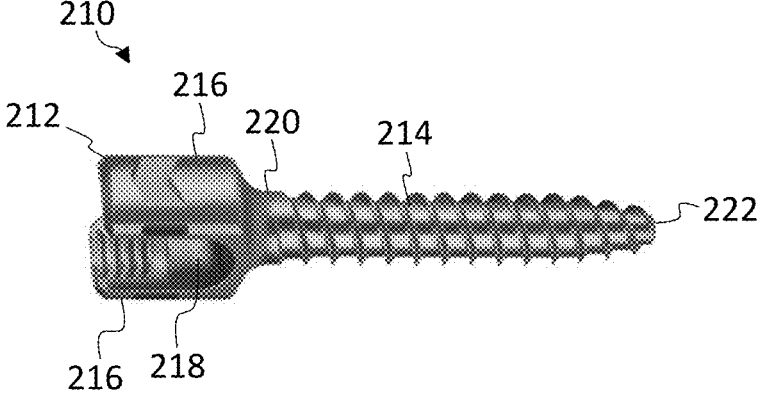
FIG. 11 shows a monoaxial screw according to one embodiment.

Turning now to FIG. 11, a monoaxial bone screw 210 is shown according to one embodiment. The monoaxial screw 210 may be a unitary construction with tulip head 212 and bone screw shaft 214 forming one integral component. This provides complete rigidity between the screw head 212 and screw 214, allowing the user more control over correction of the spine at the cost of the angulation of the screw head. The monoaxial screw 210 includes tulip head 212 having two arms 216 defining rod slot 218 therebetween. The tulip head 212 connects to threaded shaft 214 at neck 220 and extends to distal tip 222. The distal tip 222 may be blunt or otherwise configured to engage bone. The monoaxial bone screw 210 allows for movement or attachment along a single axis. Once the screw 210 is anchored into the bone, the spinal rod 18 may be positioned in one direction, perpendicular to the screw. Once the spinal rod 18 is seated in the rod slot 218, the rod 18 may be secured with a threaded locking cap 16.

Figure 12:
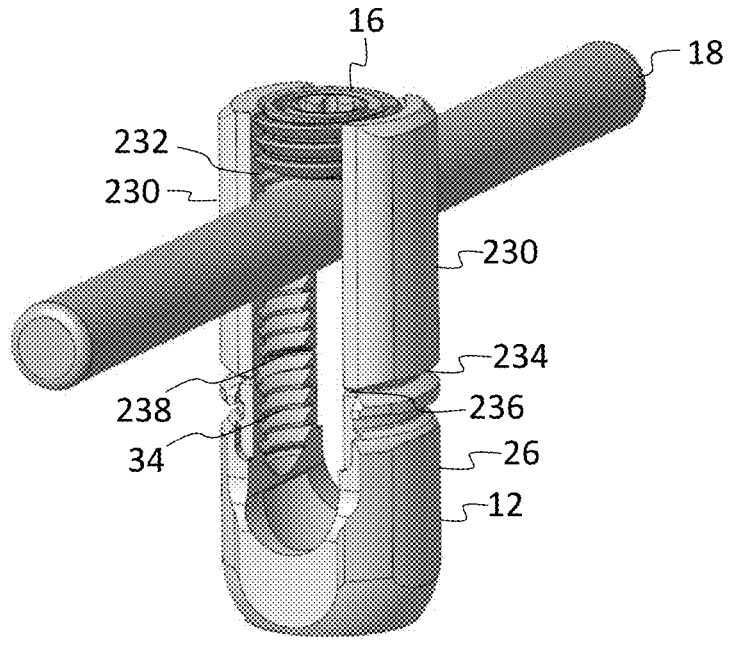
FIG. 12 shows removable extensions for reducing a spinal rod into the tulip head according to one embodiment.

Turning now to FIG. 12, the tulip head 12 may include removable extensions 230, which provide a pathway for secure implantation of the spinal rod 18 while minimizing tissue dissection. Extensions 230 to the tulip head 12 may be included such that tightening of the locking cap 16 reduces the rod 18 into the screw head. Once fully reduced, the extensions 230 may be broken off of the screw head 12 with the tulip head 12 remaining behind. Extensions 230 may extend vertically from the top 46 of each arm 26, thereby extending the arms 26 to create integrated extended tabs. The inner surfaces of each extension 230 may include threaded portions 232, which continue threaded portion 34 for engaging the locking cap 16. In this manner, the locking cap 16 may be threaded down extensions 230 and into the tulip head 12. Circumferential 234, straight 236, and/or internal 238 grooves may be included to induce the extensions 230 to be broken off cleanly at a desired height. The circumferential groove 234 may extend around an outer perimeter defining the border between the extension 230 and the tulip arm 26. The internal grooves 238 may follow the circumferential groove 232 along the inside 32 of each arm 26. The straight grooves 236 may connect the inner and outer grooves 232, 238 along the sides of each arm 26 and extension 230. After the rod 18 is seated between extensions 230, the threaded locking cap 16 may be tightened down extensions 230 and into tulip head 12. Once the rod 18 is fully seated in tulip head 12, the extensions 230 may be removed. The breakaway extensions 230 may help to simplify the procedure and reduce operating time.

Figure 13A:
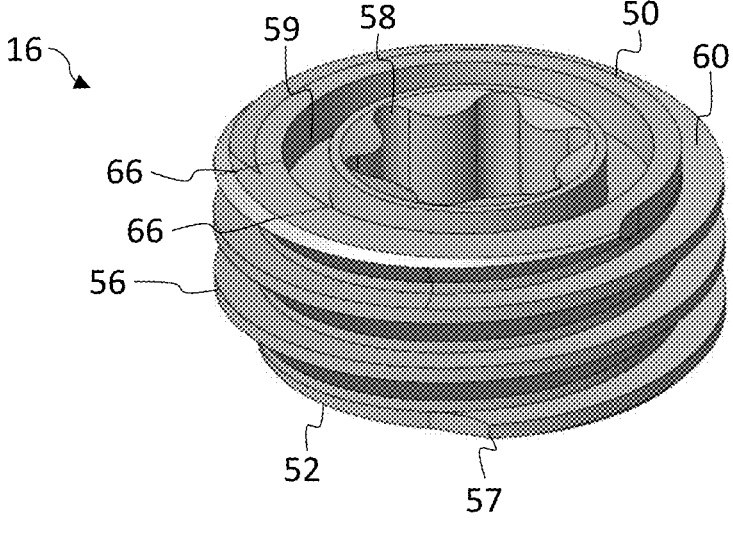
FIGS. 13A-13C show a locking cap with a circumferential groove for engaging with a mating instrument according to one embodiment.
Figure 13B:
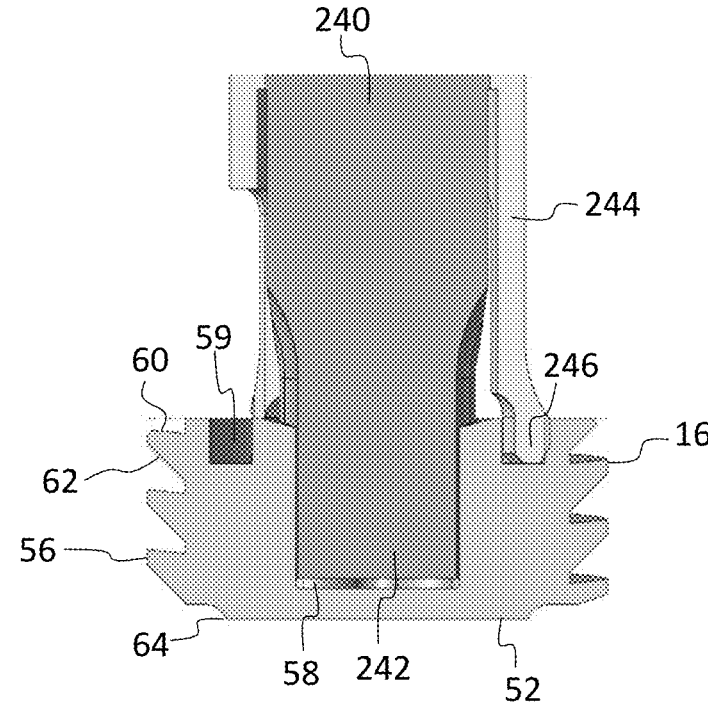
Figure 13C:
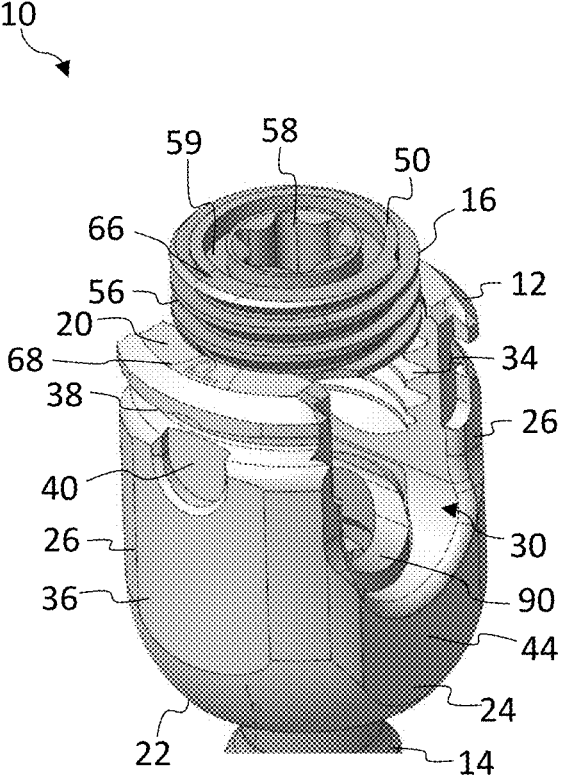

Turning now to FIG. 13A-13C, locking cap 16 is shown in more detail. The locking cap 16 has one or more external helical threads 56 which mate with thread 34 defined in the arms 26 of the screw head 12 (or other heads 142, 162, 182). The thread 56 has a thread start 57, which initiates at the bottom 52 of the cap 16 and then continues to spiral up the cap 16. A best seen in FIG. 13B, drive recess 58 is configured to mate with insertion and tightening instruments, such as driver 240. The drive recess 58 is an indentation or slot (e.g., a hexalobular Torx recess) in the top 50 of the locking cap 16 shaped to receive the matching end of the driver 240. The driver 240 includes a driver tip 242 corresponding to the drive recess 58 to apply a torque to the locking cap 16 to tighten or loosen the cap 16 as needed.

As best seen in FIG. 13A, a circular groove 59 may be provided in the top surface 50 of the locking cap 16. The groove 59 may be a channel that encircles and surrounds the drive recess 58, at a depth shallower than the depth of drive recess 58. The driver 240 includes one or more prongs 244 configured to engage with the groove 59 to retain the cap 16. The prong(s) 244 may form part of a sleeve around the driver shaft. Prong(s) 244 may include a distal tip 246 that projects distally and into the groove 59 to secure the driver 240 to the implant 10. Depending on the configuration of the driver assembly 240, the driver shaft may be permitted to rotate when the prong 244 is engaged or the prong 244 may be engaged to prevent rotation. The bottom 52 of the locking cap 16 may include a shoulder 64, which acts as a contacting surface for the rod 18, to prevent the rod 18 from contacting the threads 56 of the locking cap 16. Once the locking cap 16 is fully seated in the tulip head 12, the locking cap 16 secures the spinal rod 18 therein and locks the implant.

As best seen in FIG. 13C, one or more markings 66 may be provided on the top 50 of the locking cap 16 and one or more markings 68 may be provided on the top 20 of the arm 26 of the tulip head 12. The markings 66, 68 may include indicators or etchings, such as a pair of etched lines, or other suitable markings. The markings 66 on the locking cap 16 and markings 68 on the screw head 10 may be timed to the thread start 57 so that the user may visually position the locking cap 16 and easily catch the thread 56 when inserted into the tulip head 12. The locking cap 16 may be made of a titanium alloy (e.g., titanium-aluminum-vanadium), which is hardened to prevent the hard tulip 12 (e.g., cobalt-chromium) from cutting the surface of the locking cap 16 and generating debris. It will be appreciated, however, that any suitable materials may be used for the components.

Figure 14A:
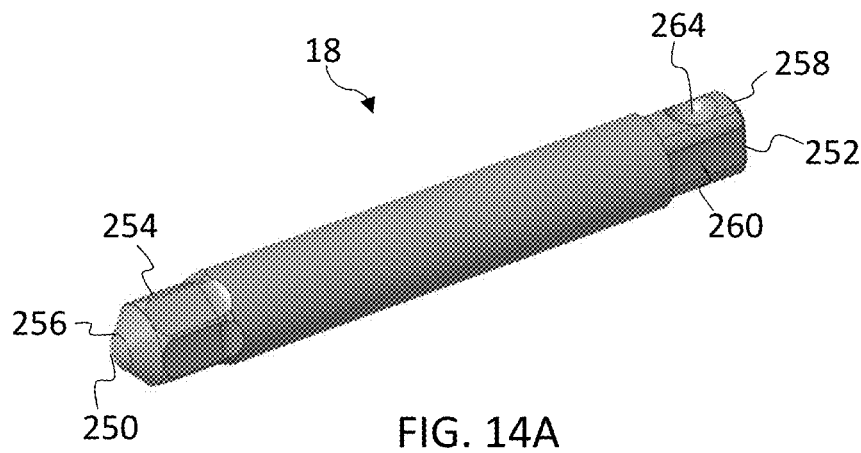
FIGS. 14A-14B show a spinal rod having a hex end for rotation of the rod and an obround end for attachment to a rod holding instrument according to one embodiment.
Figure 14B:
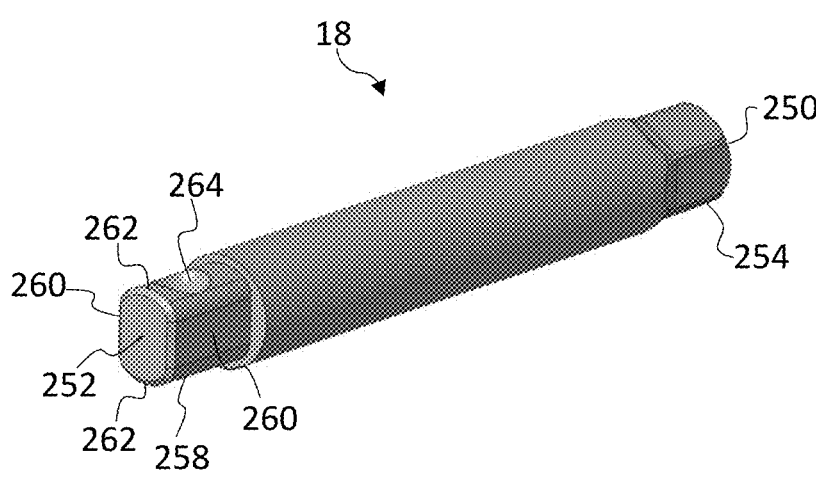

Turning now to FIGS. 14A-14B, the spinal rods 18 may be provided in a variety of types and sizes. The rods 18 may be straight or curved to fit the curvature of the spine. Surgeons may also contour rods 18 intraoperatively to meet the patient's alignment. Tapered rods may be offered in varying smaller diameters for connection to small stature thoracolumbar (e.g., 4.75 mm) or cervical (e.g., 3.5 mm) screw systems. The rods 18 may be substantially circular or cylindrical in shape along its length or may be otherwise configured.

In some cases, minimally invasive surgery (MIS) rods 18 may be used in the procedure, which allows for minimally invasive rod delivery without the need for extra incisions. Each MIS spinal rod 18 may have a body extending from a first end 250 to a second end 252 along its length. Rods 18 may be offered with varying ends 250, 252 for attachment of manipulation instruments, such as rod holder instrument 540 shown in FIGS. 34A-34D, which may insert and manipulate the MIS rods into the desired position. As best seen in FIG. 14A, hex-ended rods may be offered with a hex interface 254 on one end 250. The hex interface 254 may include a six-sided hexagonal cross-section with six flat surfaces that ensure a secure grip and efficient transfer of turning force and reducing the risk of stripping. The hex interface 254 may be used for attachment of a wrench, for example, so that the user may rotate the rod 18 to perform correction by global derotation. Although a hex interface 254 is shown, it will be appreciated that other suitable cross-sections may also be used. MIS rods 18 may also be offered with a tapered tip 256 for passage through soft tissue. The tapered tip 256 may taper or narrow from the hex interface 254, for example, in a conical shape, resulting in a blunt or rounded end 250. Longer MIS rods 18 may include hex 254 adjacent to the tip to allow the user to engage a wrench for correction. Shorter MIS rods 18 may omit the hex feature.

A rod gripping interface 258 may be located on the opposite end 252 of the rod 18, which is configured to mate with a rod holding instrument, such as rod holder instrument 540. For example, the rod gripping interface 258 may include an oval or obround cross-section. In one embodiment, the obround interface 258 includes opposed flats 260 with rounded ends 262. The flats 260 allow for the rod 18 to key with the instrument and prevent rotation about the rod axis. One or more divots 264 may be provided on the rounded ends 262 of the obround interface 258. For example, spherical divots 264 may be defined into the top and bottom of the MIS rod gripping interface 258 to prevent disengagement from the rod holder 540.

Figure 15:
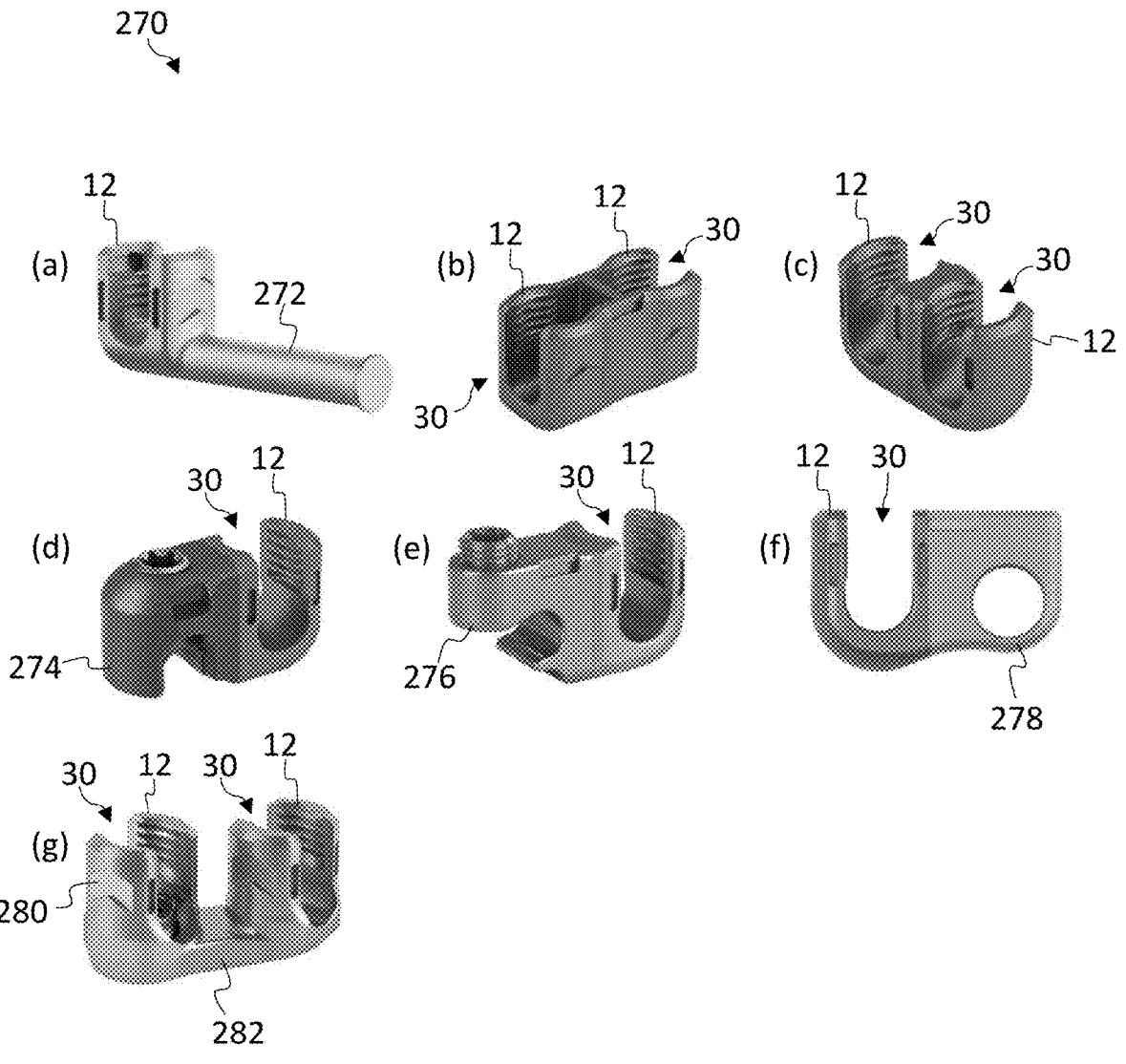
FIG. 15 shows several examples of connectors for connecting two spinal rods together.

Turning now to FIG. 15, examples of connectors 270 are shown for attaching one spinal rod 18 to another spinal rod 18 in the construct. The rods 18 may be interconnected with one or more connectors 270, for example, in a single given surgery, such as a scoliosis operation, or at a later surgery, for example, in a revision surgery. In some cases, the connectors 270 may be used to revise and extend thoracolumbar constructs using a minimally invasive approach.

Any of the features of tulip head 12 may be included in any of these types of connectors 270. These connectors 270 may include (a) a tulip head 12 with a laterally extending rod portion 272, (b) a pair tulip heads 12 having inline rod slots

30, (c) a pair of tulip heads 12 having offset or parallel rod slots 30; (d) a tulip head 12 with an integral top loading connector portion 274; (e) a tulip head 12 with an integral open connector portion 276; (f) a tulip head 12 with a closed connector portion 278; or (g) a pair of tulip heads 12 connected with a bridging element 282 where one tulip 12 functions as a modular head 280 to integrate a second head into a modular screw and eliminate a separate component. The bridging element 282 separates the head portions 12 such that instruments which fit around the screw heads may engage the instrument engagement features. Double head screw connectors 270 may provide for strength and stability in procedures that require additional rods 18 for rigidity.

Figure 16:
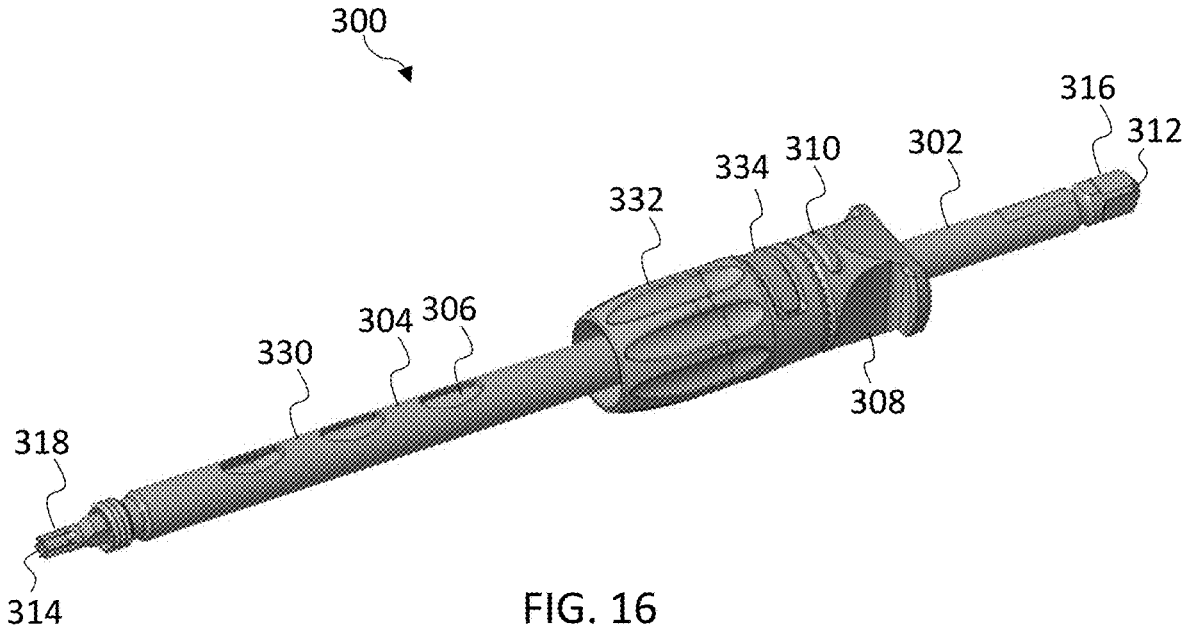
FIG. 16 shows an assembled screwdriver including an inner shaft assembly and an outer sleeve assembly for inserting bone screws according to one embodiment.

Turning now to FIGS. 16-20B, screwdrivers 300 or other instruments may be used for placement of screws 14 into vertebrae under fluoroscopic, image guided, or robotic guided approaches. The screwdrivers 300 may be used to drive bone screws 14 into bone. The screws 14 may be placed alone or in combination with the tulip assembly 10. The screwdrivers 300 may be offered in multiple versions, for example, for traditional, minimally invasive, modular, sacral-alar-iliac, robotic guidance, freehand navigated, and robotic navigated workflows. As shown in FIG. 16, the screwdrivers 300 may have a modular design including an inner shaft assembly 302 and an outer sleeve assembly 304, which when combined form the complete screwdriver 300. The inner shaft assembly 302 is used to transmit torque to the bone screw 14, while the outer sleeve assembly 304 provides a system to securely hold the bone screw 14 to the inner shaft assembly 302.

Figure 17A:
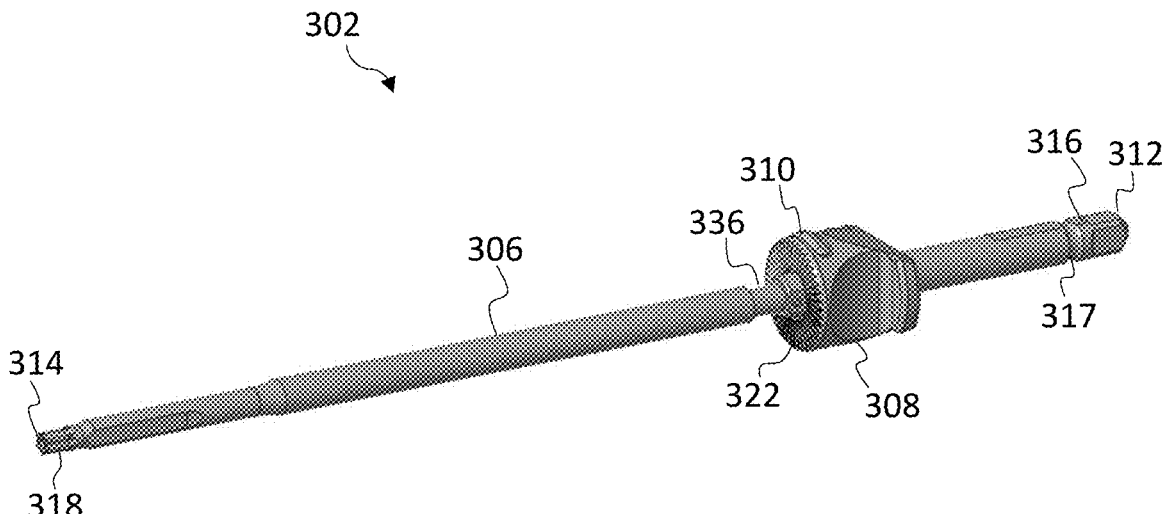
FIGS. 17A-17B show perspective and cross-sectional views, respectively, of the inner shaft assembly of the screwdriver according to one embodiment.
Figure 17B:
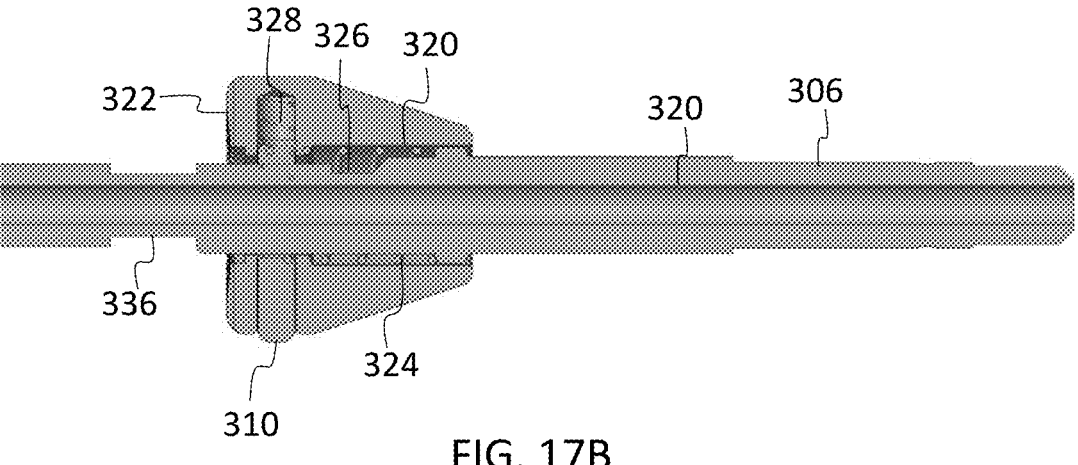
Figure 19A:
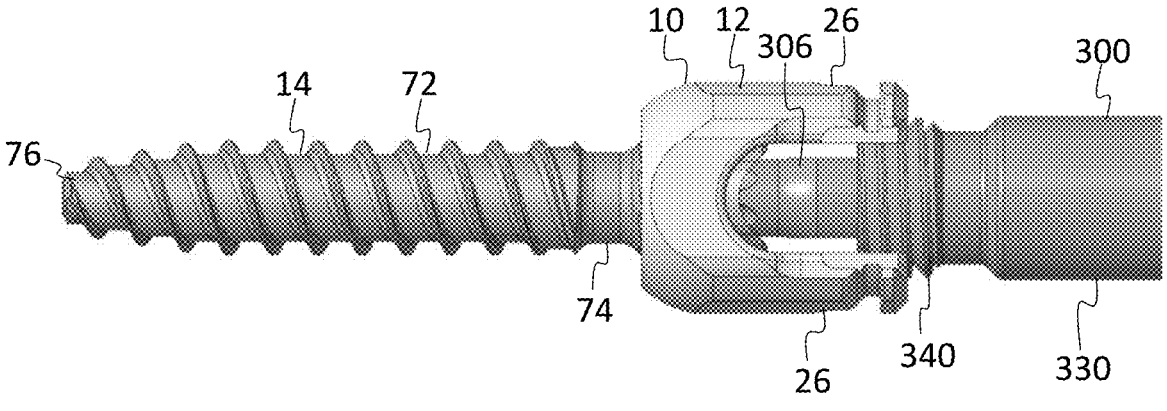
FIGS. 19A-19B show perspective and cross-sectional views, respectively, of the distal end of the screwdriver connected to a bone fastener and tulip assembly according to one embodiment.
Figure 19B:
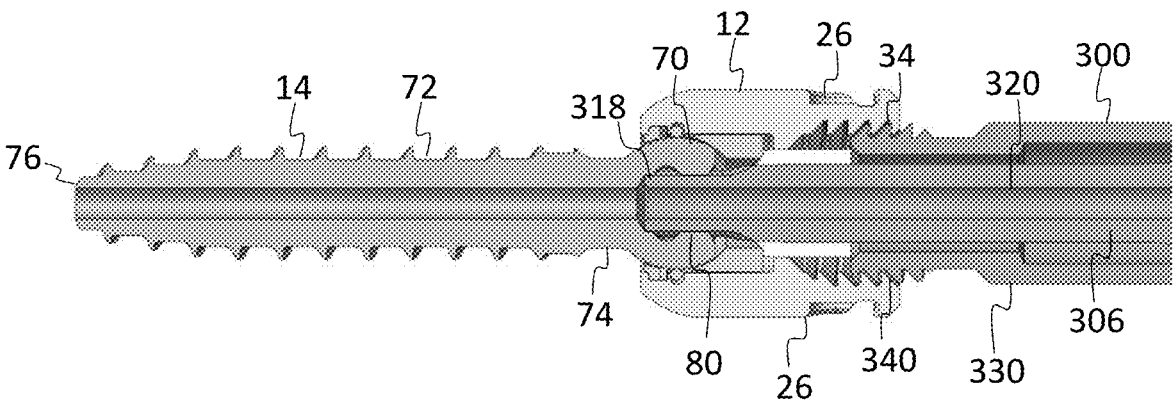

As best seen in FIGS. 17A-17B, the inner shaft assembly 302 includes an inner shaft 306, an outer sleeve rotation lock 308, and lock button 310. The inner shaft 306 extends from a proximal end 312 to a distal end 314 along a central tool axis. The proximal end 312 includes an attachment interface 316 configured to securely couple the inner shaft 306 to a handle or powered driver. The attachment interface 316 may include a handle interface with a circumferential groove 317 configured to secure a quick-connect handle, such as quick-connect assembly 406 shown in FIGS. 26A-26B. The distal end 314 includes a driver interface 318 or driver tip, which is configured to mate with the drive recess 80 of the bone screw 14. The inner shaft 306 may be cannulated 320, which may align with a cannulated screw 14 to accept a guide wire or K-wire (e.g., as shown in FIG. 19B).

The rotation lock 308 includes a body with a through opening 320 defined along the central tool axis. The inner shaft 306 is positionable through opening 320. The rotation lock 308 includes a distal-facing surface with radial teeth 322 defined therein. The teeth 322 may include sawtooth shaped teeth, which engage similarly shaped teeth 338 on the outer sleeve 330. The shape of the teeth 322 allow for rotation in the clockwise (tightening) direction, but not in the counterclockwise (loosening) direction, preventing unintended loosening of the outer sleeve 330 during use. The rotation lock 308 may be spring loaded 324 to maintain teeth engagement.

The lock button 310 is positioned through a transverse bore that intersects through opening 320. The lock button 310 may be aligned perpendicular to the inner shaft 306. The lock button 310 may also be spring loaded 328. The base of the button 310 is receivable in a notch 326 in shaft 306 when pulled back to hold the rotation lock 308 in an unlocked position. Depressing the lock button 310 causes re-engagement of the rotation lock 308, thereby returning the rotation lock 308 to a locked position.

Figure 18A:
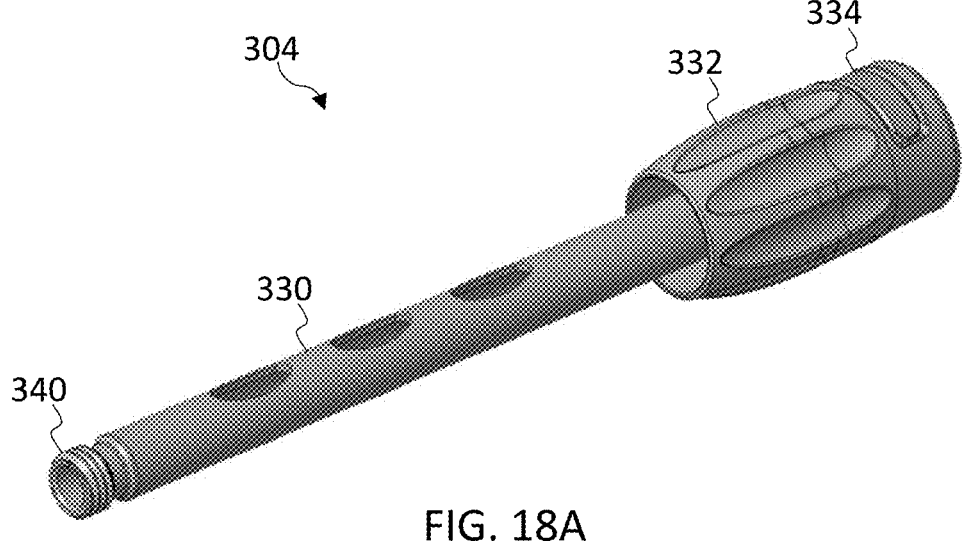
FIGS. 18A-18B show perspective views of the outer sleeve assembly of the screwdriver according to one embodiment.
Figure 18B:
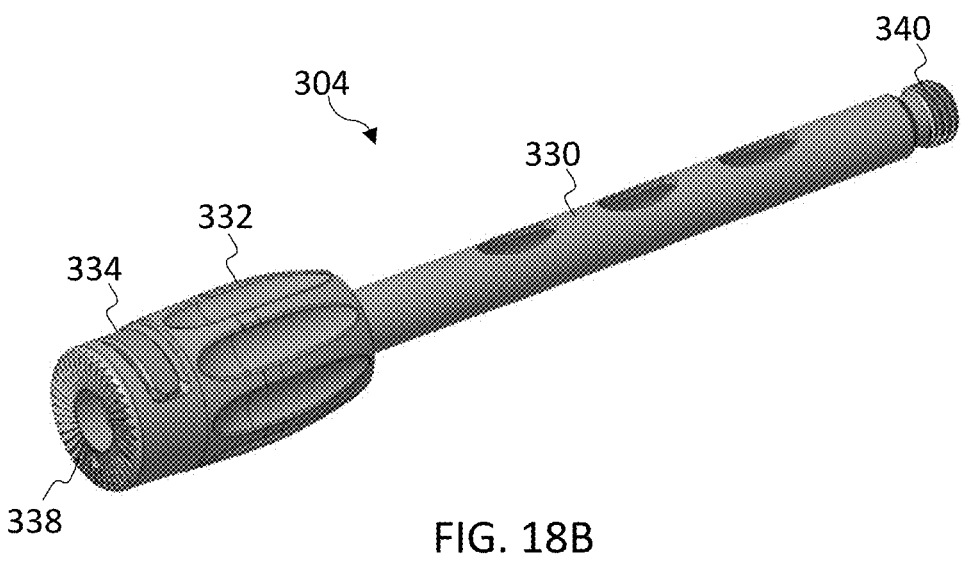

As best seen in FIGS. 18A-18B, the outer sleeve assembly 304 includes an outer sleeve 330 configured to receive the inner shaft 306, a barrel 332, and a button 334. The outer sleeve 330 includes a tubular or cylindrical body sized and dimensioned to receive the inner shaft 306. The outer sleeve 330 may define one or more transverse windows or openings to view the inner shaft 306. The outer sleeve 330 may be attached to the inner shaft 306 via spring-loaded release button 334, which engages with a groove 336 on the inner shaft 306. The groove 336 is located on the inner shaft 306 distal of the radial teeth 332 on the rotation lock 308. The outer sleeve 330 can be removed from the inner shaft 306 by depressing the release button 334.

The barrel 332 includes a proximal-facing surface with radial teeth 328 defined therein. The teeth 328 may include sawtooth shaped teeth, which engage similarly shaped teeth 322 on the rotation lock 308. The distal tip of the outer sleeve 330 may include external threads 340 configured to mate with internal threads 34 on the screw head 12 to retain the implant 10 to the instrument 300. As best seen in FIGS. 19A-19B, the outer sleeve 330 may be connected to the tulip head 12 via mating threads 34, 340. The driver tip 318 of the inner shaft 306 may be inserted into recess 80 to insert the tulip assembly 10 into bone.

Figure 20:
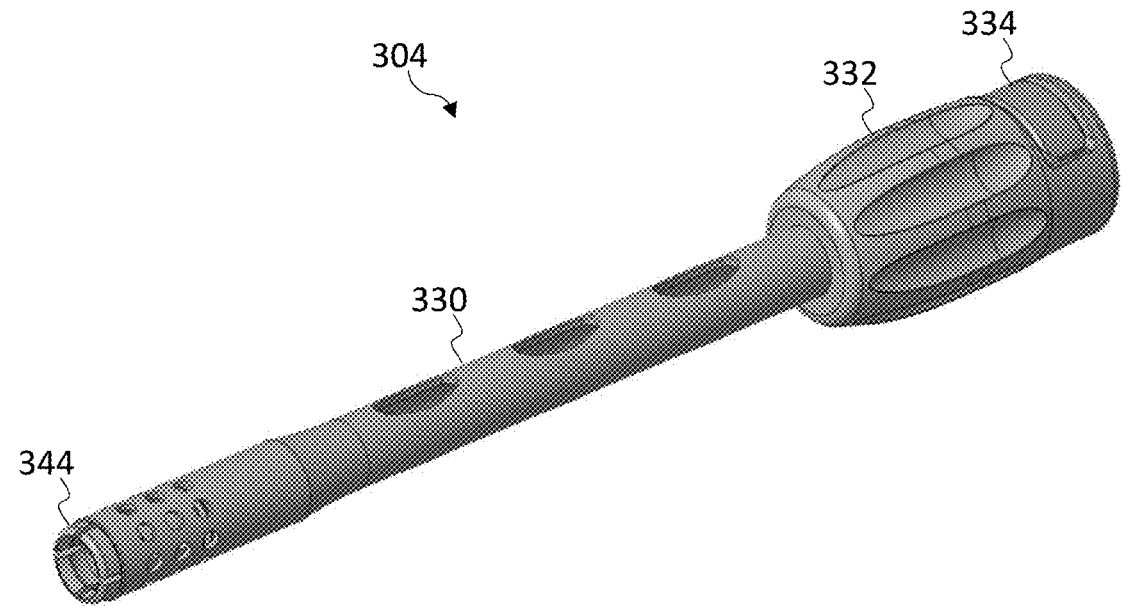
FIG. 20 shows an outer sleeve assembly with a collet according to one embodiment.

Turning now to FIG. 20, modular screwdrivers 300 may have a modified outer sleeve assembly 304 configured to interface with modular implants 140, where the screw 14 is first inserted into bone before the tulip assembly 142 is secured to the screw head 70. In one embodiment, the threads 340 on the outer sleeve 330 are replaced with a collet 344. The collet 344 may include a cylindrical body with longitudinal slits, which enhance the collet's flexibility, enabling it to tightly grip the inserted screw head 70 and release it smoothly when the collet 344 is loosened.

Figure 21A:
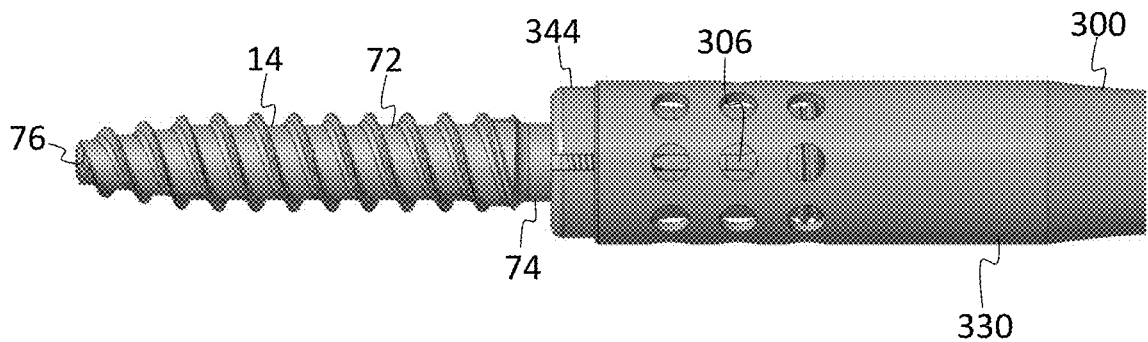
FIGS. 21A-21B show perspective and cross-sectional views, respectively, of the distal end of the screwdriver connected to a bone fastener with the collet according to one embodiment.
Figure 21B:
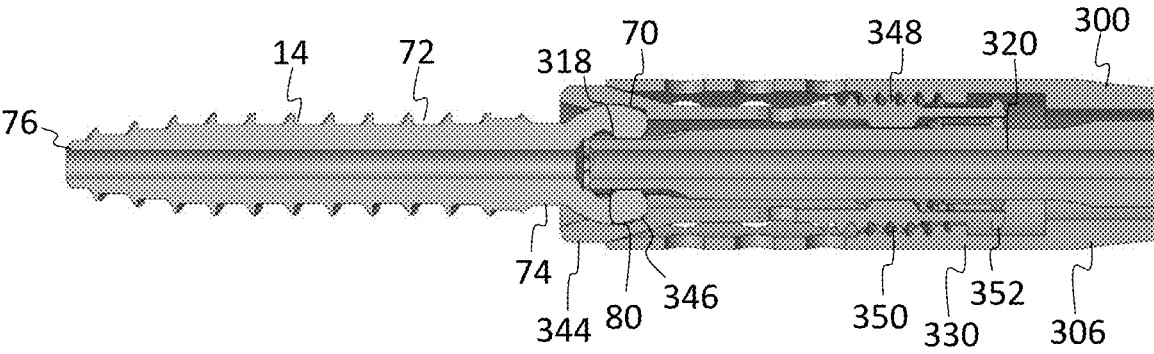

As best seen in FIG. 21B, the distal end of collet 344 defines an internal spherical pocket 346 configured to engage the spherical head 70 of a bone screw 14. The collet 344 is configured to compress and conform to the size of the spherical head 70 it is holding, thereby providing a secure grip. The collet 344 may include outer threads 348, which are configured to engage corresponding threads 350 on the inside of outer sleeve 330. The collet 344 may be retracted by rotating collet 344 back into outer sleeve 330, for example, by rotating inner shaft 306 or other suitable mechanism. Alternatively, the collet 344 may have a toothed interface, which incrementally secures the collet 344 when pulled back into outer sleeve 330. The outer sleeve 330 may have a tapered interior to tighten the collet 344 as it is retracted. It will be appreciated that any mechanism of drawing collet 344 into sleeve 330 may be used to cause the segments of the collet 344 to converge or clamp inward onto screw head 70. Stops 352 may be provided at the end of the collet 344, which fit in grooves inside the outer sleeve 330 to prevent the collet 344 from separating from the outer sleeve 330.

As best seen in FIGS. 21A-21B, the collet 344 clamps against the bone screw 14 when retracted into the outer sleeve 330, capturing the screw 14 on the tip of the instrument 300. The screw head 70 is positionable inside pocket 346 of collet 344. As the collet 344 is drawn back into outer sleeve 330, the collet 344 tightens around the screw head 70. Once secured to the instrument 300, the driver tip 318 at the tip of the inner shaft 306 mates with the drive recess 80 of the bone screw 14 to insert the screw 14 into bone. Once secured in bone, the instrument 300 is removed and the modular tulip assembly 142 may be attached to the screw head 70.

Figure 22A:
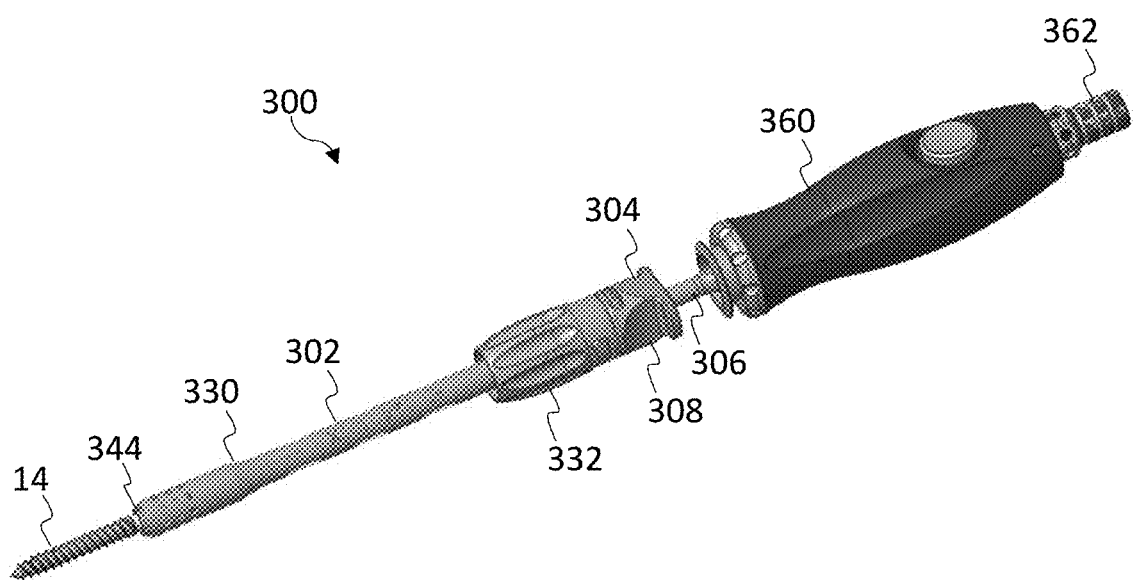
FIGS. 22A-22B show a single step screwdriver with a handle having a stylet retracted and advanced, respectively, according to one embodiment.
Figure 22B:
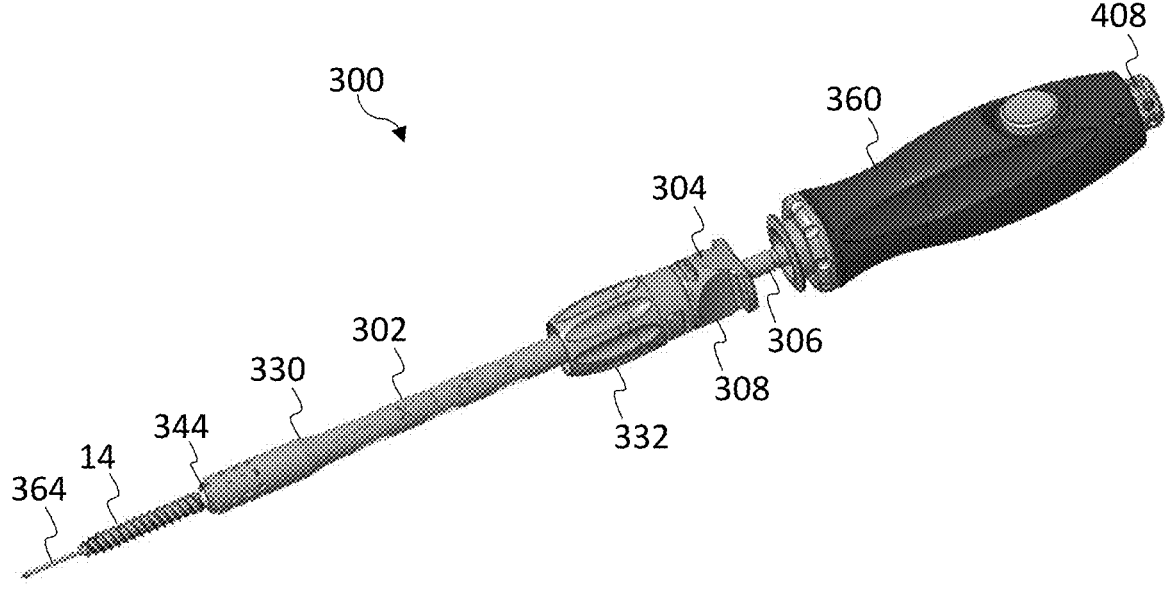

Turning now to FIGS. 22A-27B, a single step screwdriver 300 is shown according to one embodiment. The single step screwdriver 300 includes a handle assembly 360 attached to inner shaft 306 via attachment interface 316. The handle assembly 360 connects to screwdriver 300, which holds pedicle screw implant 14. The proximal end of the handle assembly 360 retains a stylet housing assembly 362, which holds a stylet 364. The stylet 364 is housed within handle assembly 360, extends through inner shaft 306, through screw 14, and may protrude from the screw 14. The stylet 364 may be linearly actuated a fixed distance relative to the pedicle screw 14. In FIG. 22A, the stylet 364 is shown in the retracted state. In FIG. 22B, the stylet 364 is shown fully advanced forward. The stylet 364 detachably mates with the stylet housing assembly 362, such that multiple lengths of stylet 364 may be used to accommodate for different screw lengths.

Figure 23:
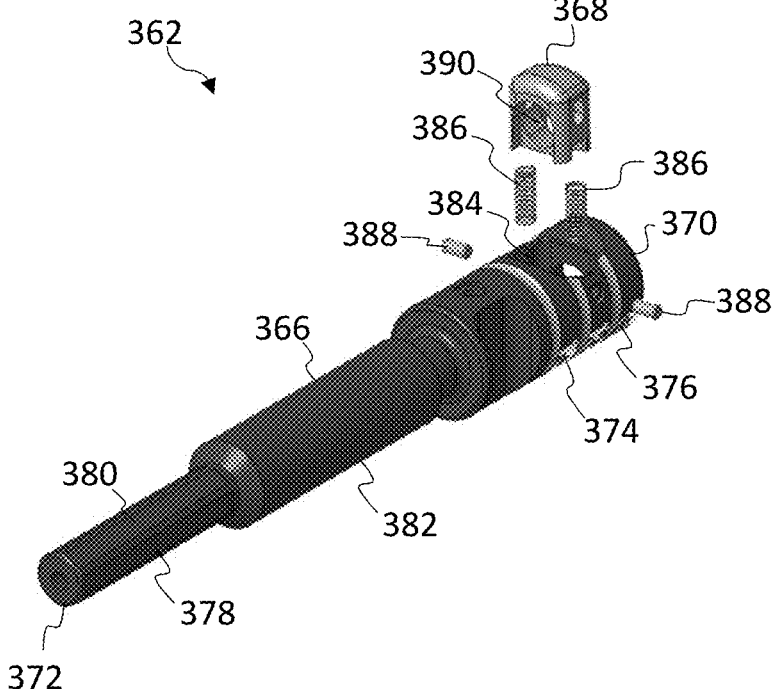
FIG. 23 shows an exploded view of the stylet housing assembly according to one embodiment.

As best seen in FIG. 23, the stylet housing assembly 362 includes a stylet housing body 366 and a spring-loaded button 368 for retaining the stylet 364. The stylet housing body 366 extends from a proximal end 370 to a distal end 372 along the central tool axis. The stylet housing 366 is cannulated along the central tool axis to retain the stylet 364 therein. The proximal end 370 of the stylet housing 366 includes a cylindrical indicator 374 with markings 376, which indicate the depth or position of the stylet 364. The markings 376 may include graduated etchings or other visual markings with lines, numbers, etc. to assist in accurate and safe positioning of the stylet 364 during the procedure. The distal end 372 of the stylet housing 366 includes a reduced diameter portion 378 receivable in the quick-connect housing assembly 404. The reduced diameter portion 378 may have longitudinal flats 380, for example, forming a hexagonal shape or other suitable shape for engaging the quick-connect housing assembly 404 and keeping the components rotationally coupled together. A central portion 382 of the stylet housing 366 between the indicator 374 and the reduced diameter portion 378 may include a cylindrical section configured to engage with a thread button 414 in the handle assembly 360. The central portion 382 may be threaded 383 (not shown in FIG. 23) to threadedly mate with corresponding threads 415 in the button 414 as described in more detail for FIGS. 25A-25B.

The stylet housing 366 defines a transverse bore 384 configured to receive the button 368. The button 368 may be positioned generally perpendicular to the stylet 364. The button 368 is spring loaded, for example, via two springs 386 and secured in the indicator 374 via pins 388. The button 368 defines a bore 390, which is configured to receive the stylet 364. The stylet 364 snaps into the handle assembly 360 via spring loaded button 366 of the stylet housing 362, which mates with a groove on the proximal end of the stylet 364. In this manner, the stylet housing 362 retains one end of stylet 364 and is configured to translate the stylet 364 along the central tool axis.

Figure 24A:
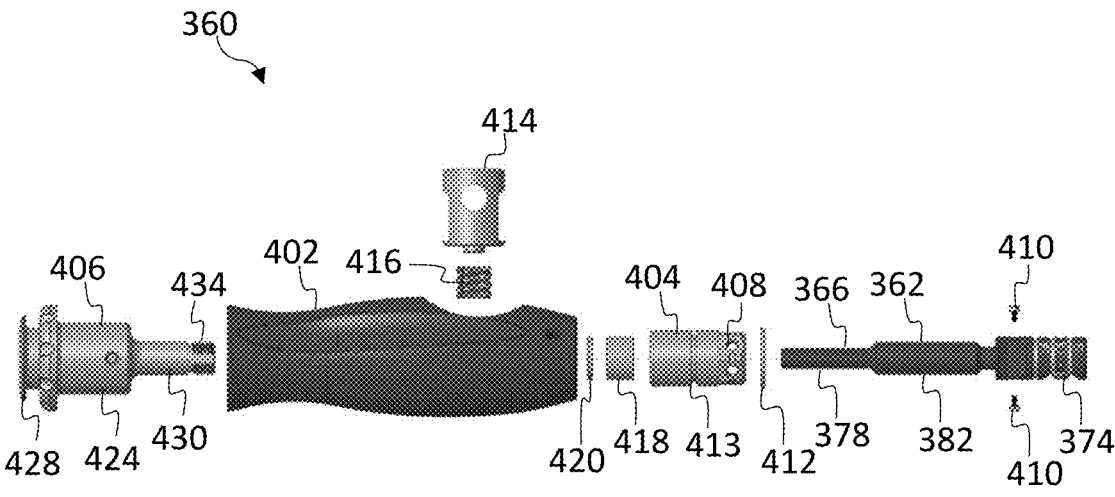
FIGS. 24A-24B show exploded views of the handle assembly and quick-connect assembly according to one embodiment.

Turning now to FIG. 24A, an exploded view of handle assembly 360 is shown. The handle assembly 360 includes a handle grip 402 configured to receive a sheath 404 at its proximal end for securing stylet housing assembly 362 and a quick-connect housing assembly 406 at its distal end for connecting to inner shaft 306 of the screwdriver 300. The handle grip 402 is configured to be held and turned by the user. The sheath 404 includes a tubular body configured to receive the stylet housing body 366. Openings 408 in sheath 404 are configured to receive one or more pins 410 to secure the stylet housing 366 to the sheath 404. A ring 412 is receivable in circumferential groove 413 defined into the outer surface of sheath 404 to secure the sheath 404 to the handle grip 402. A thread button 414 is positioned through a bore transverse to the central tool axis. The button 414 may be positioned generally perpendicular to the stylet assembly 362. The thread button 414 may be spring-loaded via spring 416. The quick-connect housing assembly 406 may be secured in the distal end of the handle grip 402 with a threaded ring 418 and washer 420, for example, or other suitable mechanism.

Figure 24B:
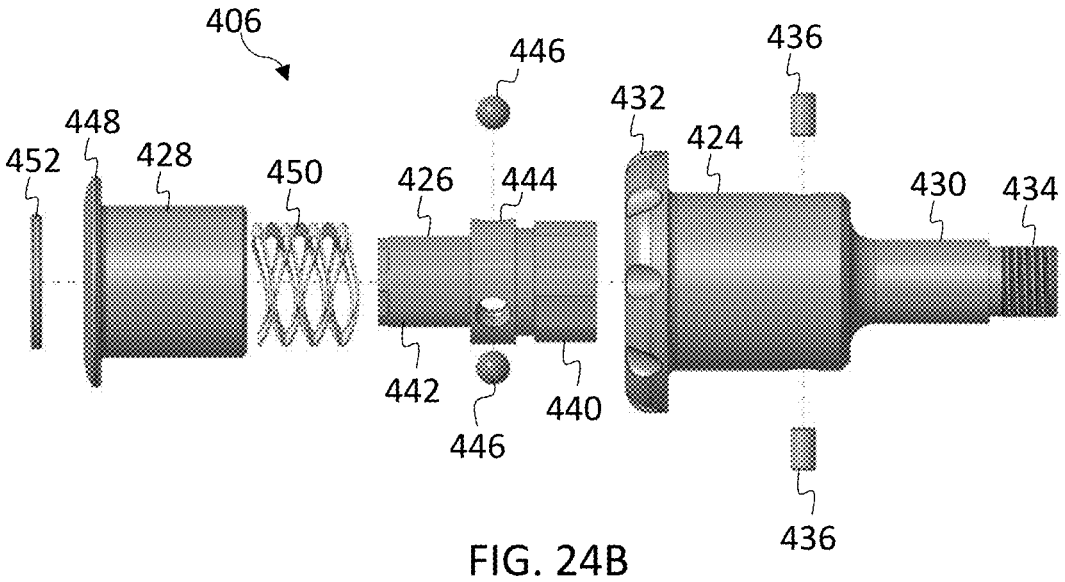

Turning now to FIG. 24B, an exploded view of the quick-connect housing assembly 406 is shown. The quick-connect housing assembly 406 includes a proximal casing 424, an inner casing 426, and a distal casing 428, which are all canulated along the central tool axis to allow the stylet 364 to pass therethrough. The proximal casing 424 may include a cylindrical body with a proximal stem 430 having a reduced diameter and a distal flange 432 having an enlarged diameter. The proximal-most end of the stem 430 may be externally threaded 434 to threadedly mate with the internally threaded ring 418. The distal flange 432 may include a radially projecting flange that fits against the distal end of the handle grip 402. One or more pins 436 may be used to secure the proximal casing 424 inside the handle grip 402. The inner casing 426 includes a body sized and dimensioned to fit within the proximal casing 424. The proximal section 440 of the inner casing 426 may include a polygonal cross-section and the distal section 442 may include a cylindrical cross-section. An annular band 444 may be provided between the two sections 440, 442. The annular band 444 defines circular openings configured to receive ball bearings 446 therein. The distal casing 428 includes a cylindrical body with a distal flange 448. The distal flange 448 may include a radially projecting flange that sits outside the proximal casing 424. A spring 450 fits between the distal casing 428 and the inner casing 426 and around the distal section 442 of the inner casing 426. A washer or ring 452 may be used to secure the distal casing 428 to the assembly 406.

Figure 25A:
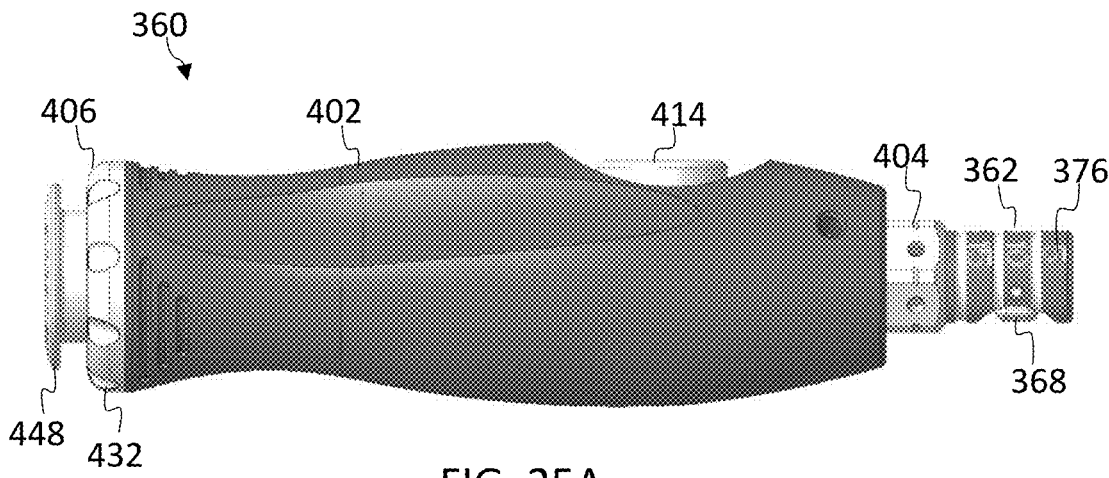
FIGS. 25A-25C show a side view and cross-sectional views, respectively, of the handle with the thread button engaged and disengaged according to one embodiment.
Figure 25B:
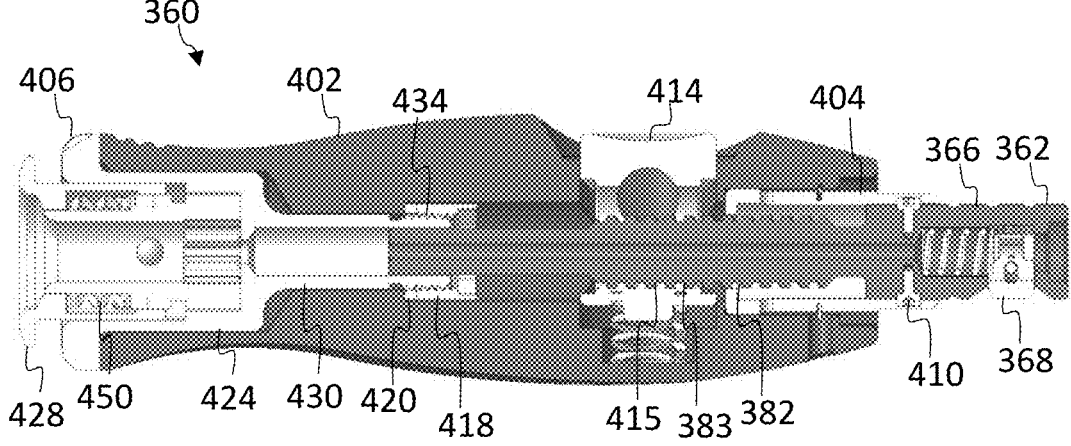
Figure 25C:
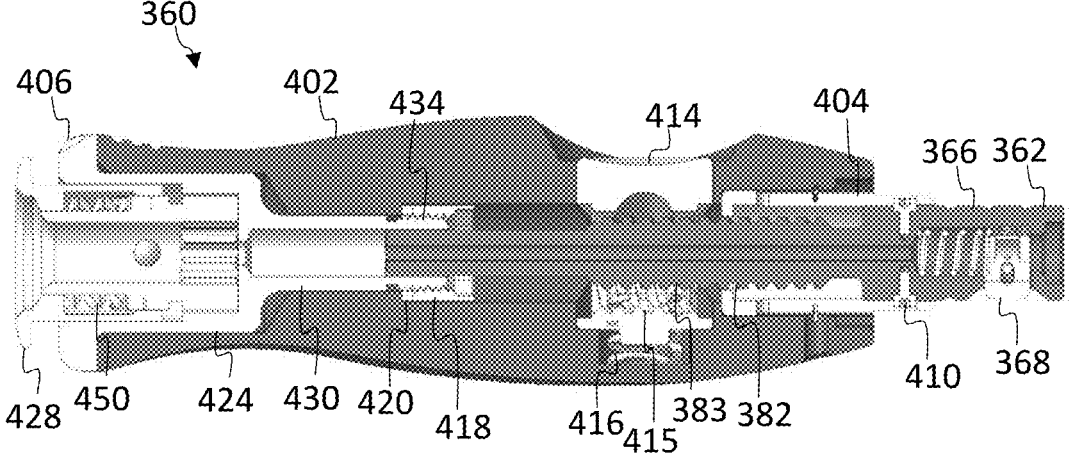

Turning now to FIGS. 25A-25C, the assembled handle assembly 306 is shown in more detail. The central portion 382 of the stylet housing 366 is threaded 383 along its length and is configured to engage corresponding threads 415 on the button 414. The stylet 364 may be actuated in two different ways. As best seen in FIG. 25B, in a first manner, the spring-loaded thread button 414 engages the central portion 382 of the stylet housing 366 to allow the housing 366 to move along a fixed linear track. The stylet housing 366 may have a male thread form 383 that mates with the same female thread form 415 of the thread button 414. By rotating the handle grip 402 about the stylet housing 366, the thread button 414 is also rotated about the stylet housing 366. This action allows the stylet housing 366 to actuate along a fixed linear path via the threads 383, 415. As best seen in FIG. 25C, in a second manner, by depressing the thread button 414, the female threads 415 become disengaged from the male threads 383 of the stylet housing 366. In this configuration, the stylet housing 366 is free to actuate and translate forward when force is applied directly to the top of the stylet housing 366. In each configuration, the stylet 364 translates with stylet housing assembly 382 to accommodate different screw lengths.

Figure 26A:
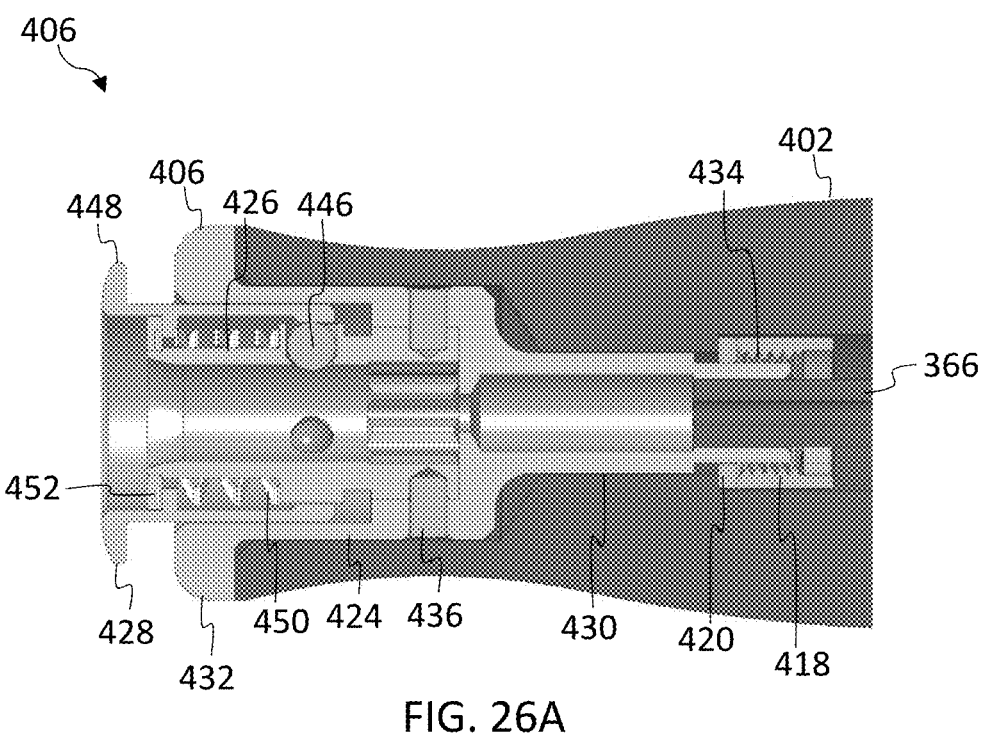
FIGS. 26A-26B show a quick-connect housing assembly including a ball bearing with locked and unlocked positions, respectively, according to one embodiment.
Figure 26B:
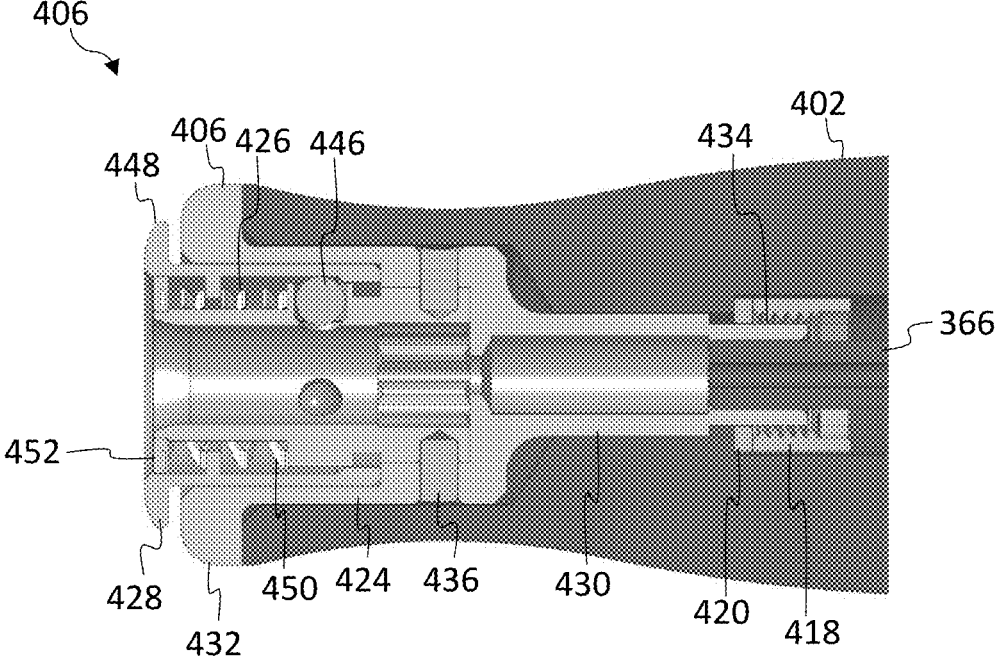

Turning now to FIGS. 26A-26B, the quick-connect housing assembly 406 is shown in more detail. The quick-connect housing assembly 406 is located in the distal end of the handle grip 402. The stylet housing assembly 362 is rotationally coupled to the quick-connect housing assembly 406. In particular, the reduced diameter 378 of stylet housing

366 is positioned in a corresponding openings in the proximal stem 430 of the quick-connect housing assembly 406. The connection may be further secured via threaded ring 418, which threadedly interfaces with threads 432 on the end of proximal stem 430.

The quick-connect housing assembly 406 detachably mates, retains, and is rotationally coupled with the attachment interface 316 on the back of pedicle screwdriver 300 or other suitable instruments. This connection may be achieved with ball-bearings 446 toggling between locked and released states, that mate with groove 317 in inner shaft 306. As shown in FIG. 26A, the distal casing 428 is translated distally, forcing the ball-bearings 446 into the locked state where the ball-bearings 446 engage with groove 317, thereby locking handle assembly 360 to the screwdriver shaft 306. In FIG. 26B, the distal casing 428 is translated proximally and the ball-bearings 446 are positioned in the un-locked state where the ball-bearings are not engaged with the groove 317 and the shaft 306 is free to be removed from the handle assembly 360. This allows the handle assembly 360 to be compatible with any screwdriver including for fluoroscopic guided, navigated, and/or robotic procedures.

Figure 27A:
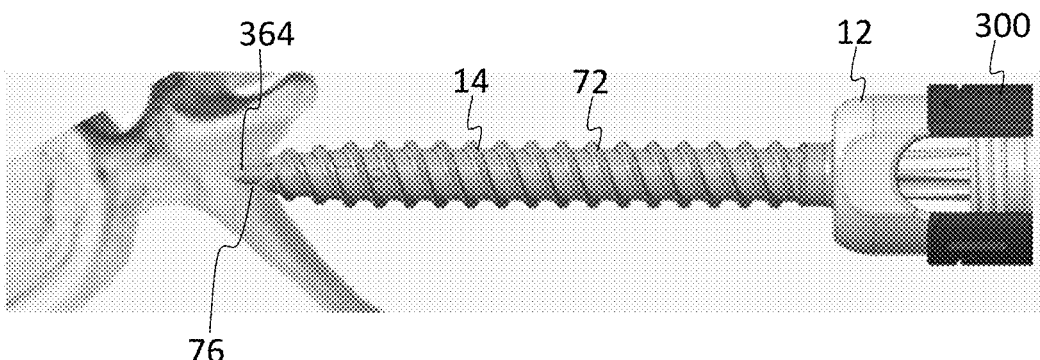
FIGS. 27A-27C show a workflow using the stylet including a docking step, advancing the stylet through the pedicle, and inserting the screw over the stylet according to one embodiment.
Figure 27B:
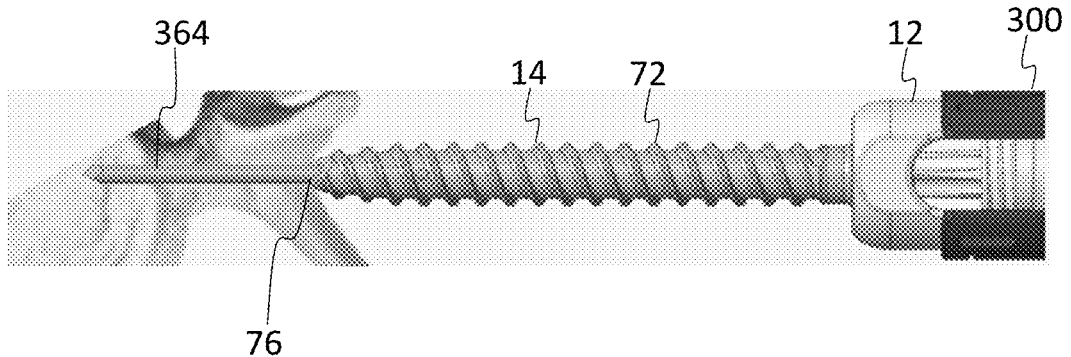
Figure 27C:
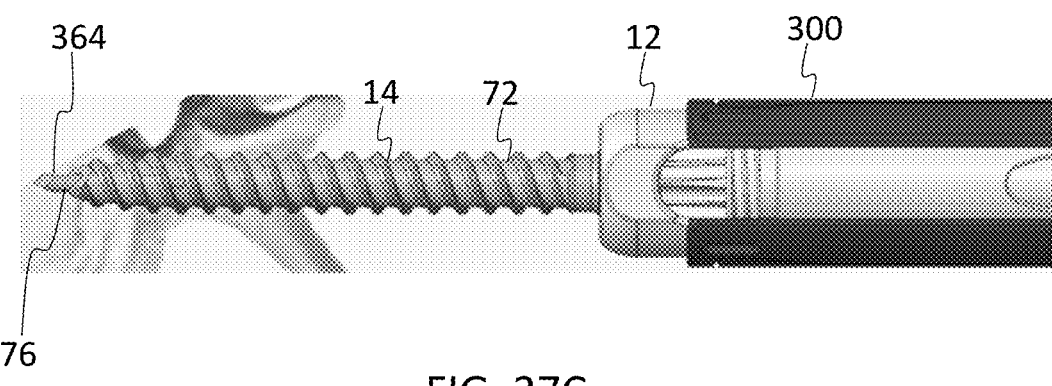

The single step screwdriver 300 provides the user an array of different workflows. One example workflow is shown in FIGS. 27A-27C. A first step shown in FIG. 27A may be a docking step where the stylet 364 is impacted into bone. With the stylet 364 protruding slightly out of the distal tip 76 of the screw 14, the user impacts on the proximal surface of the instrument 300 to dock the stylet 364 and screw tip 76 into the bone. As shown in FIG. 27B, a second step includes advancing the stylet 364 through the bone. Once the docking step is complete, the stylet 364 is advanced through the pedicle. This provides a preset path for the screw 14 to traverse through the pedicle safely. As shown in FIG. 27C, a third step includes inserting and advancing the screw 14 over the stylet 364. Once the user is satisfied with the trajectory set with the stylet 364, the user drives the screw 14 into the pedicle over the stylet 364. The handle assembly 360 actively retracts the stylet 364 back into the screw 14 as the screw 14 is being driven into bone while user holds the handle 402 stationary relative to the screw driving components. The rate of the stylet retraction may be faster than the screw pitch, to prevent risk of driving the screw into bone with a long protruding wire.

Turning now to FIGS. 28A-28D, a screw extender 460 is shown according to one embodiment. The screw extender 460 attaches to bone screw 14 to provide a rigid extension of the screw 14 such that the position of the vertebra may be registered and/or tracked through tracking of the screw extender or markers attached to the screw extender. Examples of tracking methods can be found, for example, in U.S. Publication No. 2023/0010173, which is incorporated by reference herein in its entirety for all purposes.

The screw extender 460 may include an outer sleeve 462, an inner shaft 464 extending through the outer sleeve 462, and one or more ball bearings 466. The drive recess 80 in the screw head 70 includes a recessed drive portion 468 configured to interface with the outer sleeve 462 and one or more recessed engagement portions 470 configured to interface with the one or more ball bearings 466 of the screw extender 460. The drive recess 80 of the screw 70 is engaged by the similarly shaped tip of the outer sleeve 462. For example, the drive portion 468 of screw 14 may interface with the outer sleeve 462 with a Torx drive or other suitable screw drive mechanism.

Within the drive portion 468, each recessed engagement portion 470 may define an undercut with a circular or spherical cross-section sized and dimensioned to interface with the ball bearing 466 of complimentary size and shape. The undercuts 470 interface with ball bearings 466 of similar size, which translate into engagement with the groove 470 to prevent disengagement of the screw extender 460 by the distal tip of the inner shaft 464. The distal tip of the inner shaft 464 may be angled, beveled, or tapered, for example. As the distal tip of the inner shaft 464 is advanced distally, the ball bearing 466 is seated into the recessed engagement portion 470. When the one or more ball bearings 466 are received in the one or more engagement portions 470, disengagement of the screw extender 460 is thereby prevented allowing for a rigid connection between the instrument 460 and the screw head 70. A caging member 472 may be installed and welded in place to retain the ball bearings 466 in the assembly. The caging member 472 may be provided at the distal-most end of the outer sleeve 462. The caging member 472 may define a groove or channel 474 configured to guide the ball bearing 466 into position. The inner shaft 464 may be threaded or spring loaded to the outer sleeve 462 of the screw extender 460 so that a user may tighten or release the assembly.

The screw extender 460 may couple to a screwdriver instrument 490, which allows the user to align the screw 14 with the intended trajectory and apply the necessary torque to insert the screw 14 into the vertebral body. As shown in FIG. 28C, the back portion or proximal end of the screw extender 460 is configured to connect to the screwdriver 490. The proximal end of the outer sleeve 462 includes a drive interface 476 and a circumferential groove 478 which allows the screw extender 460 to be rigidly constrained to the screwdriver instrument 490. The drive interface 476 may include a plurality of flat faces or straight lobes configured to mate with the screwdriver body 490. The proximal end of the inner shaft 464 may include a ribbed neck 480 having a plurality of longitudinal ribs extending along the length of the inner shaft 464.

Figure 28D:
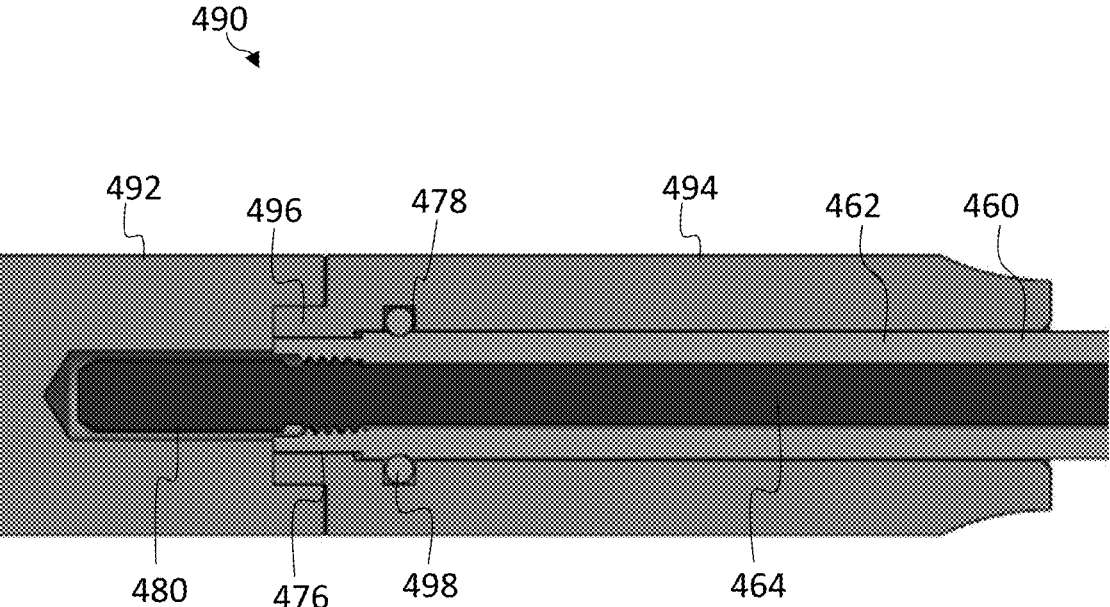

With emphasis on FIG. 28D, the screwdriver instrument 490 may include a two-piece body. A first portion 492 may include a handle portion configured to receive the ribbed neck 480 of the inner shaft 84. A second portion 494 may include a tubular body configured to receive the outer sleeve 462 of the screw extender 460. A female drive seat 496 may mate with the drive interface 476 of the outer sleeve 462. A flexible mechanical spring 498 may engage with the groove 478 in the back portion of the screw extender 460. The screwdriver 490 allows the user to apply the necessary torque to insert the screw 14 into bone.

Figure 29A:
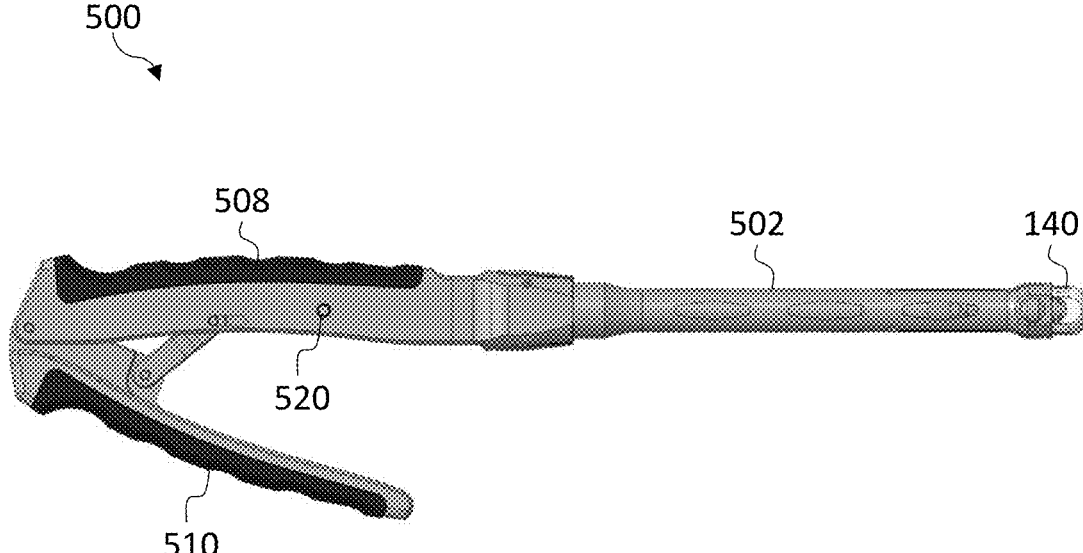
FIGS. 29A-29B show front and back views, respectively, of a tulip head inserter assembly according to one embodiment.
Figure 29B:
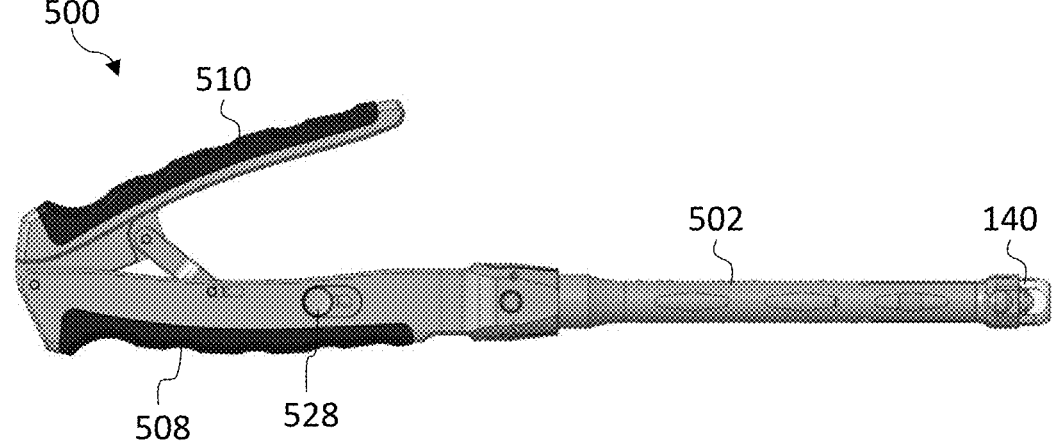

Turning now to FIGS. 29A-33, a modular head inserter 500 is shown according to one embodiment. The modular head inserter 500 aids the user with the application of a modular tulip head 140 to a screw 14 in-situ. As the modular tulip assembly 140 locks to the screw head 70, the modular head inserter 500 serves as a way to provide feedback to the user to confirm whether or not the screw 14 has attached to the tulip assembly 140. FIGS. 29A-29B show front and back views illustrating the overall instrument 500 used by the surgeon to deploy the mechanism.

Figure 30:
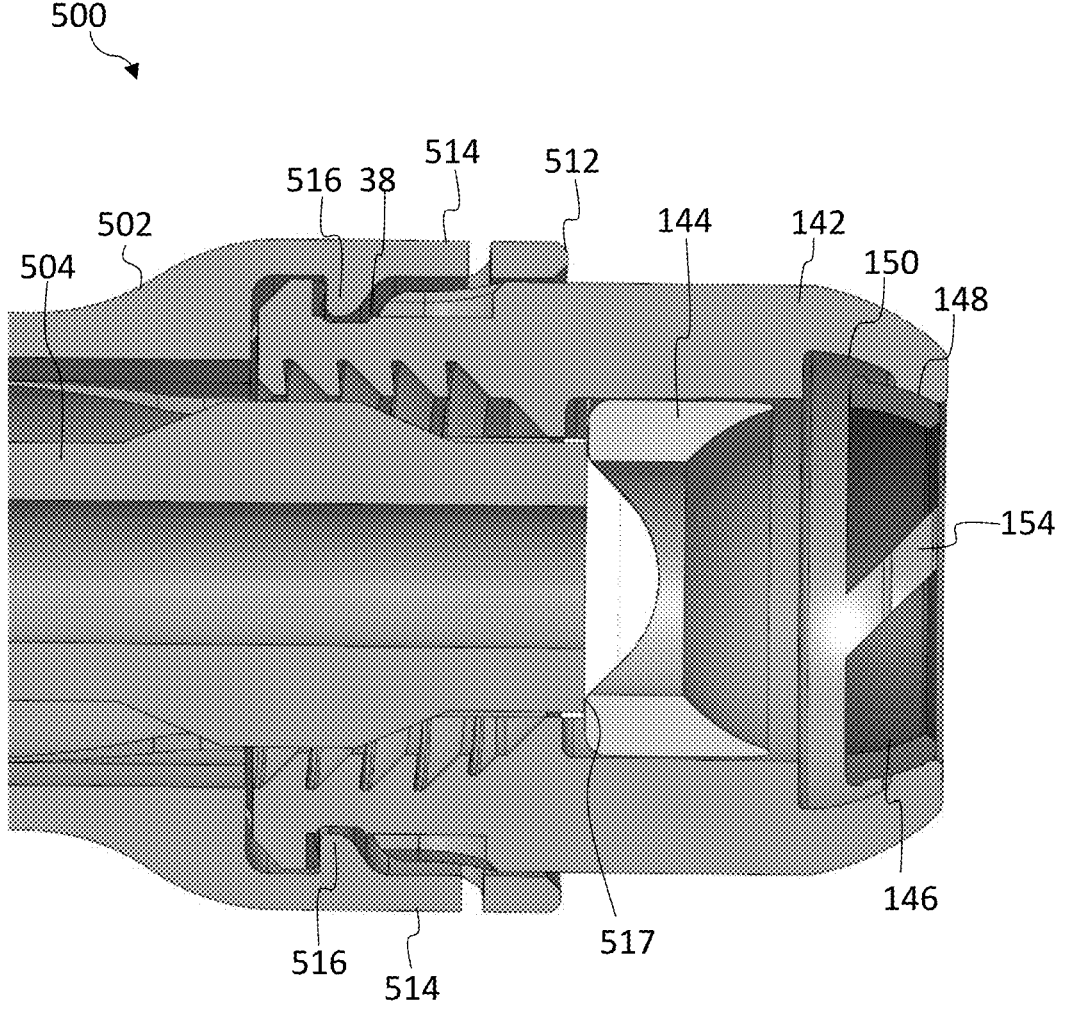
FIG. 30 is a cross-section of a modular head inserter attached to a tulip head assembly according to one embodiment.

The modular head inserter 500 includes an outer sleeve 502, an inner sensing shaft 504, an inner release shaft 506, a stationary handle 508, and a moveable handle 510. The outer sleeve 502 includes a tubular body for receiving the inner sensing shaft 504 and inner release shaft 506. As best seen in FIG. 30, the outer sleeve 502 includes a distal end 512 with spring tabs 514 configured to mate with the arms 26 of the tulip head 142. Each of the spring tabs 514 includes an inward-facing protrusion 516 sized and dimensioned to fit within the groove 38 in the tulip head 142. The modular tulip 142 is retained to the distal portion 512 of the instrument 500 via the releasable spring tabs 514, which interface with the groove 38 on the outer surface 36 of the modular tulip 142. The interaction between spring tabs 514 and groove 38 may form a dovetail connection to constrain the instrument 300 axially to the tulip head 142. The inward angle may help to prevent disengagement of the instrument 300 under load by directing forces inward and toward the central axis of the tulip head 142.

The sensing shaft 504 may include a cannulated body with a distal end 517 and a proximal end 518, which is spring loaded via spring 519. The distal surface 518 of the sensing shaft 504 of the head inserter 500 is configured to contact the proximal surface of the saddle 144 of the modular tulip assembly 140. Upon insertion of the screw shank 72 into the modular tulip 142, the head 70 of the screw 14 pushes up in the proximal direction on the saddle 144, consequently pushing the sensing shaft 504 of the head inserter 500 in the same direction.

Figure 31A:
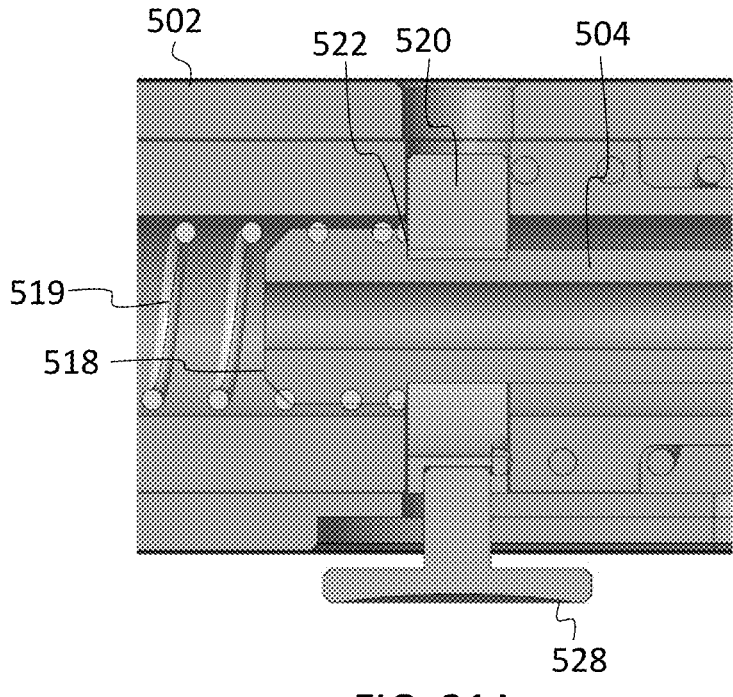
FIGS. 31A-31B show an actuation mechanism in unlocked and locked positions, respectively, for enabling a user to actuate a release shaft of the head inserter according to one embodiment.
Figure 31B:
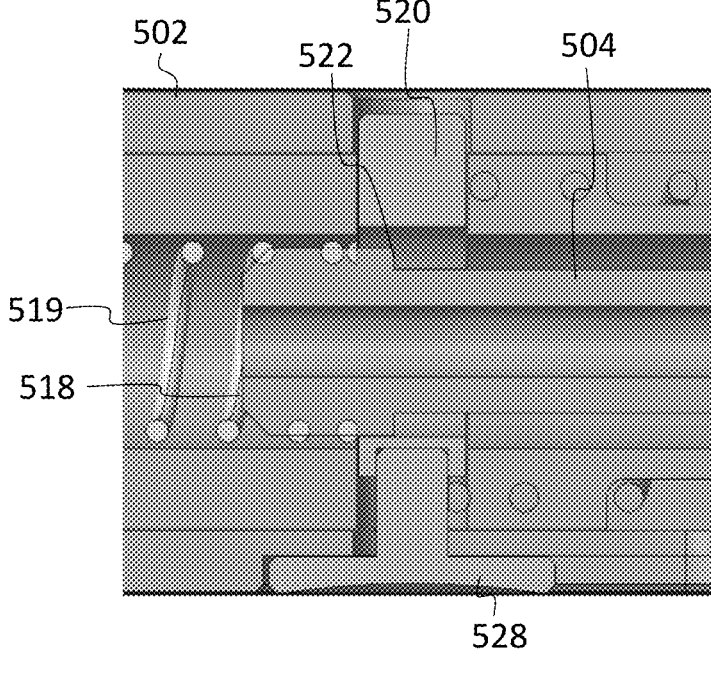
Figure 32:
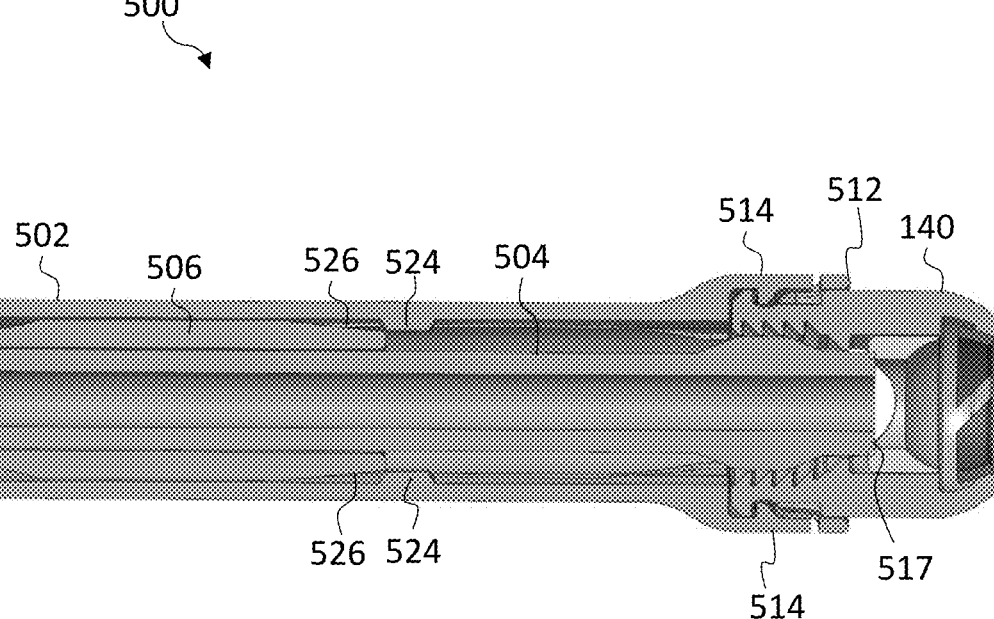
FIG. 32 shows a tulip release mechanism including the release shaft for releasing the tulip head assembly from the head inserter according to one embodiment.

As best seen in FIGS. 31A-31B, when the sensing shaft 504 is pushed proximally, a spring-loaded lock button 520 will snap into groove 522 of the sensing shaft 504 only accessible in the pushed state. When this button 520 engages with the sensing shaft 504, the button 520 simultaneously disengages the actuation mechanism from the body of the head inserter 500. The user may then actuate the handle 510, which is linked to release shaft 506. The release shaft 502 is located between the outer sleeve 502 and inner sensing shaft 504. As best seen in FIG. 32, the release shaft 506 pushes laterally on the spring tabs 514 retaining the tulip 142, thereby releasing the tulip 142 from the instrument 500. An inner surface of outer sleeve 502 may define projections 524 and an outer surface of the inner release shaft 506 may define a tapered distal end 526. As the release shaft 502 translates proximally, the tapered end 526 of the release shaft 502 pushes against projections 524 to push the spring tabs 514 outward and away from one another. The modular tulip assembly 140 is left behind in-situ attached to the screw shank 72.

After the sensing mechanism is tripped, the sensing shaft 504 must be reset in order to be used again. This is accomplished by depressing the reset button 528, which opens up the lock 520, returning the lock 520 to its locked state now interfering with the body of the head inserter 500. Because the sensing shaft 504 is spring loaded via spring 519, retraction of lock button 520 causes the sensing shaft 504 to return to its starting position. The release mechanism in this state will no longer be able to actuate until the sensing mechanism is tripped again.

Figure 33:
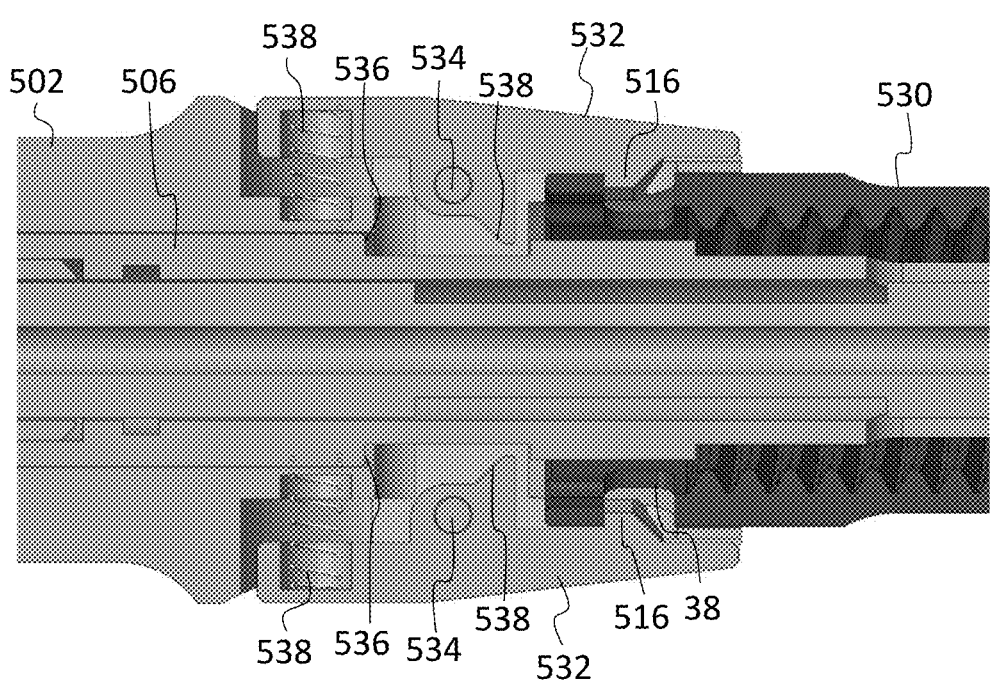
FIG. 33 shows an alternative head inserter with pivotable clips for securing a MIS tower according to one embodiment.

In an alternative embodiment shown in FIG. 33, the head inserter instrument 500 may be modified to connect to other instrumentation, such as MIS tower 530. For this approach, rather than the release shaft 506 pushing on spring tabs 514 retaining the tulip 142, the release shaft 506 interfaces with clips 532 retaining the MIS tower 530 to the head inserter 500. The clips 532 include inward-facing protrusions 516, similar to spring tabs 514, which interface with the dovetail groove 38 on the outer surface 36 of the tower 530 to retain the MIS tower 530. The clips 532 may be pivotably coupled to the outer sleeve 502 via pivot pins 534. When the release mechanism is actuated, a positive ledge 536 on the release shaft 506 contacts a built-in lever 538 on the release clips 532, cantilevering the release clips 532 into an unlocked state. The lever 538 may include a tapered or angled surface, which the positive ledge 536 presses against to pivot the release clips 532 outward. In this mode, the head inserter 500 leaves behind the tulip/tower assembly 530 when the release mechanism is actuated. The clips 532 may be spring loaded via springs 538 to return the clips 532 inward when the release shaft is returned proximally.

Figures 34A, 34B, 34C:
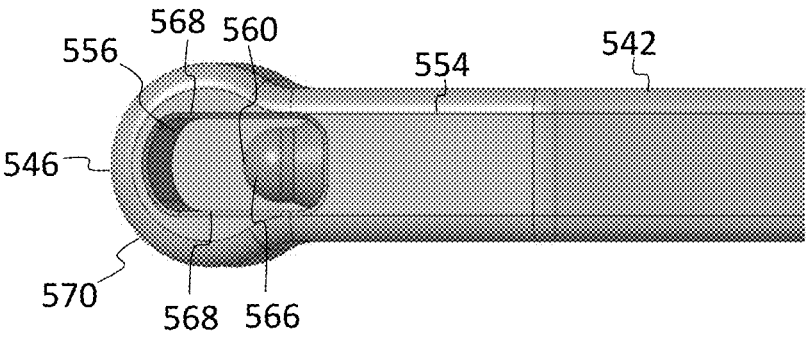
FIGS. 34A-34D show a MIS rod holder instrument for inserting and manipulating MIS rods according to one embodiment.

Turning now to FIGS. 34A-34D, a rod holder and inserter instrument 540 is shown according to one embodiment. The MIS rod holder 540 aids the user with the insertion and manipulation of MIS rods 18. The MIS rod holder 540 includes a hollow tubular body 542 extending from a proximal end 542 to a distal end 546. The tubular body 542 of the inserter 540 houses the locking pin 548. The body 542 may be a square or rectangular tube sized dimensioned to receive a locking pin 548 therethrough. The proximal end 542 of the body 542 attaches to a handle 550, for example, via neck 552. The neck 552 and handle 550 may be angled relative to tubular body 542. The handle 550 may provide an ergonomic grip for the user. As best seen in FIG. 34B, the distal end 546 of the body 542 may angled or tapered 554 downward toward the distal-most tip. As best seen in FIG. 34C, the hollow body 542 defines a pocket 556 at the distal end 546 configured to receive one end of the rod 18.

Figure 34D:
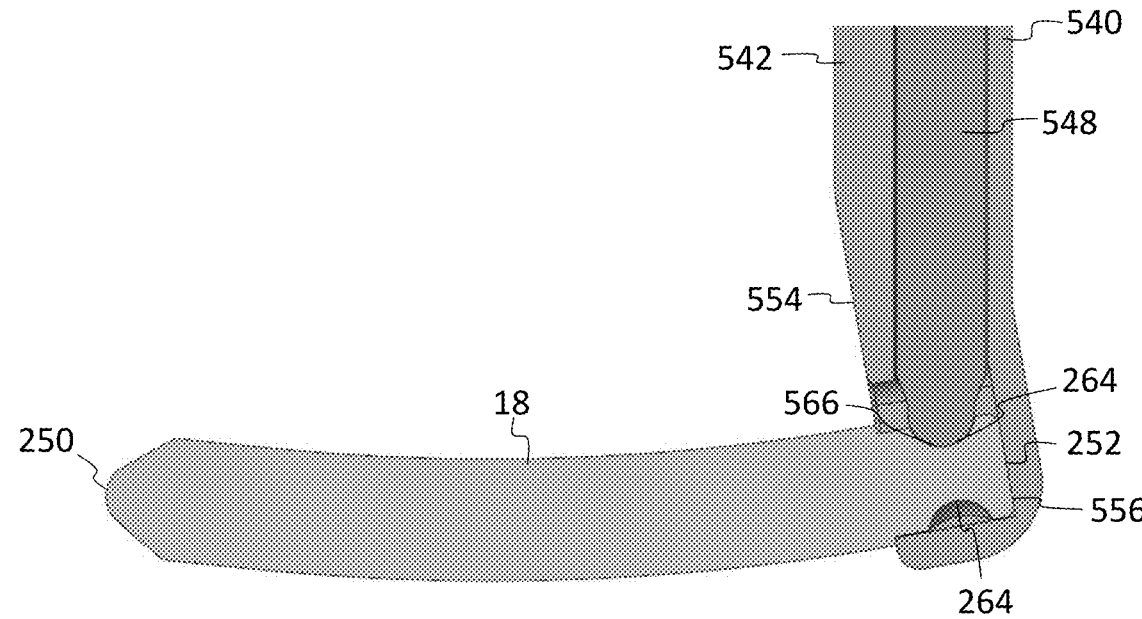
Figure 35A:
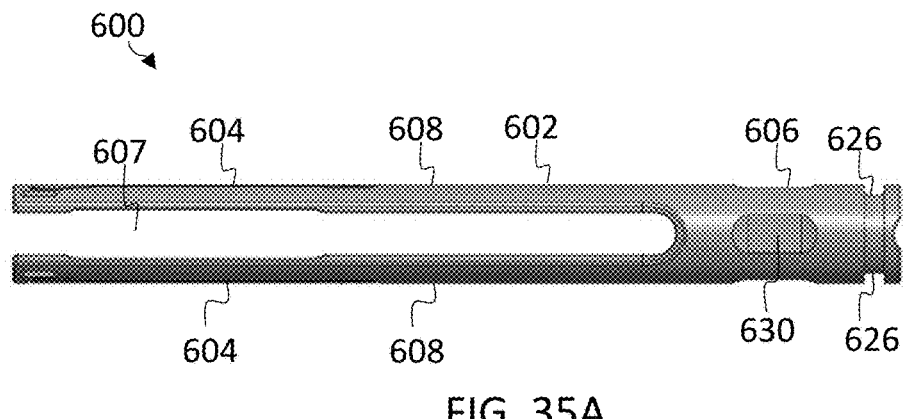
FIGS. 35A-35D show a MIS tower with retaining tabs according to one embodiment.
Figures 35B, 35C:
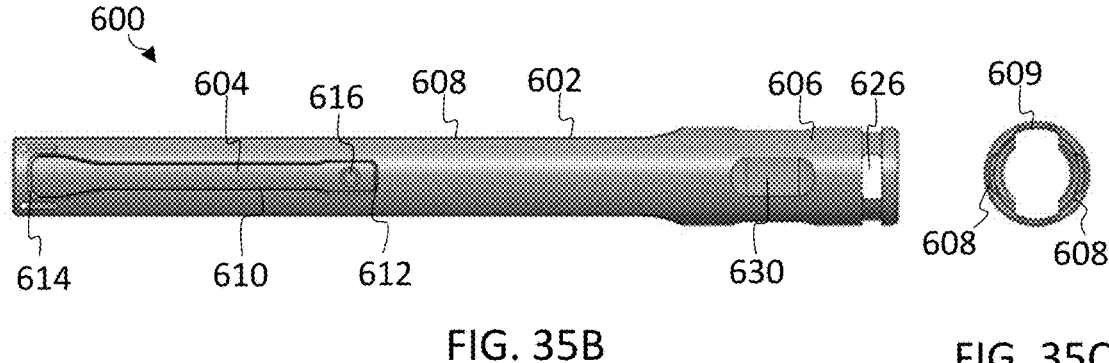
Figure 35D:
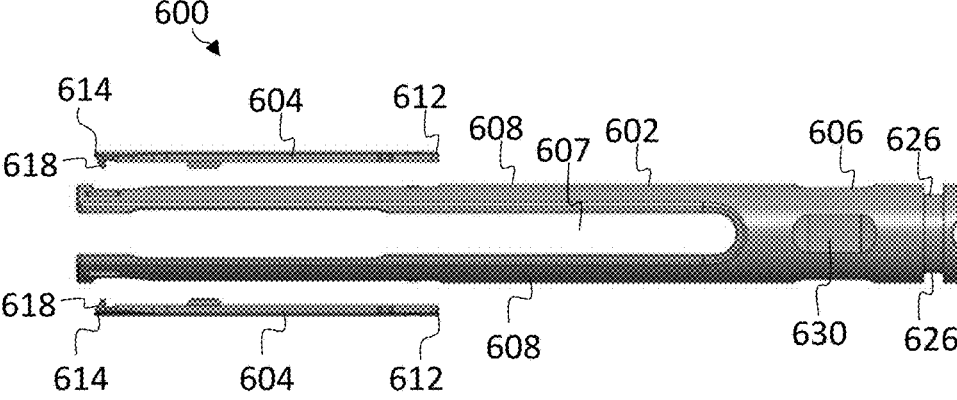

The locking pin 548 extends from proximal end 558 to distal end 560, which enters into pocket 556. The proximal end 558 may include a thumbwheel 562 configured to rotate locking pin 548. The locking pin 548 may be threaded 564 into the body 542 and may be removed for cleaning. The distal tip 560 of the locking pin 548 may be configured to interface with the end of MIS rod 18. For example, the distal tip 560 of the locking pin 548 may have a spherical boss 566 that mates with a corresponding spherical divot 264 on the MIS rods 18 (e.g., as shown in FIGS. 14A-14B) to keep the rod 18 from disengaging from the holder 540. Flats 568 on the sides of the rod connection pocket 556 may engage with corresponding flats 260 on the rods 18 to prevent rotation about the rod axis. The distal end 546 of the body 542 may have an enlarged width 570, for example, having a rounded or circular tip. The enlarged width 570 may be sized to prevent the rod holder 540 from being able to pass through the rod slot 30 of the screw head 12 and MIS tower. As best seen in FIG. 34D, one end 252 of rod 18 is inserted into pocket 556. The locking pin 548 is translated distally, for example, via threaded engagement 546 with the body 542 by rotating the thumbwheel 562 of the locking pin 548. The spherical boss 566 enters divot 264, thereby temporarily securing the rod 18 to the rod holder 540. After the rod 18 is installed, the locking pin 548 may be withdrawn from divot 264 to remove the instrument 540.

Turning now to FIGS. 35A-37C, a MIS tower 600 is shown according to one embodiment. The MIS tower 600 attaches to a screw head, such as tulip head assembly 10, and is used to provide a guide and working channel in percutaneous approaches. As best seen in FIGS. 35A-35D, the MIS tower 600 includes a tower body 602 and two screw head retaining tabs 604. The tower body 602 includes a proximal base 606 and two distal arms 608 with a channel or rod slot 607 defined therebetween. The rod slot 607 extends through the side of tower body 602 and is sized to allow passage of a rod, such as spinal rod 18. The arms 608 of the tower body 602 may have semi-circular cross-sections and are generally aligned with arms 26 of the tulip head 12. As best seen in FIG. 35C, slots 609 may extend through the length of the tower 600 to allow reducers and instrumentation to pass through internally. The arms 608 of the tower body 602 include matching cutouts 610 for receiving the respective retaining tabs 604.

Figure 36A:
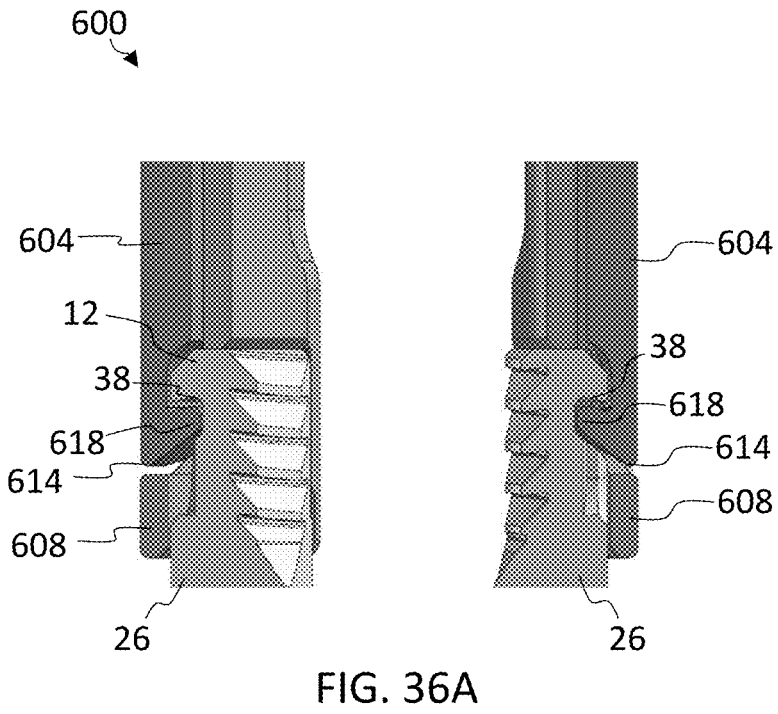
FIGS. 36A-36D show additional details of the MIS tower.
Figure 36B:
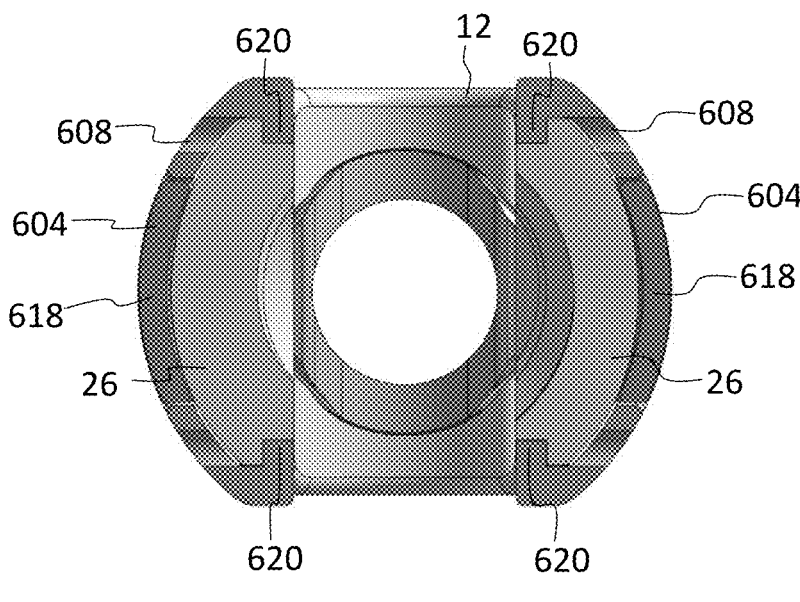

The retaining tabs 604 extend from a proximal end 612 to a distal end 614 configured to capture the tulip head 12. The proximal end 612 of each tab 604 may be retained to the arm 608 with via protrusion 616, a pin, or other suitable attachment mechanism. The protrusion 616 may be press-fit into a corresponding opening in the tab 604 to attach the tabs 604 to the respective tower arms 608. As best seen in FIGS. 36A and 36B, the distal ends 614 of the tabs 604 include an inward-facing protrusion or hook 618 configured to mate with the underside of circumferential groove 38 on the screw head 12. Similar to inward-facing protrusions 516, the interaction between retaining tabs 604 and groove 38 may form a dovetail connection to constrain the instrument 500 axially to the tulip head 12. The inward angle may help to prevent disengagement of the instrument 500 under load by directing forces inward and toward the central axis of the tulip head 12. The hooks 618 may also help to keep the tower 600 attached under tension.

Figure 36C:
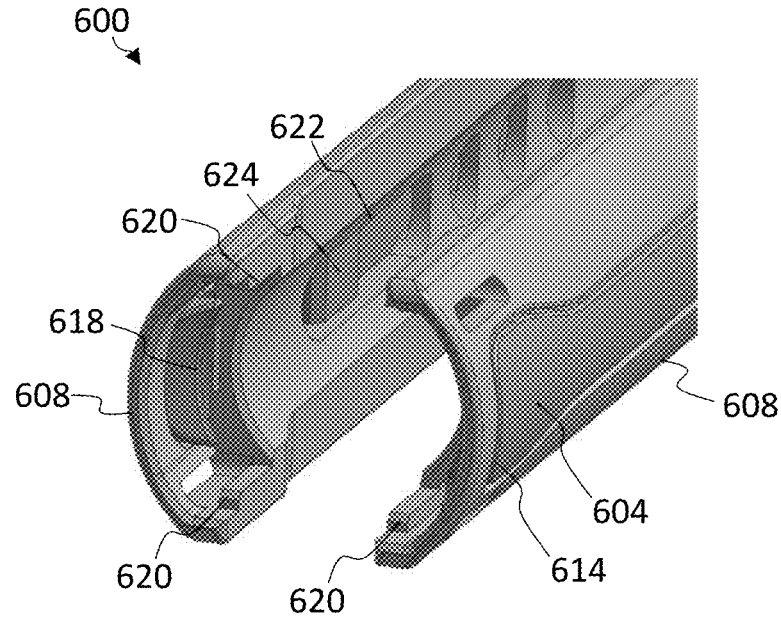

As best seen in FIG. 36C, the distal end of the tower body 602 has a pocket sized to accept the screw head 12 and four ribs 620 that mate with four corresponding grooves or tower pockets 40 and inward-facing surfaces 41 on the screw head 12 to prevent rotation and splay of the tower 600. Two ribs 620 may be provided on opposite ends of each tower arm 608 and may be aligned generally in parallel with tool axis. The tower arms 608 may each define a slot 622 for receiving an inward projection 624 of tab 604. Slots 622 through the sides of tower body 602 provide access to the underside of the retaining tabs 604 to allow them to be spread outward by an instrument to release the screw head.

Figure 36D:
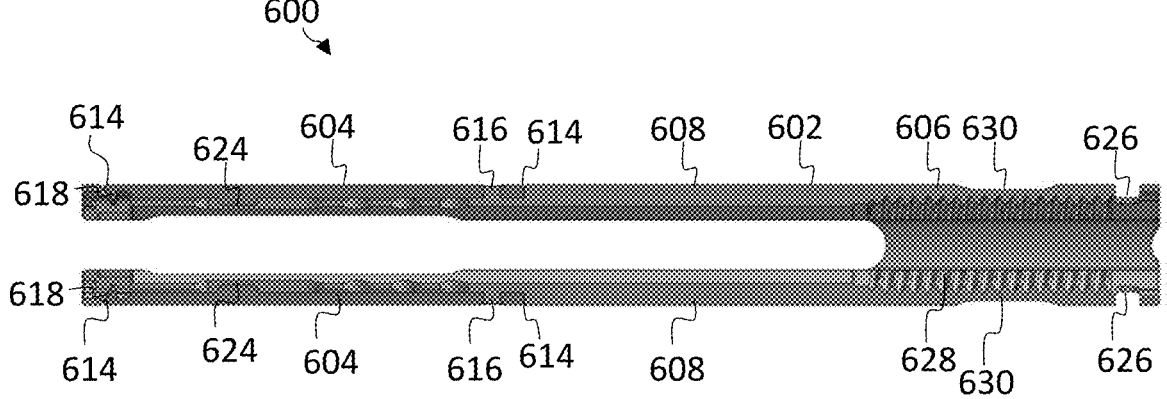

As best seen in FIG. 36D, the proximal end of the base 606 may include cutouts 626 aligned generally perpendicular to the tool axis. The cutouts 626 at the top of the tower 600 may provide an attachment point for instrumentation such as reducers and head inserters. The tower base 606 may be cannulated with internal threads 628 along its length. The internal threads 628 at the proximal end of the tower 600 provide an additional interface option for a threaded reduction instrument. Flats 630 may be provided about the tower base 606. For example, four equally spaced flat sections 630 may be located on the outside of the proximal end of the tower body 602 to provide an interface for a counter-torque instrument.

Figure 37A:
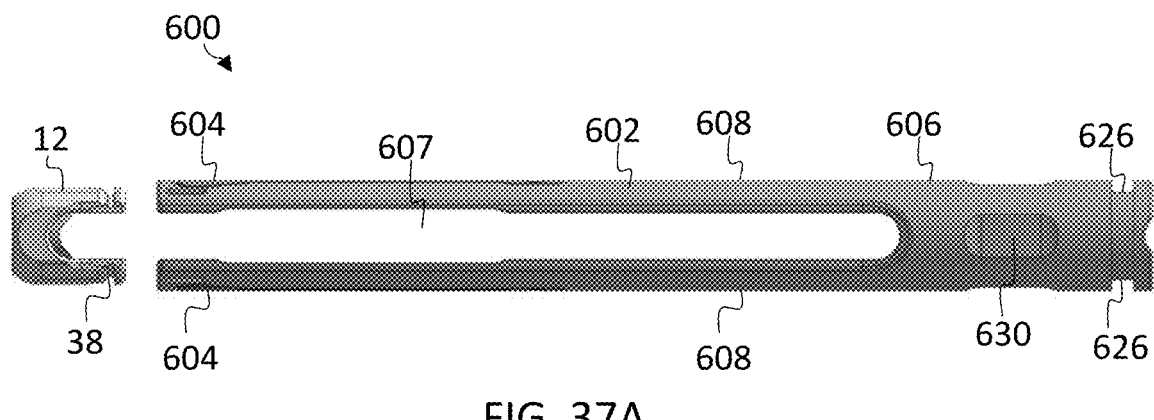
FIGS. 37A-37C show steps for assembling a tulip head to the MIS tower according to one embodiment.
Figure 37B:
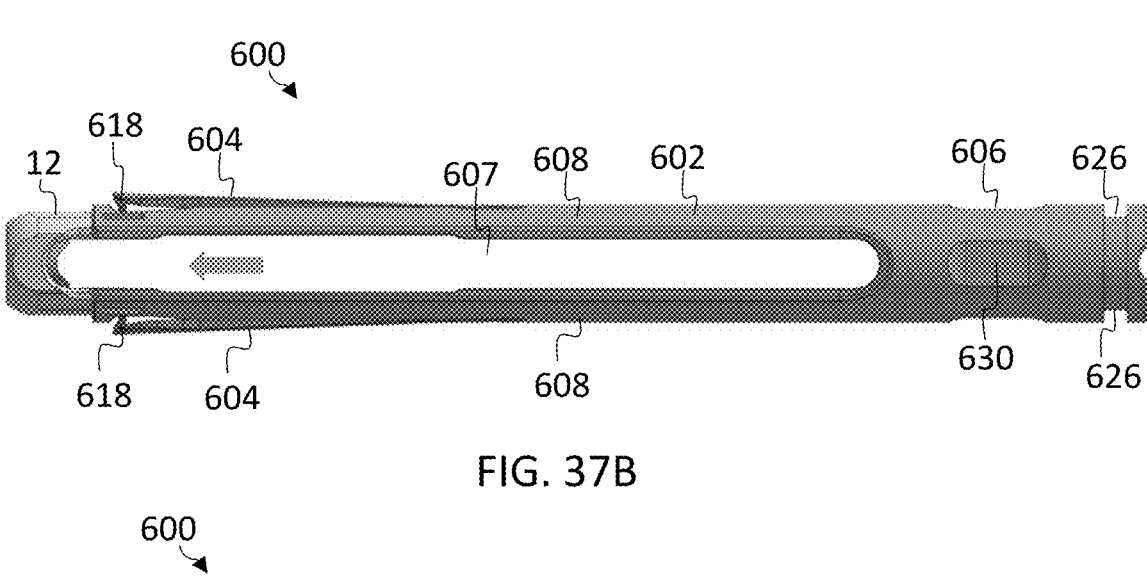
Figure 37C:
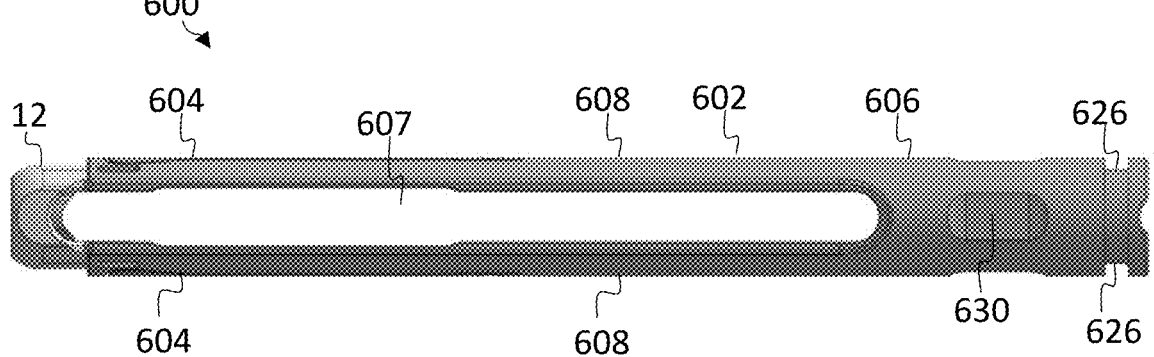

Turning now to FIGS. 37A-37C, assembly of the MIS tower 600 is shown according to one embodiment. As shown in FIG. 37A, the tower 600 is aligned coaxially with the screw head 12. The tower 600 is oriented such that the tower arms 608 line up with the tulip arms 26. As shown in FIG. 37B, the tower 600 is pressed distally onto the screw head 12. The retaining tabs 604 splay outward as the screw head 12 is inserted. As shown in FIG. 37C, the tower 600 and screw head 12 are fully engaged. The hooks 618 of the retaining tabs 604 snap into the dovetail groove 38 on the screw head 12 to prevent unintended removal. After the procedure the tower 600 may be removed by splaying the retaining tabs 604 outward, for example, via engagement with inner protrusions 624, thereby permitting removal of the tulip head 12.

Turning now to FIGS. 38A-40C, a MIS tower removal tool 640 is shown according to one embodiment. The MIS tower removal tool 604 is configured to be inserted into tower 600 to engage inner protrusions 624, release retaining tabs 604, and thereby release the tulip head 12. The tower removal tool 640 includes a handle assembly 642, inner shaft 644, outer sleeve 646, and a pair of opposed spreaders 648.

The handle assembly 642 includes a fixed handle 650 and a moveable handle 652 with grips configured to be squeezed by a user. The handle assembly 642 is used to actuate the inner shaft 644 inside the outer sleeve 646 allowing the two spreaders 648 at the tip to extend or retract. The spreaders 648 extend when the handle 652 is depressed and retract when the handle 652 is released. Return springs 654 in the handle assembly 642 provide the retraction force. The outer sleeve 646 may include guides 656 at the proximal end of the sleeve 646. The guides 656 may include axial tabs provided on either side of the outer sleeve 646. The pair of opposed guides 656 may mate with corresponding slots on the inside of the MIS tower 600. The guides 656 ensure the instrument 640 is in the proper orientation with the screw tower 600 and cannot be inserted in an incorrect orientation.

Figure 38A:
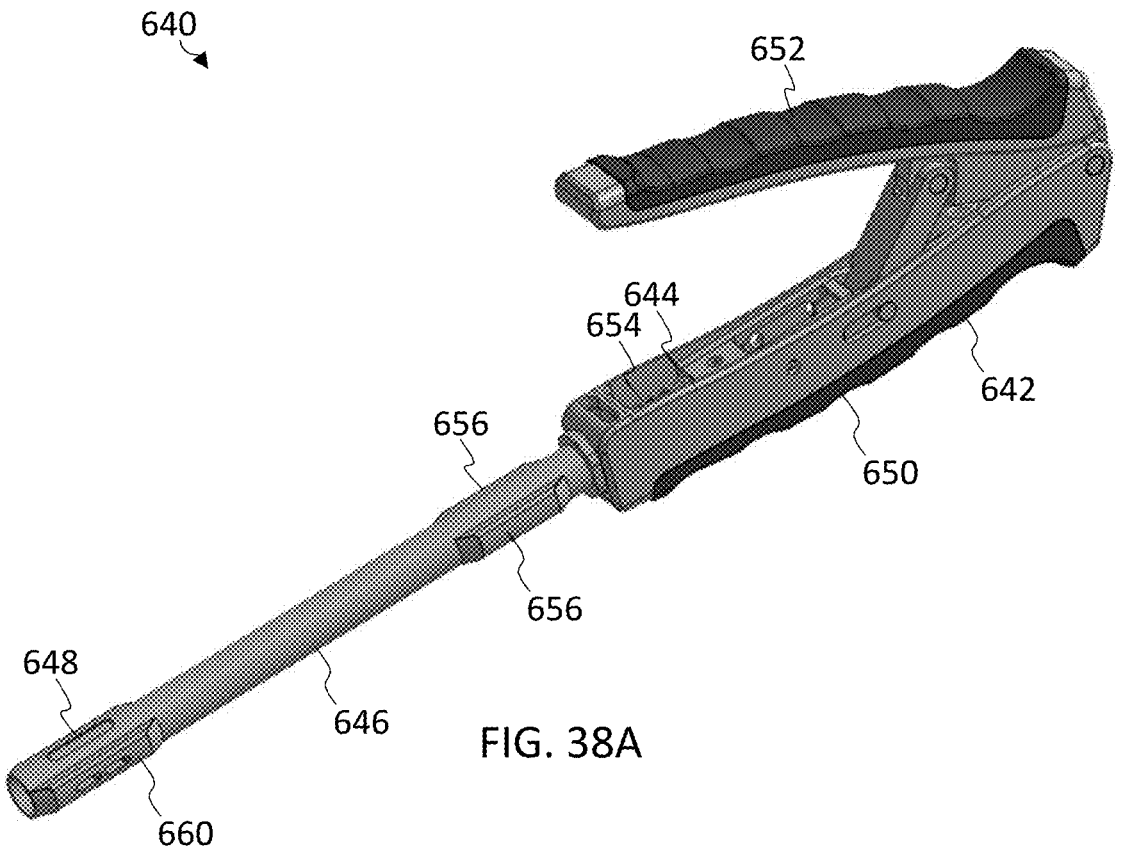
FIGS. 38A-38B show a MIS tower removal tool according to one embodiment.
Figure 38B:
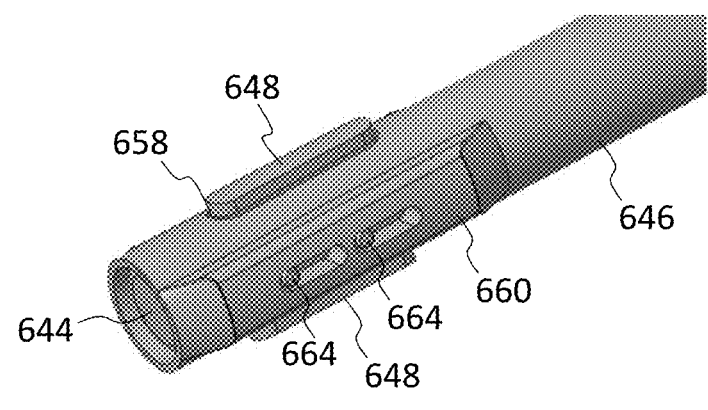
Figure 39A:
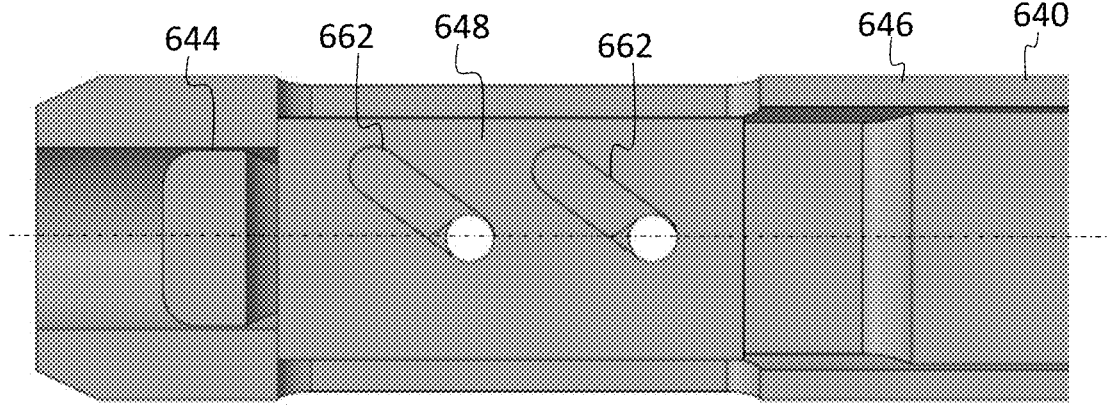
FIGS. 39A-39B show a cross-section of the MIS tower removal tool tip in retracted and extended positions, respectively.
Figure 39B:
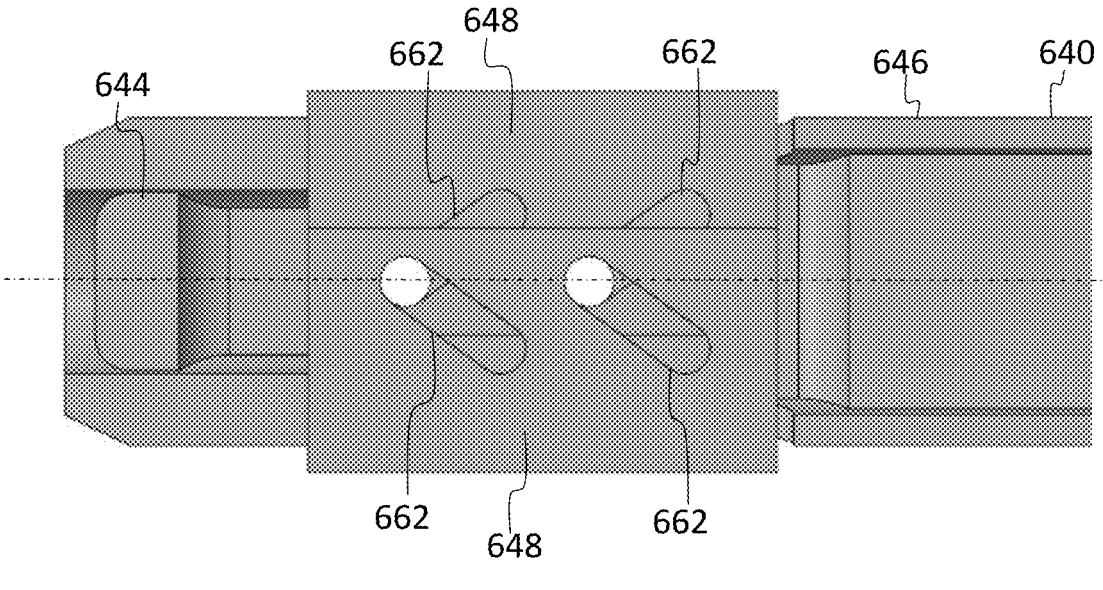

As best seen in FIG. 38B, the distal end of the outer sleeve 646 includes elongated openings 658 sized and dimensioned to receive the spreaders 648. The openings 658 and spreaders 648 may have an elongated or obround shape. The distal end of the outer sleeve 646 may also include axial tabs 660, which fit into the slots 609 of the tower body 602 and help to retain the spreaders 648. As best seen in FIGS. 39A-39B, the spreaders 648 have angled slots 662 which ride on pins 664 pressed into the inner shaft 644. The angled slots 662 may include a pair of parallel slots on each spreader 648. An upper spreader 648 may have a pair of angled slots 662 with a lower distal portion slanted to a higher proximal portion. A lower spreader 648 may be mirrored about the tool axis with the pair of angled slots 662 with a higher distal portion slanted to a lower proximal portion. It will be appreciated that the angled slots 662 may be configured in any suitable manner to extend the spreaders 648 outward and away from one another. As best seen in FIG. 39A, the spreaders 648 are fully retracted inside the outer sleeve 646. As best seen in FIG. 39B, the spreaders 648 are fully extended through openings 658 in outer sleeve 646. When the inner shaft 644 is advanced distally, the spreaders 648 ride along pins 664, thereby extending the spreaders 648 outward and away from one another. When the spreaders 648 extend outward, they pass through slots 622 in the wall of the tower 600 and contact the underside 624 of the tulip retaining tabs 604. This causes the retaining tabs 604 to separate from tulip 12 allowing the tower 600 to be removed. The slots 622 in the wall of the tower 600 also allow the tower 600 to be retained by the instrument 640 while the spreaders 648 are extended.

Figures 40A, 40B, 40C:
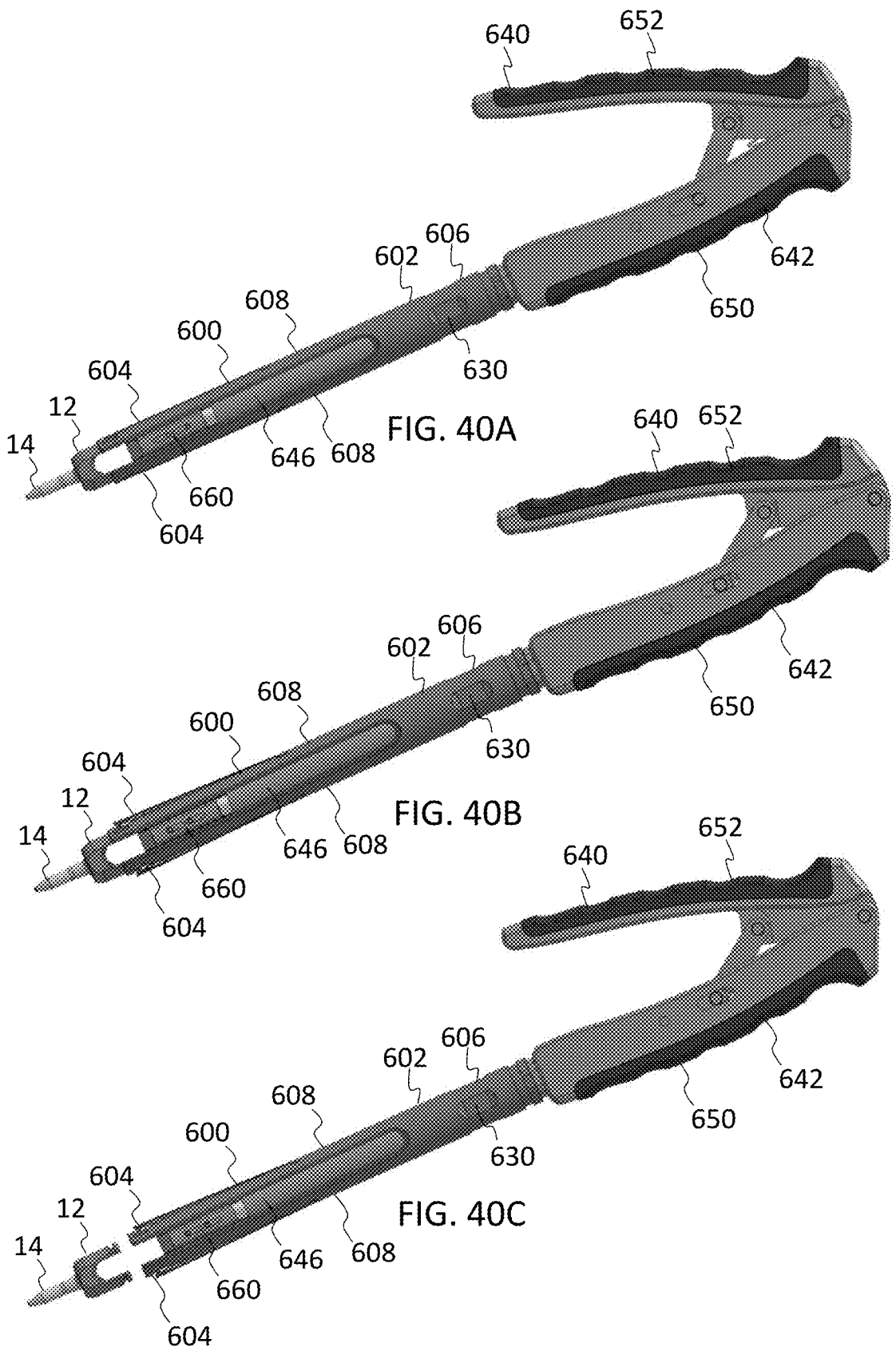
FIGS. 40A-40C show a MIS tower removal process according to one embodiment.
Figure 41:
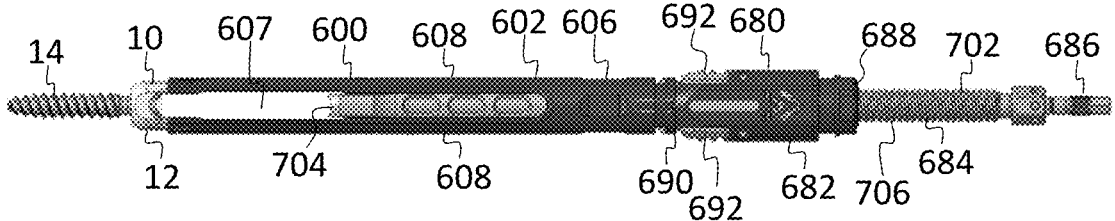
FIG. 41 shows a reducer assembly for interfacing with the MIS tower to push a spinal rod into the tulip assembly according to one embodiment.

A MIS tower removal process is shown FIGS. 40A-40C according to one embodiment. In FIG. 40A, the remover tool 640 is inserted into the MIS tower 600. In FIG. 40B, the handle 652 is depressed to translate the inner shaft 655 forward distally. This causes the spreaders 648 to extend outward and press against inner projections 624 on the retaining tabs 604. The retaining tabs 604 splay open, releasing the tulip head 12 from the tower 600. In FIG. 40C, the remover tool 640 is pulled away from the tulip 12 while keeping the handle 652 depressed. The tower 600 remains retained on the instrument 640 until the handle 652 is released.

Turning now to FIGS. 41A-42B, a reducer assembly 680 is shown for interfacing with the MIS tower 600. The reducer assembly 680 is configured to push the spinal rod 18 into the tulip assembly 10. Once reduced into the tulip assembly 10, the locking cap 16 may be inserted into the tulip 12, capturing the rod 18 in the tulip 12. In this embodiment, the reducer assembly 680 includes a MIS zip reducer having an outer housing 682, an inner pusher 684, and a locking cap driver 686 aligned along a tool axis.

The MIS zip reducer housing 682 includes a hollow body extending from a proximal end 688 to a distal end 690. The outer housing 682 is sized and dimensioned to receive the inner pusher 684 therethrough. The housing 682 attaches to cutouts 626 on the proximal end of the MIS tower 600 via releasable spring clips 692. The spring clips 692 may be pivotably coupled to housing 682 via pivot pins 694. The distal ends of clips 692 may include outward-facing protrusions or keying prongs 696, which interface with corresponding through slots 626 on the MIS tower 600 to prevent rotation during usage. The clips 692 may be spring loaded via springs 698 to bias the prongs 696 outward, thereby securing the reducer assembly 680 to the MIS tower 600.

The inner pusher 684 includes a tubular body 702 sized and dimensioned to receive the locking cap driver 686 therethrough. The tubular body 702 terminates at distal tip 704, which is configured to contact spinal rod 18. The distal tip 704 may include a concave rounded surface configured to engage with the spinal rod 18. When the spinal rod 18 is seated through slot 607 in the MIS tower 600, the distal tip 704 of the pusher 684 forces rod 18 distally and into engagement with the tulip head 12. As best seen in FIG. 42A, a proximal portion of the inner pusher 684 may include one or more threads 706 configured to mate with corresponding threads 708 on half nuts 710 retained inside housing 682.

As best seen in FIG. 42B, the half nuts 710 may be secured in the housing 682 on pins 712. The pins 712 may be configured to run along ramps 714. The ramps 714 may include angled slots defined through the housing 682. For example, two pairs of angled slots 714 may be angled toward the central tool axis at the proximal end and away from the central tool axis at the distal end of the slots 714. The half nuts 710 may be spring-loaded to ensure engagement with the threaded pusher 684. In order to push the rod 18 distally, threaded portion 706 on the pusher 686 is configured to interface with threaded portions 708 of half nuts 710 retained in housing 682. Threading the pusher 684 with respect to the housing 682 propels the rod 18 into the tulip head 12. The threaded mechanism 708 in the housing 682 is releasable via the ramped half nut mechanism. When axial force is applied to the pusher 684 in the distal direction, the half nuts 710 are forced into an open state by translating in the ramped slots 714 away from the centerline, allowing the threaded pusher 684 to bypass the threads 708 of the nuts 710 in the housing 682. When axial force is applied to the pusher 684 in the proximal direction (e.g., under reduction load), the half nuts 710 are forced into a locked state by translating in the ramped slots 714 towards the centerline. The inner pusher 684 is able to translate rod 18 along slot 617 of the MIS tower 60, thereby allowing for precise positioning and alignment of the spinal rod 18 into its designated place in the tulip assembly 10.

Once the spinal rod 18 is securely seated in the tulip head 12, the locking cap 16 may be threaded into the tulip 12. The locking cap driver 686 may include an elongated shaft extending through the inner pusher 684. The locking cap driver 686 includes a distal tip configured to interface with the locking cap 16, for example, via engagement with drive recess 58. The locking cap driver 686 is configured to tighten the locking cap 16 into the tulip head 12, thereby locking and providing stability to the construct.

Turning now to FIGS. 43A-43D, an open reducer 720 is shown according to one embodiment. The open reducers 720 connect directly to the tulip 12, similarly to how the MIS tower 600 interfaces with the tulip 12. The open reducer 720 includes a reducer body 722 with two screw head retaining tabs 724. In this embodiment, however, the retaining tabs 724 interfacing with the dovetail portion 38 of the tulip 142 are favored laterally in an unlocked state.

The reducer body 722 includes two distal arms 726 defining a channel or rod slot 728 sized to allow passage of a rod, such as spinal rod 18, therethrough. The retaining tabs 724 are configured to capture the tulip head 12. As best seen in FIG. 43C, the distal ends of the tabs 724 include an inward-facing protrusion or hook 730 configured to mate with the underside of circumferential groove 38 on the screw head 12. The interaction between retaining tabs 724 and groove 38 may form a dovetail connection to constrain the instrument 720 axially to the tulip head 12. The retaining tabs 724 may be toggled between locked and unlocked positions by actuating a slider 732 distally and proximally.

The slider 732 may be fixed to two blockers 734, which prevent the tabs 724 from displacing laterally in the locked state. The blockers 734 may include a distal arm 736, which extend between the retaining tabs 724 and the arms 726. The arms 736 terminate with a distal tip 738 configured to prevent movement of the retaining tabs 724. The proximal portion 740 of the blockers 734 may include a convex protrusion configured to interface with the slider 732. The slider 732 may be pinned to the blockers 734 or otherwise secured thereto. When in the unlocked state, the blockers 734 allow freedom for the retaining tabs 724 to return to their natural unlocked state. When in the locked state, as shown in FIG. 43C, the blockers 734 are translated distally to prevent the tabs 724 from moving laterally to their unlocked state.

Figure 43A:
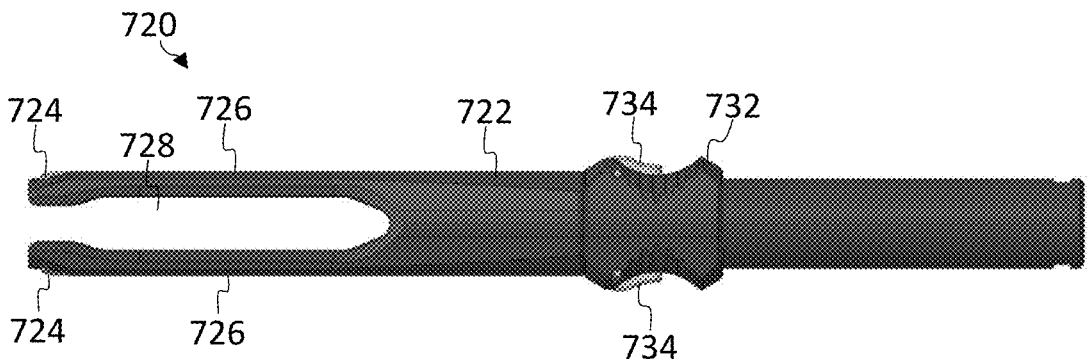
FIGS. 43A-43D show an open reducer assembly with a slider locking mechanism according to one embodiment.
Figure 43B:
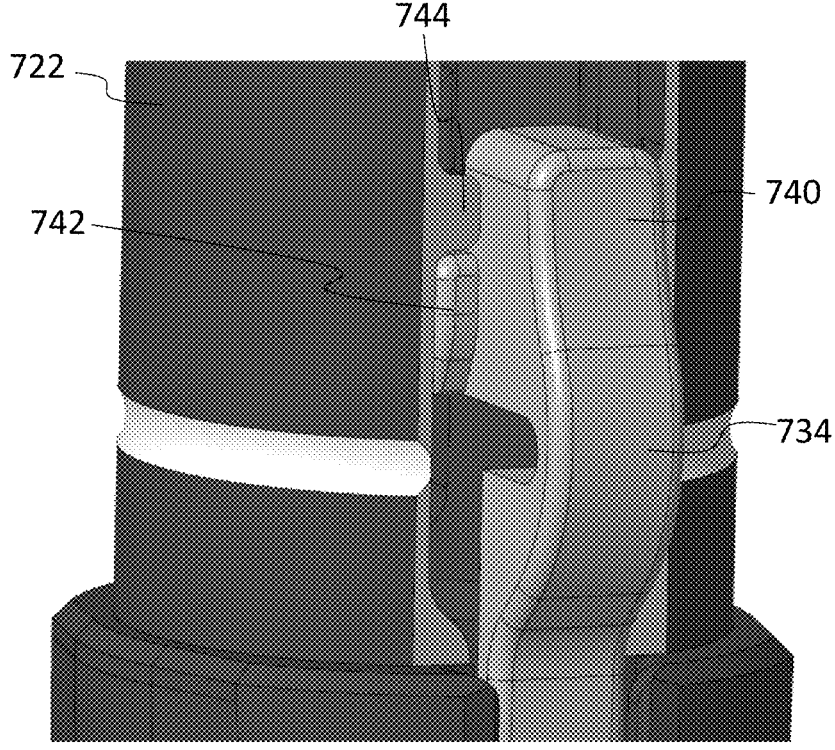
Figure 43C:
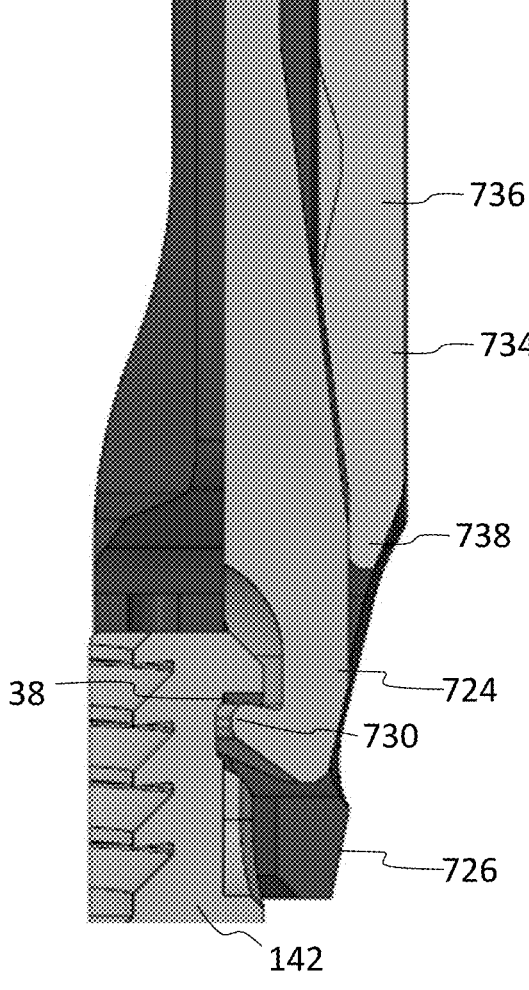
Figure 43D:
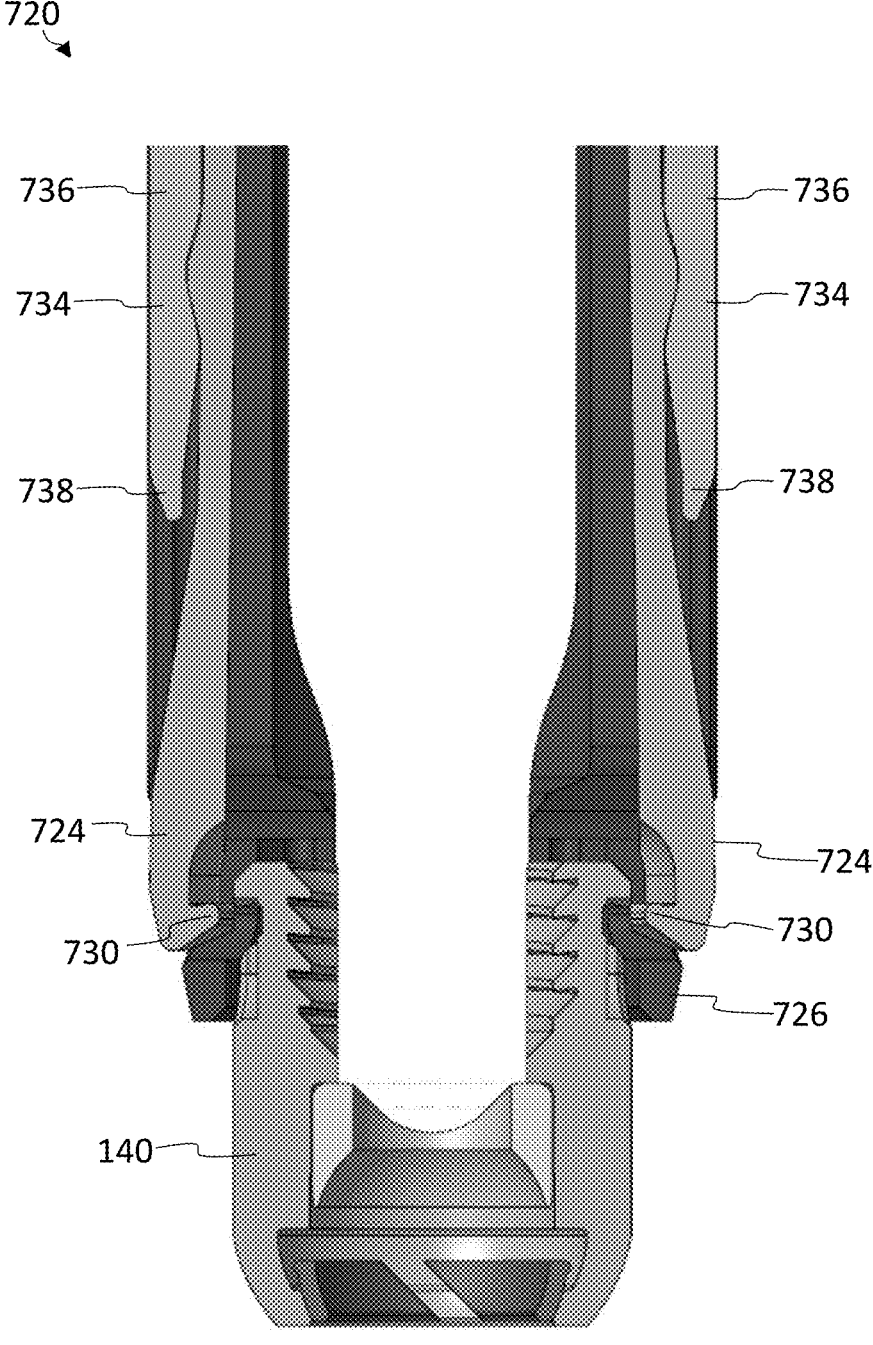

As best seen in FIG. 43B, at the proximal end 740 of the blockers 734 may include protruding surfaces 742, which interface with teeth 744 on the body of the reducer 722. In FIG. 43B, the slider 732 is omitted for clarity. The protruding surface 742 may include lateral projections extending along the side of the proximal portion 740 of the blockers 734. The teeth 744 may include inward projections along the body of the reducer 722. These teeth 744 may be placed such that the blockers 734 are locked in place in the locked position. As best seen in FIG. 43D, in order to unlock the blockers 734, the proximal ends 740 of the blockers 734 must be depressed inward to bypass the teeth 744 on the body 722. In this state, the slider 732 is free to return to the unlocked position and the retaining tabs 724 are free to return laterally to their natural unlocked state. The open reducers 720 may come in longer, shorter, or reduced outer diameter options to accommodate different procedures and patient populations.

Figure 44:
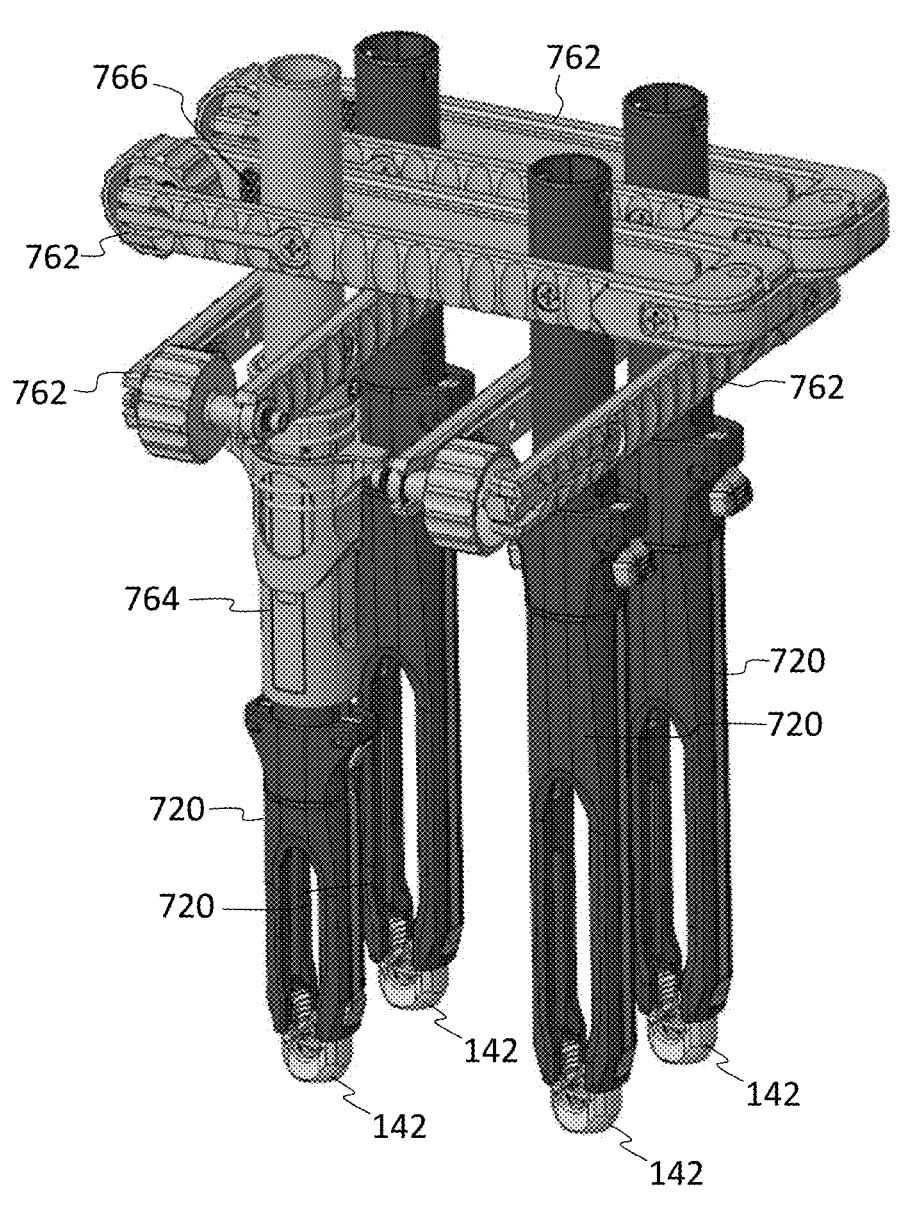
FIG. 44 shows a derotation assembly including derotation clamps attachable to reducers to perform correction maneuvers according to one embodiment.

Turning now to FIG. 44, a derotator assembly 760 is shown according to one embodiment. The derotator assembly 760 may include a plurality of reducers 720 or other reducers types secured together with one or more derotation clamps 762. The derotation clamps 762 may be attached directly to the reducer body or to a separate adapter 764, which connects to the proximal end of a reducer 720. These clamps 762 may link two or more reducers 720 together to perform a wide array of correction maneuvers. Knurled inner surfaces 766 of the derotation clamp 762 may be tightened to a knurled outer surface of the reducer 720 or adapter 764 with a driving nut to provide a rigid connection between reducers 720. Additional details of derotation systems and clamp members are described in U.S. Pat. No. 10,687,867, which is incorporated by reference herein in its entirety for all purposes.

Turning now to FIGS. 45A-47B, MIS compression/distraction instruments 800, 840 are shown for manipulating vertebrae during spinal surgery. In the embodiment shown in FIGS. 45A-45B, the compressor/distractor 800 is configured for multi-level compression and/or distraction of the vertebrae to which they are coupled. The multi-level instrument

800 may have an increased length of travel, allowing its mobile arm 806 to span across one or more vertebrae. In the embodiment shown in FIGS. 46A-47B, the compressor-distractor 840 is configured for single-level compression and/or distraction of the vertebrae to which they are coupled. The single level instrument may have a decreased travel length, such that it would not take up unnecessary working room during use.

Figure 45A:
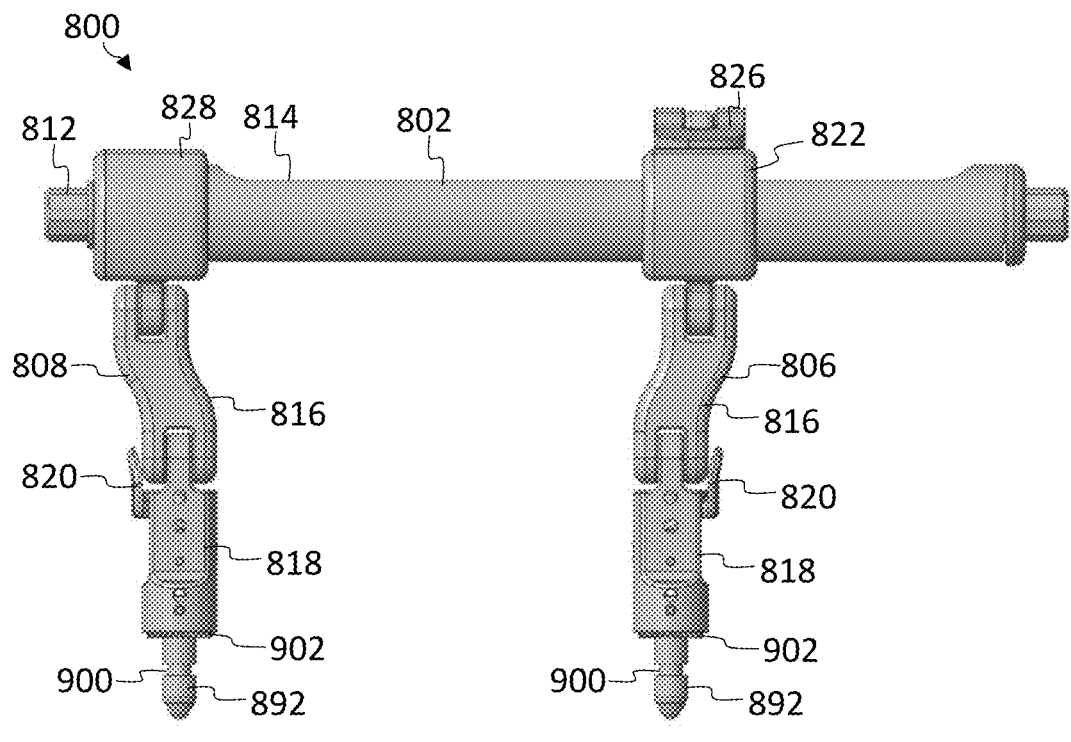
FIGS. 45A-45B show side and cross-sectional views, respectively, of a multi-level compressor/distractor instrument according to one embodiment.
Figure 45B:
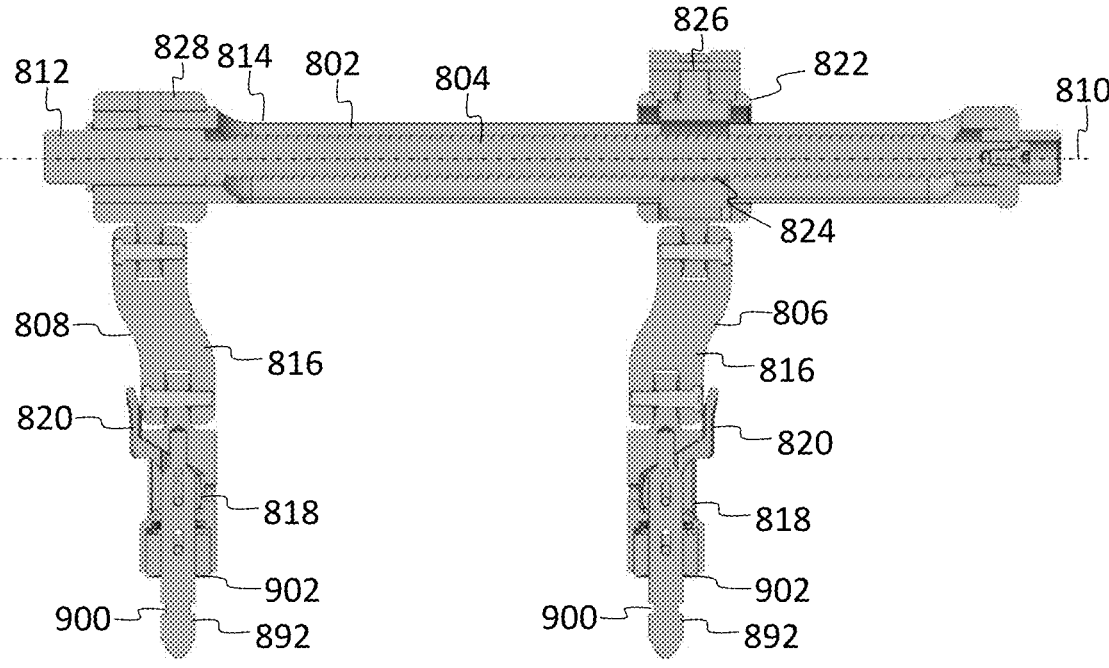

As best seen in FIGS. 45A-45B, the multi-level compressor/distractor 800 may include an outer rod housing 802, an inner driving rod 804, and two arms 806, 808. One arm 806 is a mobile arm and the other arm 808 is a fixed arm configured to be attached to MIS towers 600, or other suitable mechanism for attaching to the tulip assembly. The driving rod 804 may include a threaded rod located through the outer rod housing 802 and rotatable about a central axis 810. The threaded driving rod 804 may be actuated by a detachable handle 854 (best seen in FIG. 47B), for example, coupled to a tool engagement interface 812 at the end of the driving rod 804. The rod housing 802 may include an elongate opening 814 on the top of the housing 802 to expose the threaded rod 804 to the mobile arm 806.

The arms 806, 808 may include double-jointed member arms. For example, the arms 806, 808 may include two arm segments 816, 818 coupled to one another at a joint, allowing articulation between the arms segments 816, 818. Each arm 806, 808 may utilize a cam lever 820 to fix the relative position between the segments 816, 818. The mobile arm 806 may be attached to the rigid housing track 802 and threaded rod 804 with a collar 822. The collar 822 may define a threaded portion 824 that engages with the threaded rod 804. As the threaded rod 804 is rotated, the mobile arm 806 is configured to move along the threaded rod 804 to the desired location. The mobile arm 806 is able to shuttle along the threaded rod 804 and rigid housing track 802. In addition, the mobile arm 806 may be connected to the collar 822 at another joint allowing further positional adjustment. In this manner, the mobile arm 806 has the ability to articulate and swivel in multiple directions.

The mobile arm 806 may be fixed along threaded rod 804 with a threaded, selective engaging button mechanism. In one embodiment, the mobile arm 806 position may be fixed via cam lever 826, which includes locked and unlocked positions. In the unlocked position, the cam lever 826 is not engaged with the threaded rod 804 and the collar 822 and arm 806 may be free to slide along the driving rod 804, for example, by hand. In the locked position, the cam lever 826 is engaged with the threaded rod 804 and the collar 822 and arm 806 translate when the threaded rod 804 is rotated. It will be appreciated that the cam levers 820, 826 may be replaced with spring-loaded buttons or other securing mechanisms.

The fixed arm 808 may be attached to the housing 802 with a fixed collar 828. The fixed arm 808 is locked in place along axis 810 but is still free to articulate and pivot about joints connecting arm segments 816, 818 to the collar 828. Any of the joints may include Bellville washers or other mechanisms to provide memory in their movement, allowing the device to stay in place during use. In this embodiment, the fixed arm 808 may be positioned at a fixed axial location and the mobile arm 806 may translate with respect to the fixed arm 808 by rotation of the driving rod 804. It will be appreciated, however, that the arms 806, 808 may be reversed or both arms 806, 808 may be moveable arms depending on the application. Further details of a multi-level compressor/distractor instrument 800 is provided in U.S.

Publication No. 2023/0329758, which is incorporated by reference herein in its entirety for all purposes.

Figure 46A:
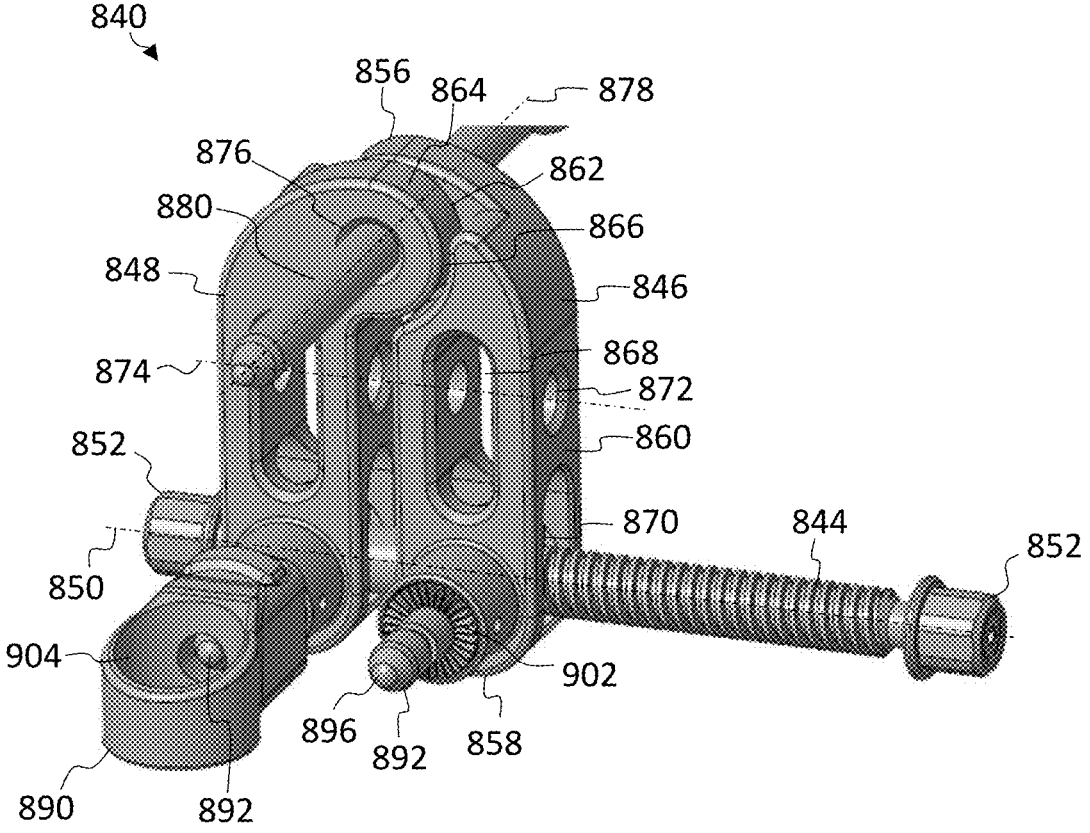
FIGS. 46A-46B show perspective and cross-sectional views, respectively, of a single level compressor/distractor instrument.
Figure 46B:
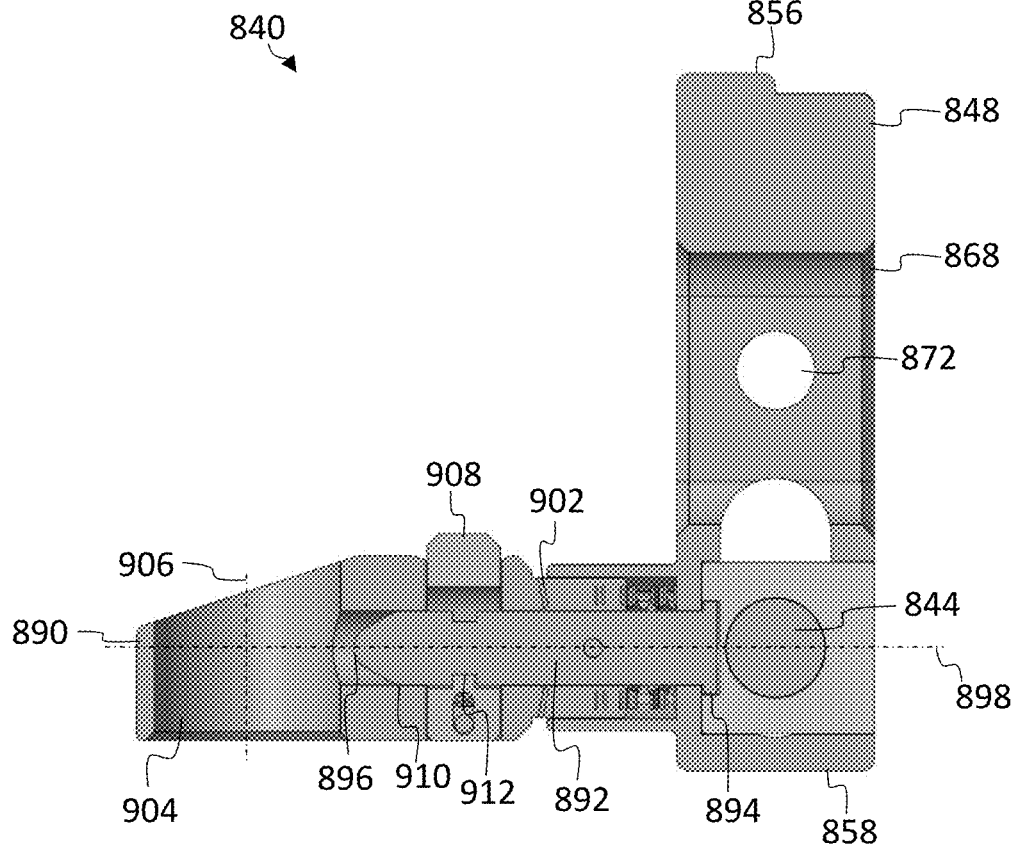

As best seen in FIGS. 46A-46B, a single level compressor/distractor 840 is shown according to one embodiment. Similar to compressor/distractor 800, the single lever compressor/distractor 840 includes a threaded driving rod 844 with a movable arm 846 and a fixed arm 848. The threaded driving rod 844 extends along central axis 852, and each end of the driving rod 844 includes a tool engagement interface 852. The tool engagement interfaces 852 may be actuated by a detachable handle 854 (best seen in FIG. 47B) to rotate the driving rod 844 and translate the moveable arm 846 along its length.

Each arm 846, 848 may include a body extending from a proximal portion 856 to a distal portion 858. Each arm 846, 848 may have a block-like body with a generally rectangular form having flat front, back, and side surfaces 860. The proximal and distal portions 856, 858 of the arms 846, 848 may be rounded with semi-circular or curved ends. The proximal portion 856 may have a nesting configuration 862 where the arms 846, 848 fit closely together. A pronounced rounded male interface 864 at the proximal end 856 nests within a corresponding rounded female interface 866, which may provide for pivotal movement between the arms 846, 848. The arms 846, 848 may have elongated obround slots 868 extending between the proximal and distal ends 856, 858, forming a hollow body between the front and back faces of the arms 846, 848.

Each arm 846, 848 includes a threaded through opening 870 for receiving the threaded rod 844 along central axis 850. Each arm 846, 848 includes bores 872, 876 for receiving a detachable fulcrum instrument 880. A first set of bores 872 through arms 846, 848 may be provided along axis 874, which is parallel to the central axis 850. A second set of bores 876 through arms 846, 848 may be provided along axis 878, which is perpendicular to the central axis 850. Depending on which set of bores 872, 876 is selected, the user is able to toggle between parallel and lordotic motion. When the detachable fulcrum 880 is inserted through the first set of bores 872, the fulcrum acts as a guide rail for the arms 846, 848 to translate across. When the detachable fulcrum 880 is inserted through the second set of bores 876, as shown in FIG. 46A, the fulcrum 880 act as a pivot point for the arms 846, 848.

In both embodiments, for the multi-level and single level compressor/distractors 800, 840, a modular connector tip 890 may be coupled to each respective arm 806, 808, 846, 848 for securing a MIS tower 600, or other suitable tulip connector. A connection to arm 848 will be described in further detail, but it will be appreciated that it equally applies to all other arms 806, 808, 846 as well. The distal end 858 of arm 848 includes a connector post 892 configured to secure modular connector tip 890 (best seen in FIG. 46A), allowing instruments 800, 840 to be used across multiple platforms or in hybrid situations. The connector post 892 extends from an attachment end 894 to a free end 896, with a tapered or rounded nose. The connector post 892 defines a circumferential groove 900 configured to interface with the modular connector tip 890. In the case of the multi-level instrument 800, the connector posts 892 extend distally from the second arm segments 818 but may be reoriented about the joint between segments 816, 818. In the case of the single-level instrument 840, the connector posts 892 are fixed and oriented along axis 898, which is generally perpendicular to central axis 850.

The modular connector tip 890 may provide for 360 degrees of swiveling about the post 892. The position of the connector tip 890 may be locked by a lockable gear tooth connection 902, which may be similar to rotation lock 308. The gear tooth connector 902 may include a plurality of radial teeth about the post 892. The base of connector tip 890 includes corresponding gear teeth, which mate with gear teeth 902, thereby locking the relative position of connector tip 890 relative to post 892. The gear teeth 902 may be spring-loaded into the connector 890 to achieve maximum tooth engagement. The modular connector tip 890 includes a body defining a circular through opening 904 sized and dimensioned to receive the MIS tower 600, or other tulip connector. Opening 904 may extend along axis 906, which is generally perpendicular to post axis 898. As best seen in FIG. 46B, the tip connector 890 may be secured to the post 892 via button 908. The tip connectors 890 may employ a spring-loaded button 892, which locks into groove 900 tightly centered about the gear teeth 902. When the post 892 is inserted into post opening 910 in the tip 890, button 908 may be spring-loaded such that a protrusion 912 automatically engages with groove 900 in post 892. In this manner, the modular connector tip 890 is axially and rotationally locked to the post 892. When the button 908 is depressed, the protrusion 912 exits groove 900 and the post 892 may be withdrawn from the connector tip 890.

Figure 47A:
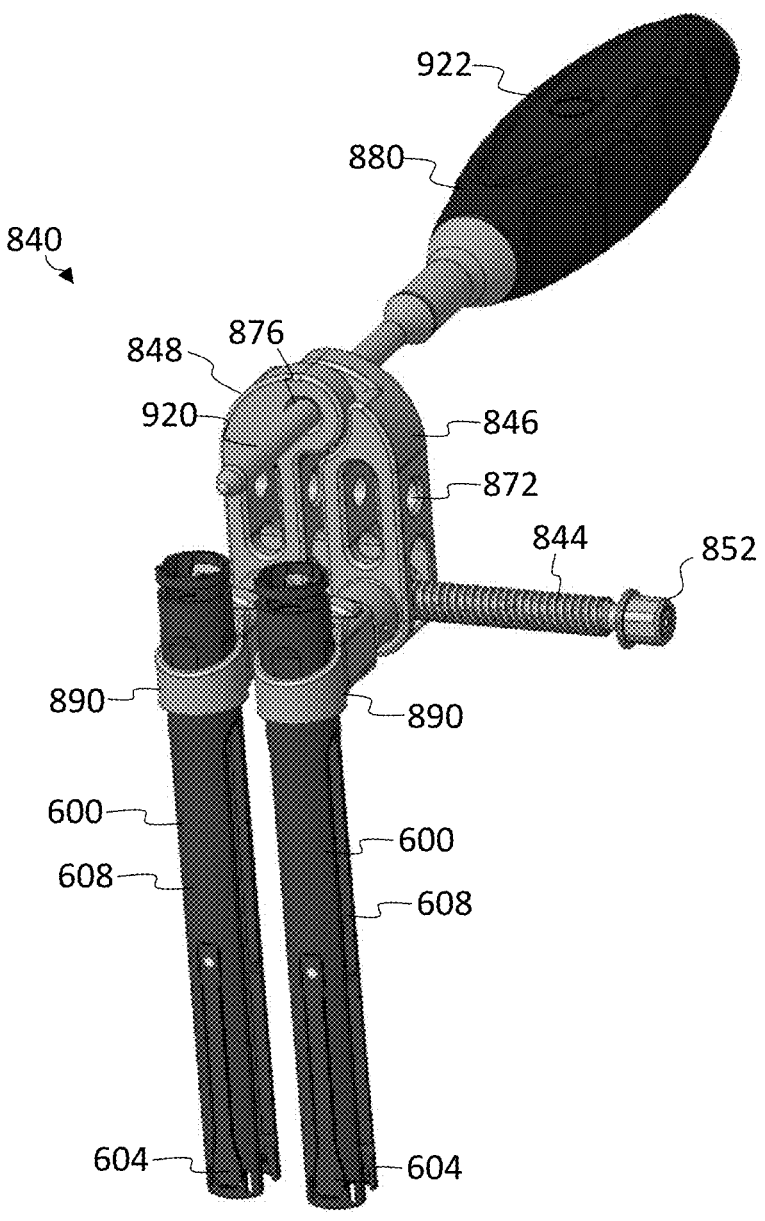
FIGS. 47A-47B show the single level compressor/distractor arranged in lordotic and parallel modes, respectively.
Figure 47B:
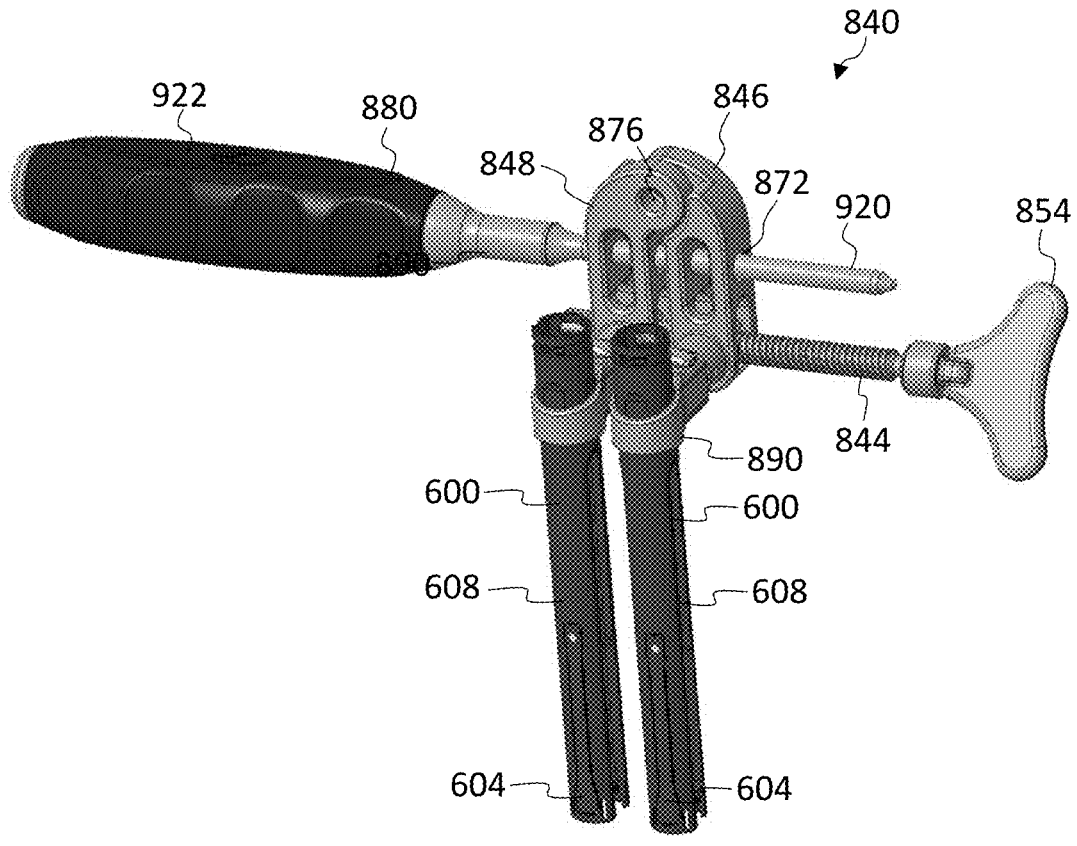

FIGS. 47A-47B show the single lever compressor/distractor 840 with the MIS towers 600 positioned through modular tips 890 and detachable fulcrum instrument 880 placed in two different orientations, lordotic and parallel. The detachable fulcrum instrument 880 may include a smooth shaft 920 with a handle 922 aligned along a central tool axis. In FIG. 47A, single lever compressor/distractor 840 is set up in lordotic mode. In lordotic mode, the shaft 920 of the fulcrum 880 is positioned through the second set of bores 876 in arms 846, 848. When the threaded shaft 844 is rotated, mobile arm 846 translates along shaft 844, and arm 846 pivots about fulcrum 880, thereby providing lordotic motion to the tulips 12 attached to MIS towers 600 (shown in FIGS. 37A-37C). In FIG. 47B, the single level compressor/distractor 840 is set up in parallel mode. In parallel mode, the shaft 920 of the fulcrum 880 is positioned through the first set of bores 872 through arms 846, 848 and the fulcrum 880 acts as a guide rail for the arms 846, 848 to translate across in parallel. When the threaded shaft 844 is rotated via detachable handle 854, mobile arm 846 translates along shaft 844, and arm 846 translates in parallel across fulcrum 880, thereby providing parallel motion to the tulips 12 attached to MIS towers 600 (shown in FIGS. 37A-37C).

The devices and assemblies described herein provide for pedicle screw systems with increased strength, decreased splay, improved instrument connections, and a variety of implant options to suit different pathologies. The pedicle screw system may include varying types of heads (polyaxial, modular, reduction, uniplanar, monoaxial, S2AI, closed head), and varying types of screws (solid, cannulated, fenestrated, single step, ONE, cortical, DOD, corticocancellous, HA coated). The systems may be used for both open and percutaneous (MIS) approaches for a variety of conditions including degenerative conditions, deformities, tumors, traumas, and infections. Mating instruments interface with connecting features on the screw head and screws for insertion, manipulation, correction, and locking of implants. MIS Towers may be attached to the screw heads to provide a guide and working channel for percutaneous approaches. Screwdrivers may be used for placement of screws under fluoroscopic, image guided, and robotic guided approaches. Screw extenders may be used for registration and tracking of bony anatomy. Correction instruments may be used for reduction, segmental derotation, en-bloc derotation, global derotation, compression, and/or distraction. The instruments may help to improve accuracy of navigated and robotic techniques as well as the ability to achieve correction through open and percutaneous approaches.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. An orthopedic fixation assembly comprising:
a tulip assembly including a tulip head, a saddle, a retaining clip, and a friction ring, the tulip head has two arms defining a rod slot therebetween and a bore extending therethrough, the saddle is receivable in the bore of the tulip head, the saddle has an upper surface defining a rod seat aligned with the rod slot, the retaining clip is positioned at a bottom of the tulip head, and the friction ring is positioned between the saddle and the retaining clip; and
a bone fastener including a screw head receivable in the tulip head and a shaft configured for engaging bone, wherein the screw head includes helical grooves, and the friction ring is located around the screw head and in engagement with the helical grooves to help the tulip head retain its angular position relative to the bone fastener when positioned by a user.

2. The orthopedic fixation assembly of claim 1, wherein the retaining clip includes a split ring configured to rest in a corresponding groove in the tulip head.

3. The orthopedic fixation assembly of claim 2, wherein the retaining clip includes an upper radial neck configured to rest on a shelf in the groove in the tulip head.

4. The orthopedic fixation assembly of claim 1, wherein the friction ring includes a split ring configured to rest in a corresponding groove in the tulip head.

5. The orthopedic fixation assembly of claim 4, wherein the friction ring has a smooth circular profile and the groove has a semi-circular cross section to accommodate the friction ring.

6. The orthopedic fixation assembly of claim 1 further comprising a locking cap having an outer body defining a thread, wherein the locking cap is threadable between the two arms of the tulip head to secure a rod therein.

7. The orthopedic fixation assembly of claim 6, wherein the locking cap includes a circular groove in a top face surrounding a drive recess, wherein the circular groove is configured to receive one or more prongs from a driver to retain the locking cap.

8. The orthopedic fixation assembly of claim 6, wherein when the locking cap is threaded downwardly onto the rod, the rod pushes against the rod seat of the saddle, and the saddle secures the bone fastener in a locked position.

\* \* \* \* \*